US012198529B2

(12) United States Patent
Neubauer

(10) Patent No.: US 12,198,529 B2
(45) Date of Patent: Jan. 14, 2025

(54) SYSTEMS AND METHODS TO MANAGE A TASK BASED ON A STAFF MEMBER'S DYNAMIC ATTRIBUTES

(71) Applicant: Marc Neubauer, Silver Spring, MD (US)

(72) Inventor: Marc Neubauer, Silver Spring, MD (US)

( * ) Notice: Subject to any disclaimer, the term of this patent is extended or adjusted under 35 U.S.C. 154(b) by 199 days.

(21) Appl. No.: 17/745,041

(22) Filed: May 16, 2022

(65) Prior Publication Data
US 2023/0005357 A1 Jan. 5, 2023

Related U.S. Application Data

(63) Continuation-in-part of application No. 17/506,673, filed on Oct. 21, 2021, now Pat. No. 11,380,186.

(60) Provisional application No. 63/268,015, filed on Feb. 15, 2022, provisional application No. 63/246,241, filed on Sep. 20, 2021, provisional application No. 63/236,788, filed on Aug. 25, 2021, provisional application No. 63/214,409, filed on Jun. 24, 2021.

(51) Int. Cl.
G08B 25/00 (2006.01)
G08B 21/18 (2006.01)
(52) U.S. Cl.
CPC ........... G08B 25/005 (2013.01); G08B 21/18 (2013.01)
(58) Field of Classification Search
CPC .................................. G08B 25/005; G08B 21/18
See application file for complete search history.

(56) References Cited

U.S. PATENT DOCUMENTS

| | | | |
|---|---|---|---|
| 6,998,978 B2 | 2/2006 | Kirkeby |
| 7,432,807 B2 | 10/2008 | Schmitt |
| 7,551,078 B2 | 6/2009 | Carlson |
| 7,671,733 B2 | 3/2010 | McNeal |
| 7,749,164 B2 | 7/2010 | Davis |
| 7,920,061 B2 | 4/2011 | Klein |
| 8,392,232 B2 | 3/2013 | McGillin |
| 8,571,884 B2 | 10/2013 | Badgett |
| 8,655,680 B2 | 11/2014 | Bechtel |
| 9,052,809 B2 | 6/2015 | Vesto |
| 9,129,501 B1 | 9/2015 | King |
| 9,356,888 B2 | 5/2016 | Gross |
| 9,393,366 B2 | 7/2016 | Gannon |
| 9,649,073 B2 | 5/2017 | Voalte |
| 9,727,829 B2 | 8/2017 | Bollapragada |
| 9,734,301 B2 | 8/2017 | King |
| 9,830,801 B2 | 11/2017 | Rusin |
| 10,062,274 B2 | 8/2018 | Wilson |
| 10,064,579 B2 | 9/2018 | Condurso |
| 10,210,953 B2 | 2/2019 | Greer |
| 10,242,060 B2 | 3/2019 | Butler |

(Continued)

OTHER PUBLICATIONS

ECRI. Evaluation background: ancillary alarm notification systems. Health Devices Dec. 22, 2016.

(Continued)

Primary Examiner — Hongmin Fan

(57) ABSTRACT

A method for managing an alarm issued by a medical device is disclosed. The method includes the steps of receiving the alarm from the medical device, ranking a staff member based in part on a dynamic attribute that is associated with the staff member, selecting a recipient based in part on the ranking, and providing an alert to the recipient.

16 Claims, 25 Drawing Sheets

(56) References Cited

U.S. PATENT DOCUMENTS

| | | | |
|---|---|---|---|
| 10,275,570 B2 | 4/2019 | Norton | |
| 10,289,107 B2 | 5/2019 | Warner | |
| 10,300,194 B2 | 5/2019 | Day | |
| 10,347,373 B2 | 7/2019 | Voalte | |
| 10,453,157 B2 | 10/2019 | Kamen | |
| 10,463,788 B2 | 11/2019 | Day | |
| 10,617,815 B2 | 4/2020 | Day | |
| 10,642,961 B2 | 5/2020 | Portnoy | |
| 10,765,379 B2 | 9/2020 | Perschbacher | |
| 10,813,580 B2 | 10/2020 | Dyell | |
| 10,898,641 B2 | 1/2021 | Day | |
| 10,916,119 B2 | 2/2021 | Baker | |
| 10,957,445 B2 | 3/2021 | Faulks | |
| 11,437,125 B2 | 9/2022 | Cossler | |
| 2005/0242928 A1* | 11/2005 | Kirkeby | G08B 5/22 340/286.07 |
| 2007/0001806 A1 | 1/2007 | Poll | |
| 2008/0235057 A1 | 9/2008 | Weidenhaupt | |
| 2012/0215578 A1* | 8/2012 | Swierz, III | G06Q 10/063 705/7.14 |
| 2012/0284053 A1 | 11/2012 | Rosenfeld | |
| 2013/0275539 A1 | 10/2013 | Gross | |
| 2013/0296823 A1 | 11/2013 | Melker | |
| 2017/0372020 A1 | 12/2017 | Govro | |
| 2019/0240405 A1 | 8/2019 | Wehba | |
| 2019/0307405 A1 | 10/2019 | Terry | |
| 2020/0066401 A1* | 2/2020 | Guelich | G16H 40/20 |
| 2020/0335209 A1 | 10/2020 | Holscher | |
| 2021/0027887 A1 | 1/2021 | Sampath | |
| 2021/0252210 A1 | 8/2021 | Day | |
| 2022/0108790 A1* | 4/2022 | Rice | G16H 10/20 |
| 2022/0129823 A1* | 4/2022 | Amato | G06Q 10/06398 |
| 2022/0230714 A1 | 7/2022 | Batman | |

OTHER PUBLICATIONS

ECRI. Evaluation: Extension Engage ancillary alarm notification system. Health Devices Dec. 22, 2016.

Speich, Reducing Alarm Fatigue in the Intensive Care Unit: A Quality Improvement Research Study, (2017). Doctoral Dissertation, Uni of Conn.

Au-Yeung, Reduction of false alarms in the intensive care unit using an optimized machine learning based approach, Digital Medicine (2019) 2:86.

Delft Design Labs, Silent ICU—Intensive Care Alarm System, Joint Master Project Feb.-Jun. 2017.

McFarlane, Faster clinical response to the onset of adverse events: A wearable metacognitive attention aid for hurse triage of clinical alarms. (2018) PLoS ONE 13(5).

Vocera, product description for Engage: workflow engine, downloaded Sep. 2021.

Vocera, Solution Brief, Engage, downloaded Sep. 2021.

Kooman, Reducing medical device alarms by an order of magnitude: A human factors approach, Anaesthesia and Intensive Care, 2021, vol. 49(1) 52-61.

Pater, Time series evaluation of improvement interventions to reduce alarm notifications in a paediatric hospital, BMJ Qual Safe 2020, vol. 29:717-726.

Vitoux, Perceptions of Infusion Pump Alarms, The Ar & Science of Nursing, vol. 41(5) Sep.-Oct. 2018.

* cited by examiner

SYSTEMS AND METHODS TO MANAGE A TASK BASED ON A STAFF MEMBER'S DYNAMIC ATTRIBUTES

CROSS-REFERENCE TO RELATED APPLICATIONS

This application claims priority to U.S. Provisional Application 63/268,015 filed on Feb. 15, 2022 and to U.S. Non-Provisional application Ser. No. 17/506,673 filed Oct. 21, 2021, which claims priority to U.S. Provisional Applications 63/246,241 filed on Sep. 20, 2021, 63/236,788 filed on Aug. 25, 2021, and 63/214,409 filed on Jun. 24, 2021, each of which is hereby incorporated in their entirety herein by reference.

BACKGROUND

Field

This disclosure relates to systems and methods of managing alarms of medical devices, particularly in a hospital.

Description of the Related Art

Alarms are an ever-present background in a hospital environment. Medical devices, e.g., patient monitors, ventilators, infusion pumps, etc., issue alarms for conditions that range from a routine need for service to life-threatening conditions. With conventional alarm priorities limited to "high," "medium," and "low," the criticality of any given alarm may not actually require the skill level of the person to whom the alarm is directed. Clinicians often find they are responding to conditions that do not require their skill level and could have been handled by a junior clinician. This results in a higher-than-necessary number of alarms being sent to the primary designated clinician. The sheer number of alarms received by such clinicians, particularly when the condition is not as serious as it appeared upon receipt of the alarm, exacerbates alarm fatigue.

Alarm fatigue can occur not just from the sheer number of alarms but also the loudness of audible alarms, the number of high-priority alarms that do not require an urgent response, and the duplicative efforts of sending the same alarm to multiple people. Alarm fatigue is also exacerbated by the great number of audible signals coming from alarms from different medical devices located in a patient's room. Most of the time, clinicians are not in the room and the medical device alarms continue to generate audible signals until a clinician arrives to respond. The audible signals create unnecessary noise that raises the anxiety and frustration of both patients and family members and causes an environment that does not promote patient healing.

SUMMARY

There is a need for an Alarm Management System that directs alerts to the lowest-level staff member who can handle the underlying conditions and reduces the number of audible alarms. It is further desirable to provide variable escalation time delays that are suitable for the criticality of the underlying condition. It is also beneficial to provide more information to the recipient of an alert.

In certain embodiments, a method for managing an alarm issued by a medical device is disclosed. The method includes the steps of receiving the alarm from the medical device, ranking a staff member based in part on a dynamic attribute that is associated with the staff member, selecting a recipient based in part on the ranking, and providing an alert to the recipient.

In certain embodiments, a system for managing an alarm issued by a medical device is disclosed. The system has a processor configured to receive the alarm and provide an alert and a memory communicatively coupled to the processor. The memory includes a dynamic attribute of a staff member, an algorithm for retrieving the dynamic attribute and ranking the staff member based in part on the dynamic attribute and selecting a recipient based in part on the ranking, and instructions that, when loaded into the processor and executed, cause the processor to execute the algorithm upon receipt of the alarm and provide the alert to the recipient.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
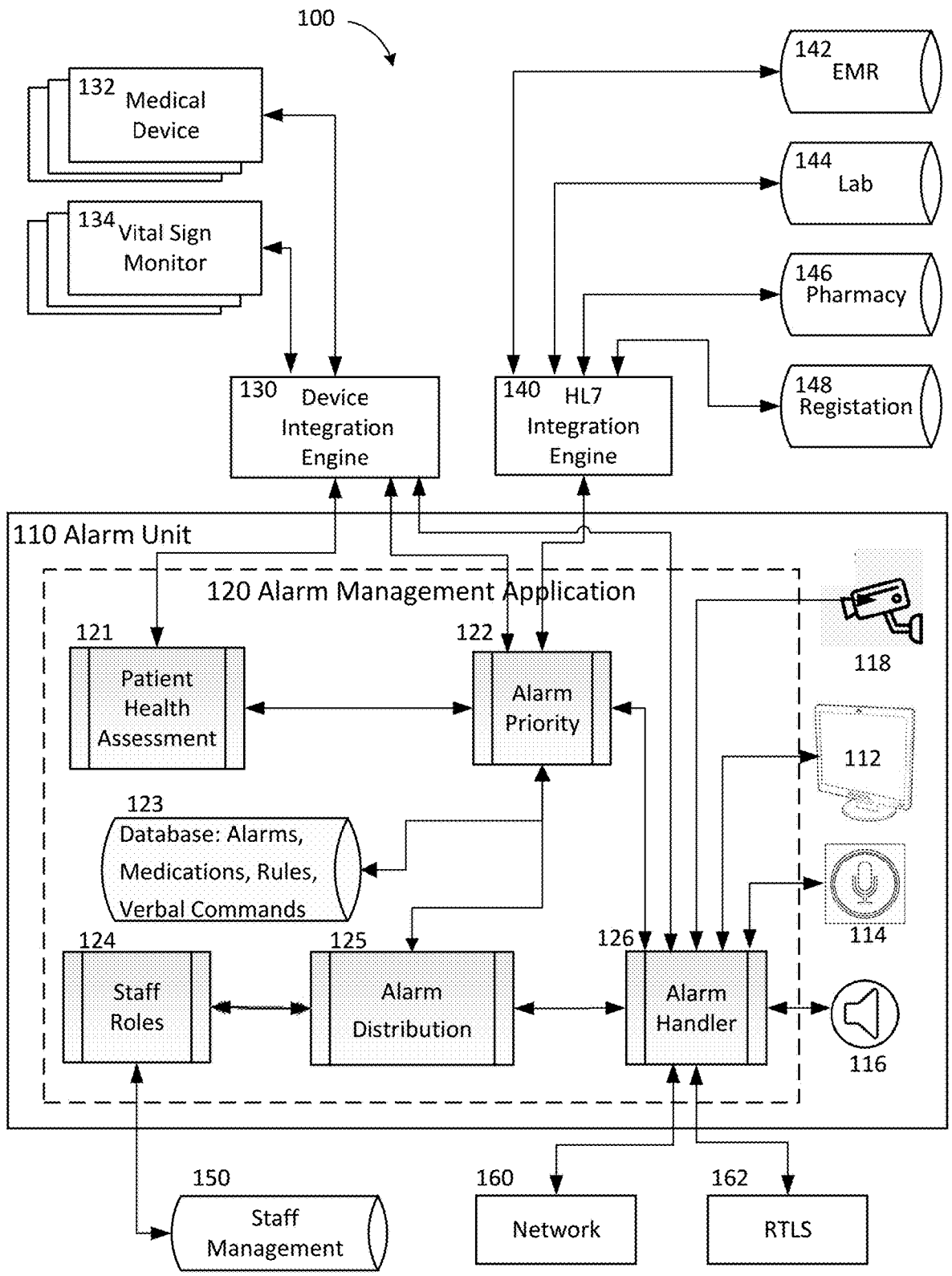
FIG. 1 is an exemplary block diagram of an Alarm Management System, according to certain aspects of the present disclosure.

The following description discloses a system and method that provides alarm sub-priority classes, a system and method of assigning sub-priorities based on the clinical need associated with the alarm, a system and method of selecting an alert recipient clinician or staff member having the skills necessary to resolve the alarm, and a system and method of dynamically adjusting the escalation and silencing of alarms.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. It will be apparent, however, to those skilled in the art that the subject technology may be practiced without these specific details. In some instances, well-known structures and components are shown in block diagram form to avoid obscuring the concepts of the subject technology. Like, or substantially similar, components are labeled with identical element numbers for ease of understanding.

As used within this disclosure, the term "alarm" refers to a signal received from a medical device indicating detection of a condition that requires attention by an operator or clinician. This term also may refer to a name or identifier associated with the detected condition.

As used within this disclosure, the phrase "active alarm" refers to an alarm that has been issued by a medical device, wherein the underlying condition has not yet been corrected. Depending on the underlying condition, the alarm may be assigned a low sub-priority but still represents a pending task that must be addressed.

As used within this disclosure, the term "alert" refers to a signal sent to a staff member and/or presented to the staff member, e.g., on a device in the patient's room or on a personal device) in an audible and/or visual manner.

As used within this disclosure, the phrase "device task" refers to a task performed on a medical device, e.g., setting up and programming an infusion on an infusion pump.

As used within this disclosure, the phrase "patient task" refers to a task performed on a patient with or without a device, e.g., collecting a lab specimen, patient monitoring, or performing a patient-requested task.

As used within this disclosure, the phrase "personal device" refers to any means of receiving audible or visual communication, including but not limited to a pager, a phone, a watch, a two-way audio communicator, a tablet, a laptop, or a desktop computer. A personal device may be carried by the staff member, a mobile workstation, or located at a fixed location, e.g., a nursing workstation.

As used within this disclosure, the term "sub-priority" refers to a priority that is a further refinement of the conventional priorities of "high," "medium," and "low." The naming convention for sub-priorities used herein consists of a single letter associated with one of the conventional priorities. e.g., an "H," concatenated with a subdivision number, e.g., a "1," producing a sub-priority identifier, e.g., "H1." This term also includes other naming schemes, including replacement of the "H-M-L" set of names with larger number of discrete levels, including but not limited to numbers, e.g., 1-10, etc., letters, e.g., HHH, HH, H, etc., symbols, e.g., *, , *, etc., words, e.g., crisis high, crisis medium, crisis low, etc., or any combination therein, e.g., Crisis 1, Crisis 2, Crisis 3, etc. In certain embodiments, a sub-priority comprises a conventional priority.

As used within this disclosure, the phrase "treat the patient" or similar includes administering therapy from a device, e.g., infusion pump, ventilator, etc., and using a device to monitor or measure a patient health measurement, e.g., a patient monitor. This activity can be passive and only provide information.

As used within this disclosure, the phrase "dynamic attribute" refers to all changeable factors associated with a patient or a staff member. Dynamic attributes may influence one or more of an association of a sub-priority with an alarm, a determination of an alert recipient, or an action taken by the Alarm Management System. Distributing alerts based on dynamic attributes is important to reduce alarm fatigue. Patient dynamic attributes include, but are not limited to, the examples listed in Table 1. Dynamic attributes associated with a staff member include, but are not limited to, the examples listed in Table 10.

Dynamic Attributes of Patients

TABLE 1

| | | FACTOR | EXAMPLE |
|---|---|---|---|
| Patient Monitor Factors (currently being measured or periodically assessed) | | | |
| 1 | | patient health | |
| | a. | a patient health measurement | vital signs, labs, point of care parameter, diagnostic test result |
| | b. | change in the score of a patient health assessment | Modified Early Warning Score (MEWS), Acute Physiology and Chronic Health Evaluation (APACHE) 2 |
| 2 | | an action by the patient | |
| | a. | detection of motion | patient motion detected directly at same time as alarm known to be induced by motion |

TABLE 1-continued

|  | FACTOR | EXAMPLE |
|---|---|---|
| b. | loss of signal; abnormal signal | patient motion disconnects an EKG lead causing alarm for low pulse rate |

Identification, Treatment, and Diagnostic Factors (from a hospital system)

|  |  | FACTOR | EXAMPLE |
|---|---|---|---|
| 3 |  | a doctor's order | administer a medication (dose, method, frequency, etc.), specific settings of a medical device |
| 4 |  | a patient instruction | a Do Not Resuscitate (DNR) order |
| 5 |  | patient medical record |  |
|  | a. | a patient identifier | Age, gender, ethnicity, blood type, height, weight |
|  | b. | a diagnosis of an underlying condition of the patient | heart disease, congenital heart defect, diabetes |
|  | c. | an inherent characteristic of the patient | a genetic marker, an inherited condition, e.g., patient is a carrier of hemophilia |
|  | d. | whether patient has received a treatment that affects a condition | an implanted device |
|  | e. | whether a patient has previously experienced a symptom for a condition | note in electronic medical record (EMR) of fainting, dizziness, nausea |
|  | f. | changes in a patient's condition | worsens or improves after an intervention |

Medication Factor (from medication library in a hospital system or standalone medication library)

|  |  | FACTOR | EXAMPLE |
|---|---|---|---|
| 6 |  | an indication for use of a medication or fluid being administered to the patient; | Vasopressors are indicated to raise blood pressure (BP) |
| 7 |  | characteristics of medication or fluid |  |
|  | a. | intended effect | blood thinning medications indicated for patients with atrial fibrillation to reduce chance of stroke |
|  | b. | side effect | thyroid medication can cause very fast heart rate and irregular heart rhythm |
|  | c. | patient health measurement affected by a medication | vasopressors increase blood pressure, insulin lowers blood sugar |
|  | d. | pharmacokinetic or pharmacodynamic (PK/PD) characteristic | PK - e.g., biological half-life PD - e.g., drug-drug interactions |

Medical Device Factors (configuration or operational performance)

|  | FACTOR | EXAMPLE |
|---|---|---|
| 8 | a setting of the medical device | delivery rate of an IV fluid; oxygen content of delivered air |
| 9 | an operating mode of the medical device | running on battery power, ventilator set to allow spontaneous breathing |
| 10 | an operational status of the medical device | infusion pump has stopped infusing a fluid; a ventilator has stopped |
| 11 | a measured aspect of operation of the medical device | Measured battery voltage (indication of remaining operational time), tidal volume of each breath |
| 12 | whether there is a secondary mechanism to mitigate harm associated with alarm | tidal volume sensing as secondary indication of respiration if airway pressure alarm occurs, back-up battery |
| 13 | A feature of a device | Electrocardiogram (ECG) filter mode, number of leads used for monitoring |
| 14 | number of previous nonactionable or false alarms received before alarm received | high number indicates artifact, reliability issues, or environmental issues, e.g., electromagnetic interference |
| 15 | estimated time to perform a corrective action | replace a non-operational ventilator or pump |
| 16 | recommended replacement interval of a consumable | ECG leads should be changed 1x or 2x per day to reduce false alarms |

As used within this disclosure, the phrase "patient health measurement" refers to one or more of the following patient characteristics: a vital sign, a point-of-care (POC) observation or symptom, a diagnostic test, or a laboratory test. These measurements include but are not limited to body temperature, heart rate, blood pressure, respiration rate, tidal volume, blood oxygenation, blood glucose level, an arrhythmia, and end-tidal carbon dioxide ($ETCO_2$).

As used within this disclosure, the phrase "laboratory test" refers to analysis of a biological sample from the patient, e.g., blood. The analysis may be performed at the bedside or at a remote location.

As used within this disclosure, the phrase "patient health assessment" is an algorithm that may be used to categorize a patient's health or cognitive status, to triage a patient, or to monitor a patient to determine if their condition is improving or worsening. A patient health assessment may be a nationally or locally recognized set of criteria or algorithm or one defined and implemented by a hospital or network of hospitals. For example, a patient's acuity status may be evaluated using the Oulu Patient Classification System. The complexity of a patient's condition may be evaluated using the Charlson Comorbidity Index (CCI) or the Patient Clinical Complexity Level (PCCL) algorithms. Deterioration of a patient may be monitored by the Modified Early Warning System (MEWS). A patient's cognition status may be evaluated using the Standardized Mini Mental State Examination (SMMSE) or the Rowland Universal Dementia Assessment Scale (RUDAS). The likelihood of an adverse event, such as the patient falling, may be evaluated using the Morse Falls Scale (MFS). Other examples of patient health assessments include a patient pain algorithm, a patient disease severity algorithm, a patient awareness algorithm, a patient agitation algorithm, a patient deterioration algorithm, and a mortality score such as the APACHE 2.

A non-actionable alarm is one that does not require a clinical intervention or corrective action and includes false-positive alarms that indicate a given condition exists when it does not.

Staff Roles

Medical device alarms require clinicians or technicians to perform corrective action to address the cause of the alarm, improve patient outcomes, restore the device to normal functioning or replace the device with a functioning one. Corrective actions for clinical alarms are usually performed by clinicians, but technical alarms may be addressed by either clinicians or other staff, e.g., technicians, orderlies, etc.

In certain embodiments, the disclosed system defines multiple staff roles associated with levels of training and/or specific skills. Table 2 is an exemplary embodiment of defined staff roles. In this example, there are four clinical roles S1, S2, S3, S4 and a technician role S5. Primary care nurses, e.g., S2, perform most of the care of the patient, program medical devices, and address most alarms. In some settings, e.g., a surgical suite, specialists such as anesthesiologists, e.g., S1, program infusion pumps to administer anesthetics and controlled substances and will also address alarms. For ventilators, S1 may include respiratory therapists to troubleshoot complex situations and change ventilator and alarm settings. If the primary clinician, e.g., S2, is busy, then the Alarm Management System will forward the alarm information and sub-priority to a back-up clinician, e.g., S3, to ensure patient care needs are addressed in a timely fashion. S4 is defined as clinicians with less skill, e.g., LPNs, or less experience, e.g., medical students, new nurses in training, etc., who are capable of handling certain alarm conditions and can therefore relieve alarm fatigue of the S1-S3 roles. S5 is defined as technicians, staff, and orderlies who do not have a clinical background but are capable of resolving routine technical alarms.

TABLE 2

| Role | Training or skill |
|------|-------------------|
| S1 | primary care physician, surgeon, anesthesiologist, respiratory therapist |
| S2 | primary care nurse |
| S3 | backup nurse |
| S4 | licensed practical nurse (LPN), medical student, new nurse in training |
| S5 | technician, staff, orderly |

In certain circumstances, for example a small hospital or clinic, there may be a limited number of staff and a single staff role, e.g., S2, may receive alerts for all sub-priorities. In larger facilities with a greater number and range of staff, the system of the present disclosure implements a risk-based approach to responding to alarms and associates different roles with different sub priorities. In certain embodiments, the primary clinician, e.g., the S2 role, is assigned a limited number of patients, e.g., 5 patients, and a secondary clinician, e.g., a S3 or S4 role, is assigned to provide back-up for a larger number of patients, e.g., 20 patients. With a larger patient to clinician ratio, the S4 clinician may be given lower sub-priority alerts with longer recommended response times as defined in Table 3 below.

Sub-Priorities

In certain embodiments, the disclosed system defines multiple sub-priorities. Table 3 provides an exemplary embodiment of defined sub-priorities. Although Table 3 describes nine sub-priorities, the disclosed system includes embodiments that provide more or fewer discrete sub-priorities.

TABLE 3

| Role | Recommended Response Time to Address Alarm | Condition |
|------|--------------------------------------------|-----------|
| H1 | Immediate Response Required | immediate life-threatening condition |
| H2 | Within 1 minute | near-term life-threatening condition |
| H3 | Within 3 minutes | short-term risk of severe injury |
| M1 | Within 5 minutes | need for immediate attention |
| M2 | Within 10 minutes | need for near-term attention |
| M3 | Within 15 minutes | device requires adjustment |
| L1 | Within 30 min | fault in primary system with a back-up system in operation |
| L2 | >>30 min | requires near-term service |
| L3 | non-actionable | routine service |

In certain embodiments of the disclosed system, the system provides specificity for high priority alarms, enabling the notified clinician to determine whether they must drop what they are doing and immediately respond to an alarm to prevent patient harm, e.g., H1, or if the clinician has a few minutes to do so, e.g., H2 and H3. The alarm specificity provided in this disclosed system ensures that the highest sub-priorities are reserved for situations where the onset of life-threatening harm is immediate.

In certain embodiments of the present disclosure, one dynamic attribute is enough to define the sub-priority of an alarm. In other embodiments, one or more dynamic attributes are needed to define a sub-priority for a given alarm.

In certain embodiments of the present disclosure, an H1 sub-priority is assigned for an alarm associated with an infusion pump where all four of the following dynamic attributes are met: 1) the alarm stops the infusion, 2) the medication that is infusing is associated with a critical indication for use, 3) the medication affects a patient health measurement that is outside its normal range, and 4) the estimated time to perform a corrective action is greater than several minutes. A system error, e.g., a pump failure on an infusion pump that is infusing norepinephrine, meets these four criteria since the system error stops the infusion and Norepinephrine has a critical indication for use (it raises blood pressure for a patient with low pressure). Resolution of this example failure requires a lengthy corrective action that involves retrieving a new pump, connecting the pump to the patient, and reprogramming the infusion into the pump.

In certain embodiments, an H2 sub-priority is assigned for an air-in-line alarm on a pump infusing norepinephrine to a patient with low blood pressure. An air-in-line alarm stops the pump and norepinephrine has a critical indication for use and it affects a patient health measurement (it raises blood pressure for a patient with low pressure). An air-in-line alarm does not require a lengthy corrective action, however, and a nurse can resolve an air-in-line alarm by purging the line much quicker than getting a new pump, connecting the administration line, waiting for the replacement pump to start up, and reprogramming the pump. Addressing the air-in-line alarm in this way is routine and results in the patient being without a critical medication for less time, compared to the above example and warrants a lower sub-priority, e.g., H2.

In certain embodiments, an H3 alarm is assigned when an air-in-line alarm is associated with morphine for treating pain. In this scenario only the first two criteria from the H1 example are met. The air-in-line alarm stops the infusion and morphine has a critical indication for use. Morphine does not affect a patient health measurement or have a significant PK characteristic (i.e., short half-life). A patient not receiving morphine for a period of time is less critical than a patient not receiving norepinephrine and therefore a lower sub-priority, e.g., H3, is warranted for morphine.

In certain embodiments of the disclosed system, medium priority alarms can range between 3 to 15 minutes before the onset of potential harm is critical. In certain embodiments, M1 alarms have the potential to be high priority alarms that require action within a short time, e.g., 2 minutes, and it may be necessary for primary care nurses to always address these. In certain embodiments, M2 and M3 alarms have the potential to become M1 alarms within 5 and 10 minutes, respectively. This allows ample time for these alarms to be responded in an alarm forwarding scheme to reduce alarm fatigue while maintaining patient safety.

In certain embodiments of the disclosed system, low priority alarms take 15 minutes or greater before non-serious patient harm can occur. In certain embodiments, L1 alarms will escalate if clinicians do not respond to them. For example, a battery alarm with 30 minutes of life remaining that is initially assigned an L1 sub-priority will need to escalate if the device is not plugged into wall power within 15 minutes to allow time for escalation to a medium sub-priority and resolution by the escalation staff member. In another example, an L2 sub-priority escalates to a L1 sub-priority alarm after 30 minutes or does not escalate at all.

In certain embodiments, each sub-priority is categorized as a clinical alarm or a technical alarm and ranked based on one or more of time criticality and risk to the patient. The phrase "technical alarm" includes system error alarms or device fault alarms that often require a device to be replaced, e.g., a failure of the device's internal mechanism such as a stalled motor, and alarms that require a service to be performed on an operational device, e.g., replace a sensor, plug in battery, etc.

An example of a clinical alarm is an air-in-line alarm from an infusion pump because a clinically trained staff member needs to manipulate the intravenous (IV) set to purge the air bubble before restarting the infusion. Some alarm conditions require both technical and clinical corrective actions. For example, replacing a medical device will require the technical corrective action of bringing a new device into the patient's room and the clinical corrective action of connecting the device to the patient and programming the device.

Assignments of Staff Roles to Sub-Priorities

The present disclosure assigns a staff role to each sub-priority. In certain embodiments, certain staff roles, e.g., S5, have the skills to respond to technical alarms while other roles, e.g., S1-S4, have the skills and training to handle both clinical and technical alarms. A staff role assigned to a sub-priority is determined to be capable of resolving alarm conditions having this assigned sub-priority as well as alarm conditions assigned lower-level sub-priorities. In certain embodiments, the same staff role may be assigned to one of more sub-priorities. In certain embodiments, different staff roles may be assigned to the same sub-priority of alarm from different types of medical devices. Table 4 is an exemplary embodiment of different staff roles assigned to sub-priorities based on the medical device.

TABLE 4

| \Sub-priority Medical device\ | H1 | H2 | H3 | M1 | M2 | M3 | L1 | L2 |
|---|---|---|---|---|---|---|---|---|
| infusion pump | S2 | S2 | S2 | S2 | S4 | S4 | S5 | S5 |
| Ventilator | S1 | S1 | S2 | S2 | S4 | S4 | S4 | S5 |
| device #3 | S1 | S1 | S2 | S2 | S2 | S4 | S4 | S5 |

In certain embodiments, an alarm has a unique escalation pathway. For example, a "low-battery" alarm is not initially a concern but will become a critical issue if the battery is allowed to become fully depleted. Table 5 is an exemplary escalation pathway for an infusion pump battery alarm. A battery alarm may be assigned a low sub-priority, e.g., L1, when there is 30 minutes of battery time left, escalated to a medium sub-priority, e.g., M2, when there are 15 minutes of life, and further escalated to a high sub-priority, e.g., H2, when there is 3 minutes left. The sub-priority conveys to the intended recipient how much time they have to respond to the alarm.

TABLE 5

| Remaining battery life (min, | Sub-priority |
|---|---|
| 30 | L1 |
| 15 | M2 |
| 3 | H2 |

The disclosed system reduces alarm fatigue since the primary care nurse, e.g., S2, is not responsible for responding to many sub-priorities of alerts unless escalated.

Escalation of Sub-Priorities

Escalation of an alert according to aspects of the present disclosure is adapted to the device issuing the alarm and the sub-priority of the alarm as defined by the dynamic attributes that affect it. An exemplary escalation pathway is shown in Table 6.

TABLE 6

| staff category | S4 | S4 | S2 | S2 | S3 | All |
|---|---|---|---|---|---|---|
| Priority | M3 | M2 | M1 | H3 | H2 | H1 |
| escalation period | 5 min | 5 min | 2 min | 2 min | 1 min | Requires immediate response |
| next higher | S3 | S2 (a) | S2 (a) | S2 (b) | S1 | n/a |

S2 primary clinician assigned to this patient
S3 back-up clinician assigned to this patient
S4 lower-level clinician assigned to this patient The alarm escalation scheme in this invention can be applied to all medical device alarms to provide the specificity required to allow clinicians and technicians to know how much time they have to address the alarm before it escalates in sub-priority. In certain embodiments, an alert that has escalated in sub-priority is sent to a different staff member. In certain embodiments, the escalated alert is kept with the same staff member, but their personal device is updated to reflect the escalated status.

In certain embodiments, H1 sub-priority alarms never escalate in sub-priority. In certain embodiments, the next two sub-priority alarms, e.g., H2 and H3, escalate in one and two minutes respectively. In certain embodiments, M1 sub-priority alarms escalate in two minutes while the next two lower priority medium alarms, e.g., M2 and M3, both escalate in five minutes if not responded to. In certain embodiments, L1 escalates in 15 minutes. In certain embodiments, the highest escalation class for medium and low sub-priority alarms is H2. In certain embodiments, H1 alarms are reserved for situations that require a true immediate response.

Assigning a Sub_Priority

FIG. 1 is an exemplary block diagram of an Alarm Management System 100, according to certain aspects of the present disclosure. In certain embodiments, an alarm unit 110 is a physical device located in a patient room with its own display 112 and means to interact with a patient, e.g., speaker, microphone, video surveillance camera, etc. In certain embodiments, the Alarm Management System 100 is implemented as a virtual device, e.g., on a hospital server, and the alert content information is sent to a clinician's personal device, e.g., mobile phone. In certain embodiments, the alarm unit 110 is integrated by the control unit of a medical device, for example the controller of an infusion pump. The Alarm Management Application 120 contains data and instructions stored in a memory (not visible in FIG. 1) of the alarm unit 110 that, when loaded into a processor (not visible in FIG. 1) of the alarm unit 110 and executed, cause the processor to implement the functions described herein.

In certain embodiments, the Alarm Management Application 120 is communicatively coupled to a number of third-party, hospital-based systems. For example, the Alarm Management Application 120 will integrate with one or more of a Staff Management system 150, a Patient Registration system 148, an EMR system 142, a Lab system 144, and a Pharmacy system 146 that may include a Medical Administration Record (MAR). The Alarm Management Application 120 communicates information bidirectionally with these systems through a HL7 integration engine 140 ensuring that data from the hospital-based systems is translated appropriately for the Alarm Management Application 120 and vice versa.

The Alarm Management Application 120 communicates bidirectionally with a plurality of medical devices that alarm as exemplified by Medical Device 132, e.g., infusion pump, patient monitor, ventilator, etc. In the example of FIG. 1, this communication occurs through an integration engine 130 that translates the alarm information from these devices into a standard format for the Alarm Management Application 120. In certain embodiments, the Alarm Management Application 120 is connected to these other devices via a wired connection and a standard communication protocol, e.g., RS-232, RS-485, etc. In certain embodiments, a portion of the connection is wireless using one of the common medical device communication technologies, e.g., Wi-Fi. In certain embodiments, the Alarm Management Application 120 will also communicate with a Vital Sign Monitor 134. These physiological monitors provide information that is useful for determining the status of the patient and how the patient is responding to their treatment.

In certain embodiments, the Alarm Management Application 120 is also communicatively coupled to a communication network 160, which may include wired or wireless connections to various personal devices and other databases, and to a Real Time Locating System 162 (RTLS) that is capable of determining the physical location of a staff member; e.g., whether a staff member is in a patient room. In certain embodiments, the Alarm Management Application 120 is integrated into a third-party hospital enterprise system and the logic described in the present disclosure replaces the enterprise software's alarm management functionality.

In certain embodiments, the database 123 aggregates information related to the patient specific, device specific, and time dependent dynamic attributes. In certain embodiments, the database 123 includes information and rules regarding the alarms that are implemented in each connected Medical Device 132 and Vital Sign Monitor 134. This information includes the causes of the alarms, how the causes may be resolved, and the verbal commands the Alarm Management Application 120 can provide to a patient to resolve an alarm.

In certain embodiments, the database contains the medications and fluids being administered by a treatment device, e.g., an infusion pump, and medication administration information, e.g., the administered doses and times of administration, and the medical devices being used. This information may include PK properties, e.g., biological half-life, as well as whether an infusion is a loading dose, or a maintenance dose as determined by one or more of the doctor's orders and medical device settings. This information may also include PD characteristics, e.g., whether the medication or fluid is known or intended to affect a patient health measurement, e.g., vital sign or lab test of the patient.

In certain embodiments, the database 123 mirrors patient-related data available from one or more of the external systems, e.g., the EMR 142, the Lab 144, the Pharmacy 146, and the Registration 148. In certain embodiments, the Alarm Management Application 120 retrieves information on the patient such as their age and weight from the Registration system 148 so as to customize the sub-priority alarm criteria for that patient. For example, an alarm associated with an infusion pump stopping fluid replacement in a dehydrated adult may require less urgency than an alarm associated with an infusion pump stopping fluid replacement in dehydrated neonates or pediatrics under a certain weight. Where an H2 alarm may be appropriate for the adult with dehydration, an H1 alarm may be the preferred sub-priority alarm for the dehydrated neonate or pediatric under a certain weight.

In certain embodiments, information about the patient from the Device Integration Engine 130 is drawn into a Patient health assessment module 121 that is configured to execute an assessment protocol that combines various measurements and/or assessments to generate a "health rating" that can then be transferred to the Alarm Priority function 122 for use in assigning a sub-priority. In certain embodiments, the protocol may be one or more of the MEWS, which is a tool designed to identify patients with declining conditions, and APACHE 2, a widely used intensive care unit (ICU) mortality prediction tool.

In certain embodiments, the Alarm Management Application 120 utilizes a nationally known patient health assessment 121, or algorithms customized by the individual hospital, to dynamically adjust the sub-priority assigned to an alarm. Two such algorithms are the MEWS and the National Early Warning Score (NEWS) algorithms, which assign a scope to certain vital signs based on a comparison to respective thresholds, wherein higher scores area associated with poorer prognosis. These algorithms are used to triage patients in a lower acuity setting and determine the need for a rapid response team to intervene. In certain embodiments, the Alarm Management Application 120 calculates the algorithm score based on vital signs received from a Vital Sign Monitor 134 and dynamically adjusts the sub-priority of an alarm related to a medication or fluid that may improve the patient's deteriorating condition. For example, if a patient is experiencing decline in several parameters that may indicate the onset of sepsis and the patient is receiving fluid replacement therapy or an antibiotic, then the Alarm Management Application 120 may increase the sub-priority of an "infusion stopped" alarm by one or two levels.

When an alarm is received from a Medical Device 132, the Alarm Priority module 122 determines the sub-priority for the alarm condition based in part on one or more dynamic attributes, for example information received from the Vital S1gn Monitor 134 and information retrieved from one or more of the EMR 142, the Lab system 144, the Pharmacy system 146, and the Registration system 148 as well as information, e.g., medication, from the database 123. The Alarm Priority module 122 determination may also be based in part on alarm information and rules retrieved from the database 123.

Once the sub-priority is assigned to the alarm, the Alarm Priority functionality 122 sends the information to the Alarm Distribution functionality 125. The Staff Role functionality 124 will retrieve the current shift's clinicians and staff/ technicians from the hospital's Staff Management system 150, associate the available staff members with defined staff roles, and send this information to the Alarm Distribution functionality 125. The Alarm Distribution functionality 125 will combine the sub-priority with the appropriate staff role, identify the clinician or technician associated with the role and assigned to the patient, and send the sub-priority and role and staff member identification to the Alarm Handler 126.

In certain embodiments, the Alarm Handler 126 will determine from the RTLS 162 if there is an assigned clinician or technician is in the patient room. In certain embodiments, if a staff member is not in the room, then the Alarm Handler module 126 provides an alert to the staff member associated with the staff role assigned to the sub-priority through the network to one or more of the staff member's personal devices.

In certain embodiments, the Alarm Management System 100 comprises a second application (not shown in FIG. 1) that is installed locally on the personal device. In certain embodiments, a set of specific escalation rules, e.g., rules governing how much time before one sub-priority escalates to another, rules associated with how dynamic attributes are applied across a user population, etc., for this patient are downloaded onto the personal device and the local app can execute escalation of a received alert per the downloaded rules. In certain embodiments, updates to the specific escalation rules are periodically downloaded to the personal device. n certain embodiments, the Alarm Unit 110 includes a display 112, a microphone 114, an audio annunciator 116, e.g., a speaker or a buzzer, and a video surveillance camera 118. In certain embodiments, the Alarm Handler functionality 126 will provide one or more of a visual alert on the display 112 or an audio alert on the annunciator 116 according to information received from the Alarm Distribution module 125. In certain embodiments, a microphone or video surveillance camera is used to detect patient actions that assist the Alarm Management Application 120 to verify the presence or the lack of presence of a particular cause of an alarm to help determine the appropriate sub-priority or to determine the alarm can be suppressed, e.g., a false positive alarm that does not need to be conveyed to the intended recipient.

The Registration system 148 may disclose that the patient has a Do Not Resuscitate (DNR) order. In certain embodiments, sub-priority assignment rules in the Alarm Priority functionality 122 determine alarms for patients with a DNR order are assigned lower sub-priorities that the same alarms for patients without a DNR order. For example, an H1 sub-priority will be changed to H2, a H2 sub-priority to H3, etc. In certain embodiments, only the highest sub-priority, e.g., H1, will be reduced and all other assigned sub-priorities remain at the standard level.

In certain embodiments, the escalation rules are different when a clinician is in the patient room. In certain embodiments, the Alarm Distribution module 126 communicates to the Medical Device 132 and causes the Medical Device 132 to emit or silence the alarm. In certain embodiments, every alert for all alarms will cause an alert in the patient's room, either from the Alarm Unit 110 or the Medical Device 132, after a defined amount of time.

Alert Content

The method disclosed herein enhances the ability of a staff member to determine the urgency of responding to an alarm and the amount of delay time they may have before responding to an alarm.

In certain embodiments, the content provided to a personal device or for the display screen for an in-room Alarm Management System for an original alert includes one or more of the following: the original sub-priority, the time remaining until the sub-priority is escalated, the identification, e.g., initials, of the staff member to whom the alarm will be escalated, the highest sub priority that is associated with the escalation staff member, whether a back-up is available for the escalation staff member, and a corrective action or recommendation based on a dynamic attribute that may be useful to the recipient. For example, if a dynamic attribute indicates a critical arrhythmia exists and the patient is on a medication that is known to cause the arrhythmia, then the alert includes information that a medication with potential adverse effects to the present condition is being administered to the patient.

For an escalated alert, additional information includes the original sub-priority juxtaposed with escalated sub-priority, e.g., M1/H3, and the time since the alarm was received. Inclusion of the original sub-priority in an escalated alert informs the recipient of the severity of the original alarm and helps staff members determine how to triage concurrent alarms from different patients.

In certain embodiments, wherein an alert is being sent to a staff member who has previously been assigned alarms that are not yet resolved, i.e., active alarms, the new alert comprises a ranking of all alerts associated with active alarms that are assigned to the staff member. In certain embodiments, the ranking is based in part on current sub-priorities assigned to the previously assigned alarms. In certain embodiments, the ranking is based in part on a dynamic attribute of the previously assigned alarms. For example, the selected staff member may be closer to the medical device associated with the new alarm that any other staff member. In certain embodiments, the new alert comprises a notification that at least one of the prior alerts has been re-assigned to another staff member.

Figure 2A:
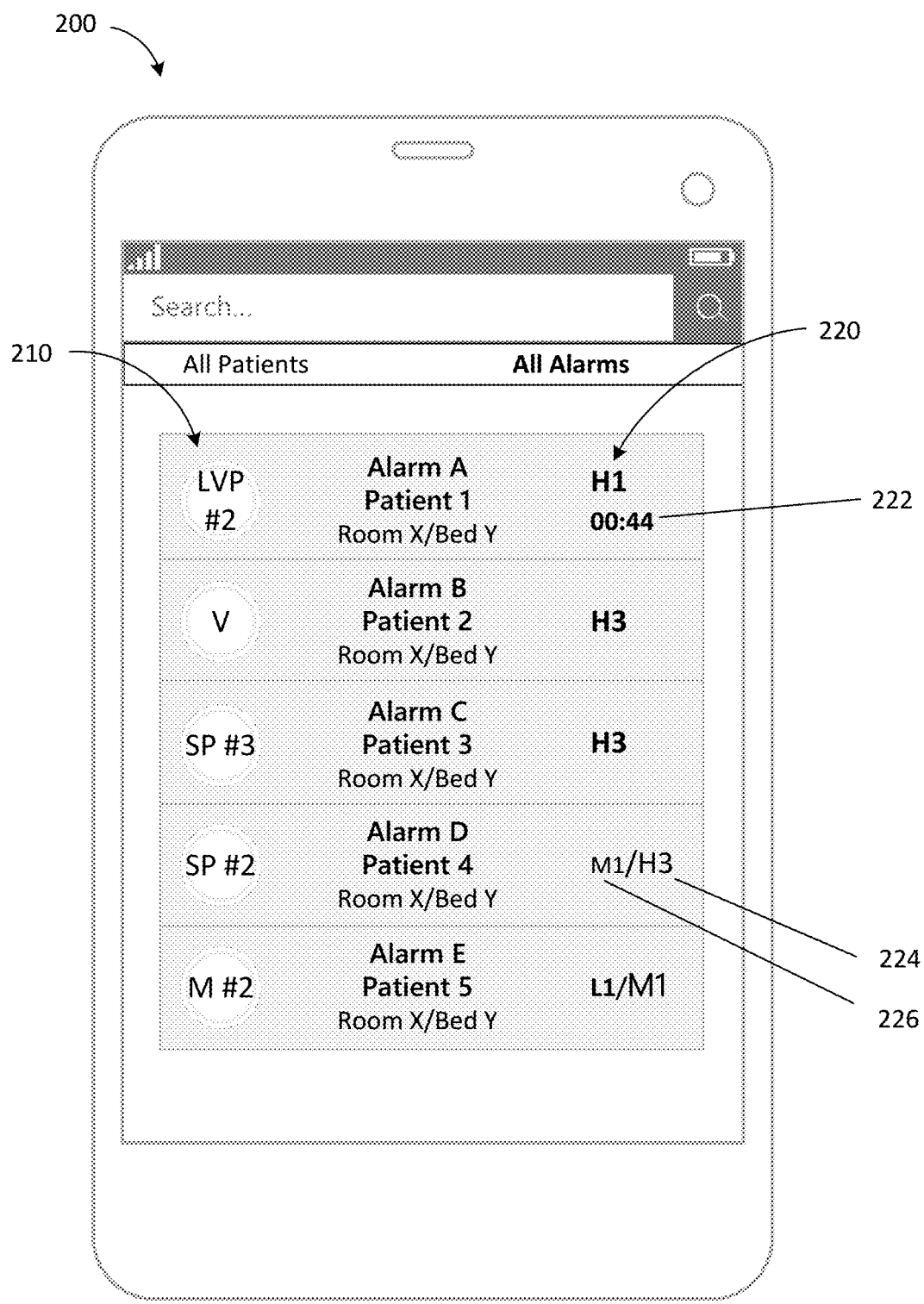
FIGS. 2A and 2B are exemplary embodiments of alerts provided on a staff member's personal device, according to certain aspects of the present disclosure.
Figure 2B:
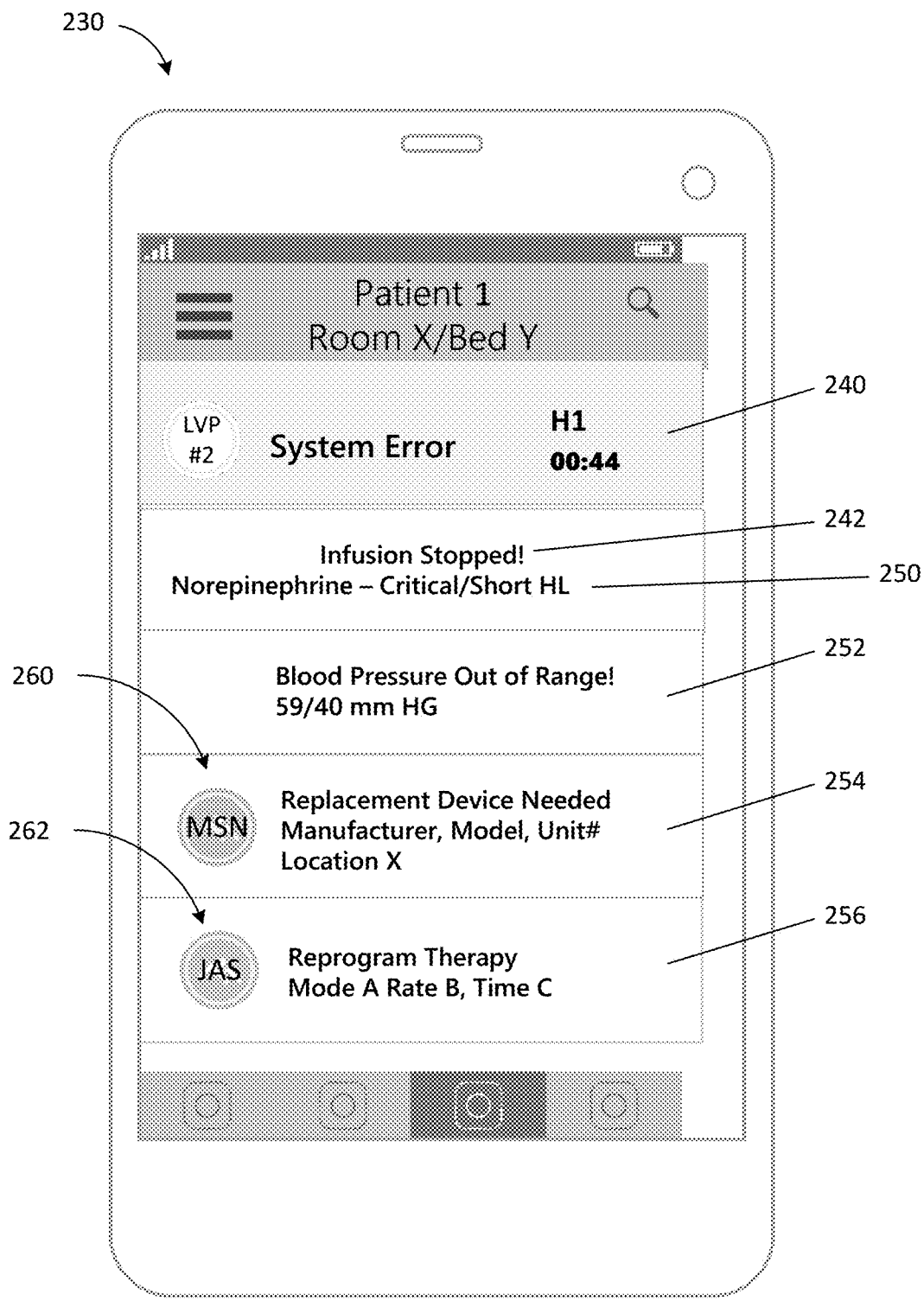

FIGS. 2A and 2B are an exemplary embodiment of a method of providing a first alert to a first staff member's personal device based in part on a dynamic attribute of a patient. In certain embodiments, the visual display of the information depicted FIGS. 2A and 2B is information that can also be conveyed on a display 112 of the Alarm Management System 100 located in a patient's room.

FIG. 2A depicts an exemplary display 200 of a list of alarms on the personal device of a staff member. On the left-hand side is the device identification information 210, e.g., LVP— large volume pump, V— ventilator, SP— syringe pump, and M— monitor. In the middle of each alarm entry is the alarm display name, and patient identification information, e.g., name, room, bed, etc. On the right-hand side of each entry is the sub-priority or sub-priorities 220. The sub-priority information contains either the sub-priority or the original (i.e. before escalation) sub-priority 226 juxtaposed with the escalated current sub-priority 224. For example, the Alarm E started as a L1 sub-priority alarm and has escalated several times and is now a M1 sub-priority.

In certain embodiments, the alarms are listed in order of importance with the alarms associated with the highest sub-priority 20 listed first, e.g., H1. In certain embodiments, ventilator alarms will be displayed first. In other embodiments, patient monitor alarms associated with a critical arrhythmia will be displayed next especially if there is a current treatment, e.g., medication infusion, that may be causing the arrhythmia. In other embodiments, infusion pump alarms will be displayed after ventilators alarms and critical arrhythmia alarms but will otherwise be displayed before monitor alarms. In the example of FIG. 2A, Alarm B associated with a H3 ventilator alarm is displayed before Alarm C, a H3 syringe pump alarm. In certain embodiments, the original sub-priority of two alarms are compared and the alarm associated with the higher original sub-priority alarm is displayed first. In FIG. 2A, Alarms C and D are both currently H3 alarms, however Alarm C has the higher original sub-priority and is displayed first.

FIG. 2B provides an exemplary display 230 of expanded information for one of the alarms of FIG. 2A, the system error alarm 240 for a large volume pump with a H1 sub-priority. The alarm content shows both the dynamic attributes associated with the alarm and corrective actions associated with the dynamic attributes. For example, the display provides 1) dynamic attribute 242—a medical device factor that the infusion has stopped, 2) dynamic attribute 250-a medication factor that the medication has a critical indication-for-use, and 3) dynamic attribute 252—a patient monitor factor that a patient health measurement, e.g., blood pressure, affected by the medication is out of its range, e.g., 59/40 is a very low blood pressure. The display 230 includes two corrective actions: the first action 254 is retrieve a new pump with the pump ID and location information provided. The initials 260 identify the staff member assigned to execute this action. The second corrective action 256 is for the clinician 262, "JAS," to reprogram the pump and provides the reprogram instructions.

Table 7 illustrates an exemplary alert content.

TABLE 7

| | Initial alarm | Escalated Alarm |
|---|---|---|
| Alert Recipient | Primary Nurse - MJK | Primary Nurse - MJK |
| Current sub-priority | H3 | H3/H2 |
| Next sub-priority | H2 | H1 |
| time remaining to escalation | 2 min | 1 min |
| Expected Escalated Person | Back-up nurse - LSM | Back-up nurse - LSM |
| Escalated Person's highest sub-priority alarm | M1 | H1 |
| Back up available? | Yes | No |

Table 7 juxtaposes information from an initial alarm and an escalated alarm and shows how a change in time affects how the alert conveys information and how the availability of a backup may change. The initial alarm is sent the primary nurse with the initials MJK as a H3 sub-priority alert. In certain embodiments, the time to escalate between a H3 to H2 alarm takes 2 minutes. In certain embodiments the primary nurse has the option to send this alarm to the back-up nurse, having the initials of "LSM," since the highest sub-priority of the back-up nurse is M1.

For the alert that shows the escalated alarm, the sub-priority would show as H3/H2 where the H3 was the original sub-priority and the H2 is the current and escalated sub-priority. The time before escalation from an H2 to an H1 sub-priority alarm is one minute. During the time it took for the H3 alarm to escalate to an H2 alarm, e.g., two minutes, the back-up nurse with the initials LSM received an H1 sub-priority and is not available as a back-up since they have a more urgent alarm to respond to. In certain embodiments, the back-up staff member will not be available. In other embodiments, if the back-up nurse "LSM" was not available then the Alarm Management Application 120 would show the availability of another back-up staff member who is available.

Infusion Pump Alarms

Figure 3A:
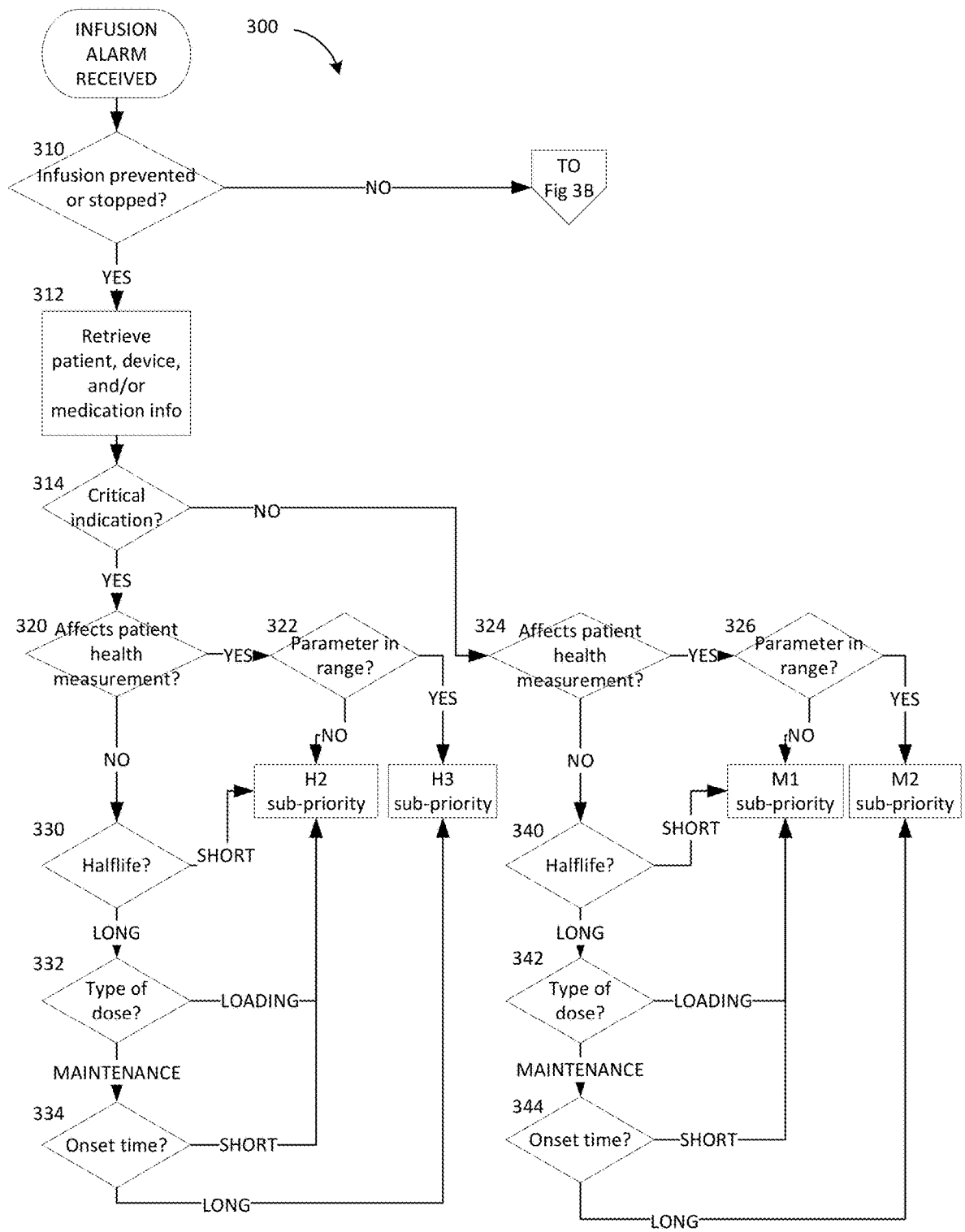
FIGS. 3A and 3B depict a flowchart of an exemplary embodiment of a method of assigning a priority and sub-priority to an alarm received from an infusion pump, according to certain aspects of the present disclosure.
Figure 3B:
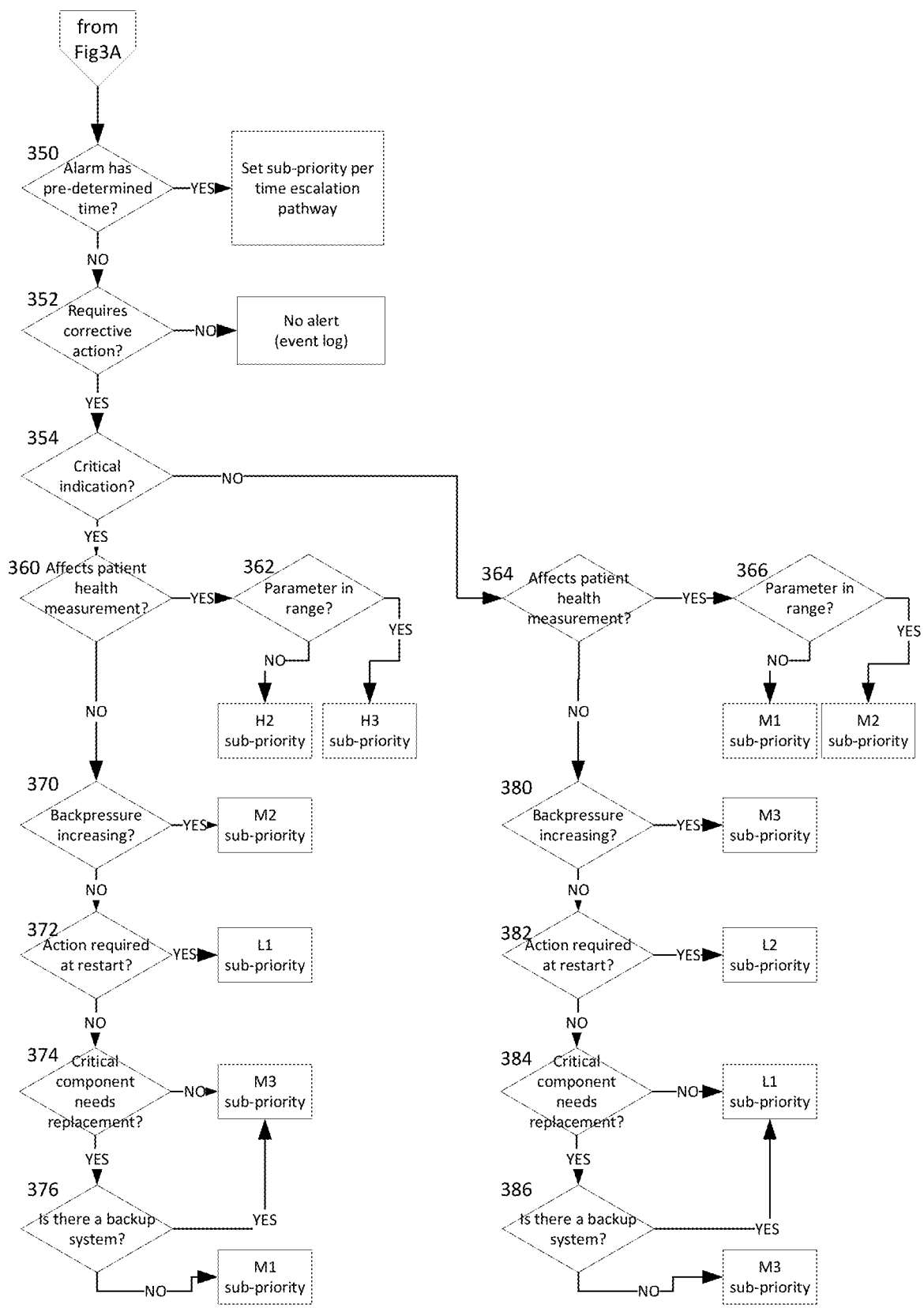

FIGS. 3A and 3B depict a flowchart 300 of an exemplary embodiment of a method of assigning a sub-priority to an alarm received from an infusion pump, according to certain aspects of the present disclosure. The process starts in FIG. 3A when an alarm is received from an infusion pump. The process branches in step 310 to FIG. 3B if the alarm is not associated with the pump being stopped or a condition that prevents an infusion from starting or continuing, otherwise proceeding to step 312.

Step 312 retrieves one or more of patient information, medication information, and device information for sources as described with respect to FIG. 1. Step 314 branches based on whether any of the medications are being administered to the patient with a critical indication for use or a non-critical indication for use.

In this example, the indication for use of the medication is the main factor that determines the initial priority category, e.g., H or M, for each alarm associated with an infusion pump. Medication or fluids with critical indications for use are high priority, e.g., H, and medications and fluids with non-critical indication for use are a lower priority, e.g., M. However, most medications have more than one indication for use and many medications have indications for use that are either critical or non-critical. For example, norepinephrine is used to treat acute hypotension, cardiac arrest or sepsis and they are all considered high critical indications for use, therefore any alarm associated with norepinephrine will be high priority, e.g., H1 or H2. On the other hand, hydrocortisone is high priority, e.g., H2, when used to treat status asthmaticus (severe acute asthma that requires immediate recognition and treatment) and medium priority, e.g., M2, when used to treat inflammation.

When a prescribed medication has multiple different indications for use, in certain embodiments, the Alarm Management Application 120 described in FIG. 1 will capture indication for use applicable to the patient from the EMR 142. In certain embodiments the application will retrieve this information from internal database 123. In certain embodiments, if there are several indications for use with different risk profiles, the Alarm Management Application 120 will prompt the clinician to choose which indication for use is associated with the prescribed medication or fluid.

Steps 320 and 324 each branch based on whether any of the medications are being administered to the patient are known to influence a patient health measurement such as a vital sign or lab value.

In certain embodiments, if the path branches from step 320 to step 322 for a medication or fluid with a critical indication of use, the process assigns a higher sub-priority, e.g., H2, if a vital sign or lab is out of a pre-determined range since the pump stoppage of this critical medication indicated to improve the patient health measurement would only worsen the situation. A lower sub-priority, e.g., H3 or M1, is assigned if the patient health measurement is within its respective pre-determined range.

For example, vasopressors are used to treat low blood pressure. If a vasopressor is infusing and the patient's blood pressure is being actively monitored, an alarm related to the vasopressor that occurs while the patient's blood pressure is below the acceptable range should be assigned a sub-priority, e.g., H2. If the blood pressure changes from below-range to within the acceptable range, then the sub-priority of that alarm may be reduced, e.g., H3. If the patient's blood pressure is above the acceptable range, then a lower sub-priority, e.g., M1 may be appropriate since the alarms associated with FIG. 3A are alarms that stop the therapy. In certain embodiments, if the blood pressure rises above an acceptable range and the vasopressor is still infusing then a high sub-priority alert is issued, e.g., H2 or H3, as shown in FIG. 3B. Lastly, if the patient being infused a vasopressor but the patient's blood pressure is not being actively monitored, then the sub-priority for any alarm related to the infusion of the vasopressor could be H1, H2 or H3 depending on the other dynamic attributes.

Medication and fluids may also be used to improve lab results. Lab values may start off normal and monitoring is ordered to ensure infusion of a medication or fluid does not change the lab result to an abnormal value. In other circumstances, the initial lab value may be outside the acceptable range and a medication or fluid is administered to improve it. For example, potassium IV may be administered to treat hypokalemia. An alarm related to the infusion of the potassium IV may be assigned an H2 sub-priority if the lab value is outside the acceptable range and assigned a lower sub-priority, e.g., H3 or M1, if the lab result is within the acceptable range.

Steps 330, 332, 334 are exemplary evaluations of PK/PD characteristics of a medication being administered to the patient. If any of the characteristics is of immediate concern, e.g., a short half-life, a loading dose, or a short onset period, the process assigns the highest sub-priority, e.g., H2. If all of the characteristics are not of immediate concern, e.g., a long half-life and a maintenance dose and a long onset period, the process assigns a lower sub-priority, e.g., H3.

In certain embodiments, Step 314 branches to Step 324 if the alarm is associated with a medication or fluid with a non-critical indication of use. If the path branches from step 324 to step 326, the process assigns a first sub-priority, e.g., M1, if a vital sign or lab is out of a pre-determined range and assigned a lower sub-priority, e.g., M2, if all vital signs and labs are within their respective pre-determined ranges.

Steps 340, 342, 344 replicate steps 330, 332, 334 in evaluating the PK/PD characteristics of a medication being administer to the patient for a medication with a non-critical indication for use. Steps 340, 342, 344 assign sub-priority M1 if any of the characteristics is of immediate concern and assign sub-priority M2 if all of the characteristics are not of immediate concern.

Picking up the process in FIG. 3B that branched from step 310 of FIG. 3A, step 350 checks whether the alarm is associated with a special time-related alarm, for example the battery alarm described with respect to Table 4. If associated with a battery alarm, then the sub-priority will be based on the amount of time remaining on the battery, otherwise step 352 checks whether the alarm is a notification that does not require correct action. Certain alarms do not require corrective action. For example, some infusion pumps have an internal mechanism that tries to self-correct an occlusion for 60-120 seconds. If the pump issues an alarm at the start of the self-correction process, the disclosed system waits in step 350 for the defined corrective period. If the pump correction is successful, the pump may issue an "alarm" that is simply a signal that the issue has been automatically resolved and then step 352 logs the event and terminates the process.

If the pump alarm is not associated with a time dependent alarm and a corrective action is required, then the process continues to step 354 where it branches depending on whether the alarm is related to a critical indication of an administered medication. If a medication being administered has a critical indication for use, then step 354 branches to step 360 and further branches depending on whether the medication is known to have an effect on a patient health measurement such as a vital sign or laboratory test. In certain embodiments, if the path branches from step 360 to step 362, the process assigns a higher sub-priority, e.g., H2, if a vital sign or lab is out of a pre-determined range and assigned a lower sub-priority, e.g., H3 or M1, if all vital signs and labs are within their respective pre-determined ranges.

Steps 370, 372, 374 are exemplary evaluations of operational characteristics of the infusion pump being used to treat the patient. Each operational characteristic will have an associated criteria and an assigned sub-priority if that criterion is met. For an example of backpressure of an infusion line, an increasing backpressure is assigned an M2 sub-priority in step 370 while a constant backpressure (normal operation) will cause the process to branch to step 372 to consider other operational characteristics. In this example, if an action is required at restart of the pump, the process will assign an L1 sub-priority, otherwise proceed to step 374 that assigned an M1 priority if a critical component needs to be replaced and there is no back-up system and otherwise assigns a M3 priority.

In certain embodiments, if the path branches from step 354 to step 364 for a medication or fluid with a non-critical indication for use, the process assigns a first sub priority, e.g., M1, if a patient health measurement is out of a pre-determined range and assigned a lower sub priority, e.g., M2, if all patient health measurements are within their respective pre-determined ranges.

Steps 380, 382, 384 replicate steps 370, 372, 374 in evaluating the operational characteristics of the infusion pump being used to treat the patient with a medication or fluid with a non-critical indication for use. In general, the assigned priorities for each of the respective conditions will be lower when the medication or fluid is associated with a non-critical indication for use.

An example of a "routine" alarm is a near-end-of-infusion alarm from an infusion pump, which may indicate that there are 10 minutes remaining in the present infusion. The required corrective action is to obtain and connect a new IV bag, or a pre-filled syringe, of the medication to enable the next infusion to start. In certain embodiments, the initial sub-priority is set to a low level, e.g., M3, which will cause the system to notify a S3 clinician to retrieve the new IV bag and bring it to the patient's room. The alert to the S3 clinician may include the sub-priority, the necessary information to describe the item to be retrieved, e.g., the size of the IV bag and the medication concentration and volume. Even when the S3 staff member acknowledges the alert, the alarm is escalated to a higher priority, e.g., a M1, to notify the assigned S1 staff member to come to the patient room to connect the new IV bag and start the new infusion.

Multiple Infusions

A lot of patients that are hospitalized have multiple diagnoses that require infusions and often each diagnosis requires multiple infusions. In severe cases, patients may have 10 or more active infusions. For each separate infusion, the Alarm Management Application 120 will determine if the indication for use is critical or non-critical. In certain embodiments, the Alarm Management Application 120 will retrieve the indication for use from the database for each infusion. In certain embodiments, the application will determine the indication for use from the diagnoses that requires infusion from the EMR system 142. In certain embodiments, the Software Management App 120 will ask the clinician to identify the applicable indication for use if the medication has indications for use that are both critical and non-critical. In certain embodiments, the Alarm Management Application 120 will then determine if medications or fluids that have non-critical indications for use are codependent with medications or fluids that have critical indications for use. If yes, then the medication or fluid with the non-critical indications for use will take on the sub-priority alarm of the medication or fluid with the critical indication for use. For example, a patient who is hyperglycemic and receiving insulin, which has a critical indication for use, may be co-infused with low-concentration dextrose, which has a non-critical indication for use. In this situation, if an alarm occurs with the low-concentration dextrose solution, a sub-priority will be assigned using the rules defined for insulin.

Escalation and Silencing an Alarm

Figure 4:
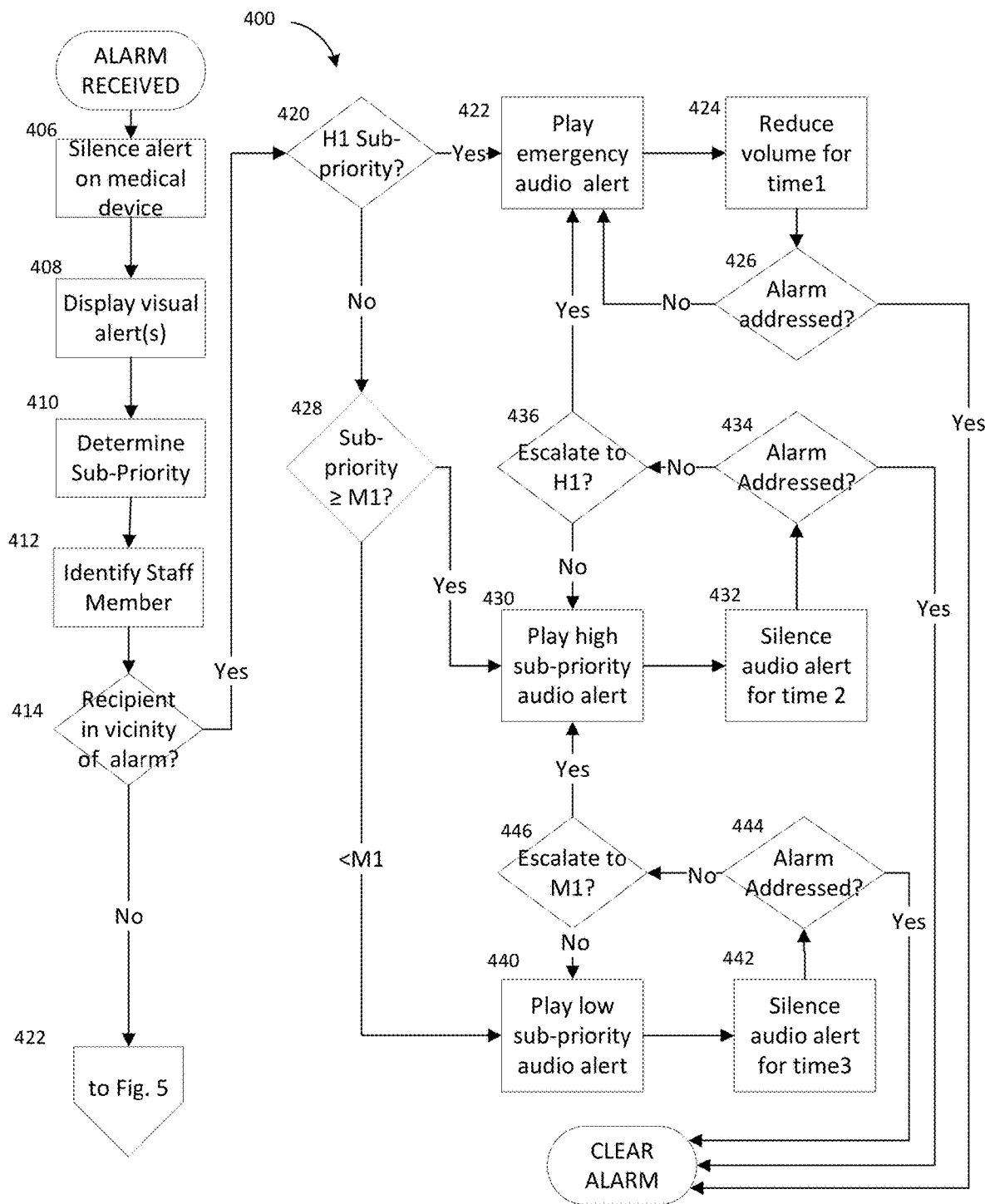
FIG. 4 is a flowchart of an exemplary embodiment of a method of silencing a bedside alarm, according to certain aspects of the present disclosure.

FIG. 4 is a flowchart 400 of an exemplary embodiment of a method of announcing and silencing a bedside alarm, according to certain aspects of the present disclosure. In certain embodiments, only the highest sub-priorities need to generate an audio alert.

The process starts with receipt of an alarm from a medical device located in the patient's room. In many cases, the medical device will emit an audible alert at the time of sending the alarm. The Alarm Management Application 120 sends commands to the medical device that issued the alarm in step 406 to silence the audio alert and to display the visual alert in step 408, which may also cause visual alerts to be displayed on the display 112 of the Alarm Management Application 120 and the personal devices of the intended recipients. In certain embodiments, a bidirectional protocol via a wired or wireless connection communicates the instructions to the device to silence its alarm. In other embodiments, the volume for the medical device may be turned to "off" or to its lowest setting and the audio alerts will be generated by the Alarm Management Application 120.

The alarm is assigned a sub-priority, for example using the process defined in FIGS. 6A-6E, in step 410 and the first staff member is identified in step 412. Step 414 determines whether the identified staff member is in the patient room, for example using information received from the RTLS system 162 of FIG. 1. If the staff member is not in the patient room, the process continues to FIG. 5. If the staff member is in the room, the process branches to step 420. Step 420 checks whether the present sub-priority is H1, in which case the process branches to step 422 to sound the emergency audio alert in the room. Note that in certain embodiments, steps 422, 430, and 440 include providing an alert to a staff member. In certain embodiments, if a clinician silences an H1 alarm, the volume of the alert is reduced for a certain amount of time "time1" in step 424 after which the process proceeds to step 426, which monitors the time elapsed since the alarm was received and determines whether the alarm has been resolved. If the alarm is resolved, the alarm is cleared, and the process is terminated. If time1 expires and the alarm is not resolved, the process returns to step 422 and repeats the emergency alert with a volume that matches or exceeds the original alert. In certain embodiments, an H1 sub-priority alarm cannot be silenced.

If the sub-priority was less than H1 in step 420, the process branches to step 428. If the sub-priority is greater than or equal to M1, the process branches to step 430, wherein the Alarm Management System 120 plays the "high" sub-priority alert. After a pre-determined amount of time elapses or if a clinician silences the alarm, the alert is silenced for a certain amount of time "time2" in step 432 after which the process proceeds to step 434 that monitors the time elapsed since the alarm was received and determines whether the alarm has been resolved. If the alarm is resolved, the alarm is cleared, and the process is terminated. If time2 expires and the alarm is not resolved, the process branches to Step 436 and determines if the alarm has escalated, for example per the workflow of FIG. 5, to an H1 sub-priority. If yes, then the process branches to Step 422, otherwise the process returns to step 430.

If the sub-priority was less than M1 in step 428, the process branches to step 440 that plays the "low" sub-priority alert. In certain embodiments, the low sub-priority audio alert may be silence and only a visual alert is provided in the room. After a pre-determined amount of time elapses or if a clinician silences the alarm, the alert is silenced for a certain amount of time "time3" in step 442 after which the process proceeds to step 444 that monitors the time elapsed since the alarm was received and determines whether the alarm has been resolved. If the alarm is resolved, the alarm is cleared, and the process is terminated. If time3 expires and the alarm is not resolved, the process returns to step 446, which escalates the sub-priority. If the sub-priority is now M1, the process branches to step 432 otherwise returns to step 440.

Table 8 provides an exemplary set of rules for whether an alarm is silenced or sounds in a patient room. In certain embodiments, only the highest sub-priority alarm sounds if it is known that no clinician is in the room. In certain embodiments, only the highest sub-priorities, e.g., H1, H2, and H3, play an audio alert as soon as the alarm condition occurs when the intended recipient is in the room. In other embodiments, the lower sub-priority alarms, e.g., M1-L3, only play an audio alert after a pre-defined delay after the alarm condition occurs when the intended recipient is in the room. In these situations, the visual alert associated with the alarm condition displays on the Alarm Management System's display 112 and the in the display of the device itself. In other embodiments, the hospital can configure which sub-priorities play an audio alert with a delay or without a delay as shown for the M1 sub-priority in Table 8.

cation 120 to a remote staff member's personal device. If the assigned sub-priority is H1, step 512 branches to step 514 that sends an alert to the identified staff member assigned to the patient for an H1 sub-priority. Step 516 determines if the alarm is resolved in a defined amount of time 4 and if not plays an emergency audio alert in the patient's room in Step 518 and sends the alert in step 520 to the entire clinician team on the floor or assigned to the patient. In certain embodiments, only a sub-priority of H3 or higher when escalated to an H1 sub-priority will play the emergency audio alert in the patient's room when no clinician is available. Step 522 determines if the alarm is resolved in delay time 5, and if not, it continues to generate the emergency audio alert in step 518. In some embodiments, the volume of the emergency audio alert increases to its maximum volume. If the alarm is resolved within delay time 4 in step 516, or delay time 5 in step 522, then the alarm is cleared.

If the assigned sub-priority is not H1, then the process proceeds to step 524. If the assigned sub-priority is H2, step 524 branches to step 526 that sends an alert to the staff member assigned to the staff role associated with the present sub-priority and proceeds to step 528. In step 528, the software determines if the alarm has been resolved within the specified delay time. If the alarm is resolved, step 528 clears the alarm, and the process is terminated. If time 6 expires and the alarm is not resolved, the process branches to step 530, wherein the sub-priority is escalated to H1 and the process proceeds to step 532 where the Alarm Management Application 120 identifies the staff member. In certain embodiments this staff member is the same person who received the H2 sub-priority alert. In other embodiments, it is a new staff member, e.g., back-up clinician. Once the staff

TABLE 8

| Sub-priority | Escalation Times to Next Sub-Priority | Escalation Class | In-room Audio Alert When No Clinician in Room | In-room Audio Alert When Clinician is in Room |
|---|---|---|---|---|
| H1 | NA (highest) | highest | Yes (30 second delay) | Yes |
| H2 | 1 min | H1 | No | Yes |
| H3 | 2 min | H2 | No | Yes |
| M1 | 2 min | H3 | No | Yes/On a Defied Delay |
| M2 | 5 min | M1 | No | On a Defined Delay |
| M3 | 5 min | M2 | No | On a Defined Delay |
| L1 | 15 min | M3 | No | On a Defined Delay |
| L2 | 15 min | N/A | No | On a Defined Delay |

In this disclosure, silencing of medical device alarms takes a risk-based approach that considers the urgency of responding to alarm to prevent serious injury or death by determining what dynamic attributes of the patient are critical to consider. The consideration of the patient specific, device specific and time specific dynamic attributes provides the specificity that ensures only the alarms associated with the highest sub-priority, e.g., H1, need to have the audio component present at the bedside when a clinician is not in a room. All other alarms with lower sub-priorities may have their audible components turned off until they escalate to an H1 sub-priority.

Figure 5:
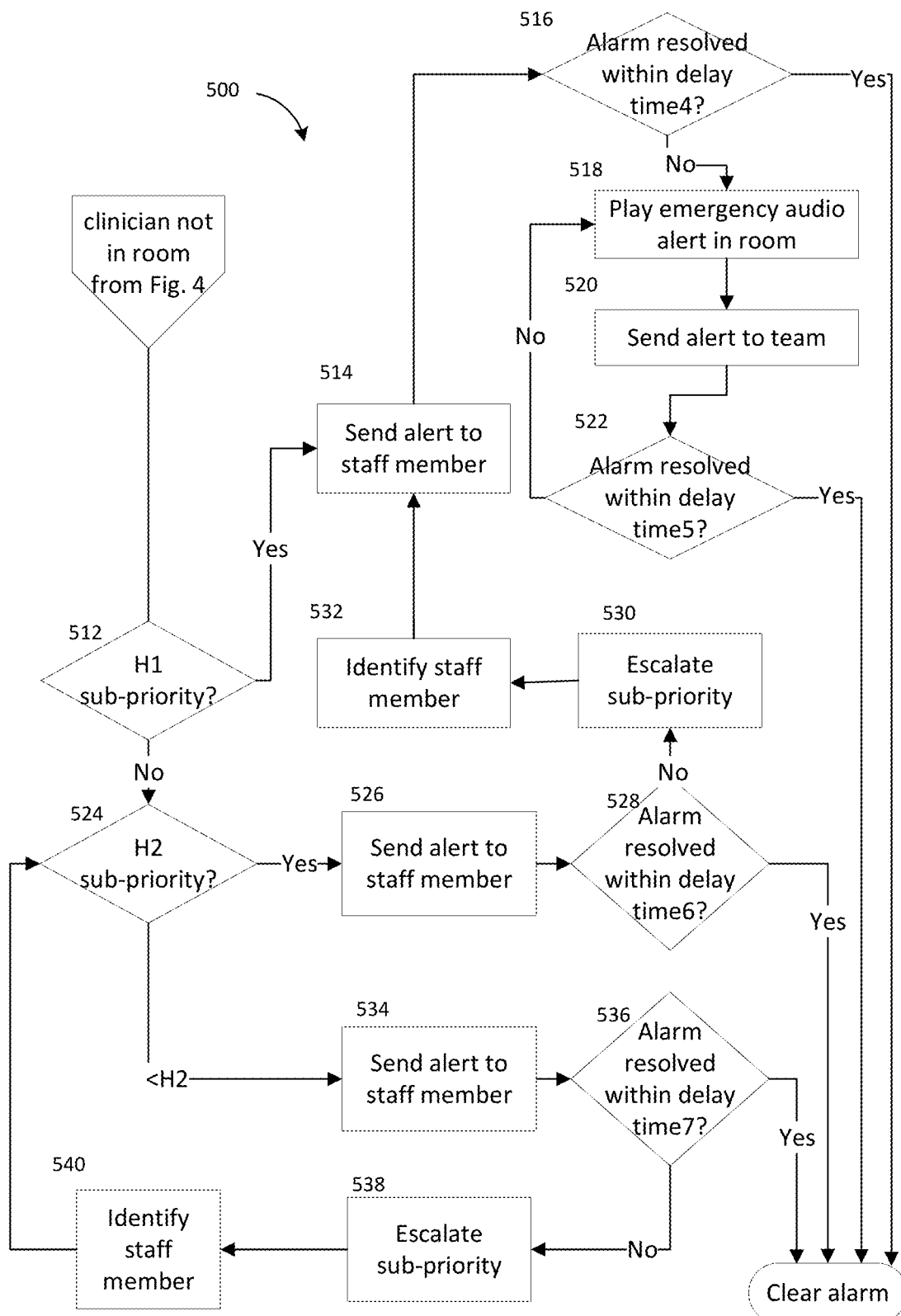
FIG. 5 is a flowchart of an exemplary embodiment of a method of escalating an alarm, according to certain aspects of the present disclosure.

FIG. 5 is a flowchart 500 of an exemplary embodiment of a method of escalating an alert in an alarm-forwarding scheme and playing an audio alert in the patient's room based on a risk threshold when a staff member is not in the room, according to certain aspects of the present disclosure.

The process starts with step 512, a continuation from FIG. 4 after the alert is sent from the Alarm Management Applimember is identified the H1 sub-priority is conveyed on the staff member's personal device at Step 514 and the steps for the H1 sub-priority process are completed.

If the sub-priority is initially less than H2, then an alert is sent to the identified staff member in step 534. If the alarm is resolved within time 7, step 540 clears the alarm and the process is terminated. If time 7 expires and the alarm is not resolved, the process branches to step 538, wherein the sub-priority is escalated. Step 540 identifies a staff member either the same staff member or a new staff member. The escalation process returns to step 524, where the software determines if this is a H2 sub-priority.

The present disclosure describes a system and method for reducing alarm fatigue which entails reducing the number of alerts a staff member receives on their personal device. Steps 514, 526, and 534 send alerts to staff member's personal devices. In certain embodiments, sending an alert means updating the sub-priority on the same staff member's personal device without receiving a new alert from Alarm Management Application 120. The personal device will have the escalation times for each sub-priority stored in its local memory. In some embodiments, the escalated alert is accompanied by a vibration or beep to notify the staff member of the escalation.

Alarm fatigue is often exacerbated when more than one device is alarming concurrently in a patient's room with or without a clinician present. In the current disclosure, the alarm management device as described in FIG. 1, e.g., an alarm management device present in patient's room with a user interface and speaker, handles concurrent alarms. The alarm management software defines sub-priorities based on dynamic attributes for each device that alarms in the room. In certain embodiments, only H1 alarms generate audio in the room. For example, if an infusion pump has an H1 alarm while a ventilator has an M1 alarm, the alarm management device will generate an audio emergency alert and visually display device identification information associated with the pump that is alarming. The display of the ventilator alarm sub-priority would occur underneath the infusion pump sub-priority signaling lesser importance. In certain embodiments, the audio alert will have a device specific melody associated with an infusion pump which a clinician will recognize as an infusion pump alarm. In other embodiments, the alarm management software will instruct the infusion pump to generate the audio signal.

In some situations, e.g., ICU, multiple devices are alarming, and each device has an associated H1 as the original sub-priority. In certain embodiments, the alarm management device will generate an audio emergency alert and visually display the alarms in order of importance.

In some situations, multiple devices are alarming with H1 sub-priority alarms, however one device has the H1 sub-priority as the original sub-priority, while the other device has escalated to an H1 priority alarm after a defined period of time, e.g., an H3 sub-priority escalates to an H1 alarm. In certain embodiments, the device associated with the original H1 sub-priority alarm will be the alarm that generates the audio signal, e.g., a device specific audio signal, and visually displayed first, e.g., on the alarm management device user interface. In this situation, the original H1 sub-priority alarm is the true life-threatening situation.

Ventilator Alarms

In certain embodiments of the present disclosure, the sub-priority of a ventilator alarm may increase or decrease from the baseline value based on dynamic attributes from the patient, e.g., underlying condition, from the device, e.g., an $O_2$ setting on the device, or based on time, e.g., the time to retrieve a new ventilator after a system error, verifying a new sensor, etc. Often, ventilators have more than one clinical alarm simultaneously triggering based on the patient's ventilation status. For example, high airway pressure alarms are often associated with low tidal volume or low minute volume since the patient gets little or no ventilation when a high-pressure alarm has triggered. In certain embodiments, the presence of a second distinct clinical alarm following a first one indicates disease progression or worsening of a patient's ventilation status and the sub-priority of the first alarm will increase to reflect this.

FIGS. 6A-6E depict a flowchart 300 of an exemplary embodiment of a method of determining an initial alarm sub-priority to an alarm received from a ventilator, according to certain aspects of the present disclosure.

Figure 6A:
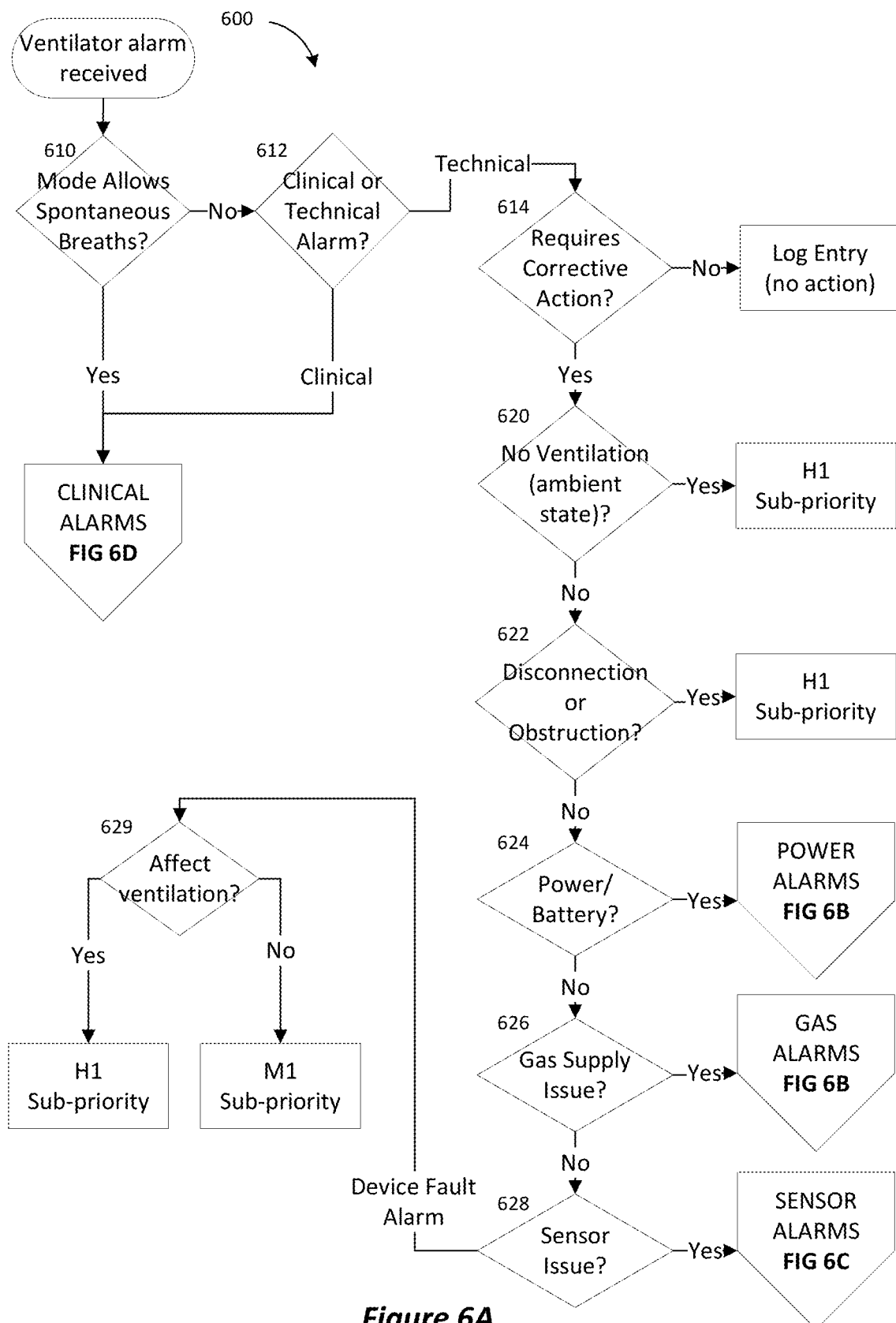
FIGS. 6A-6E depict a flowchart of an exemplary embodiment of a method of determining an initial alarm sub-priority to an alarm received from a ventilator, according to certain aspects of the present disclosure.

The process starts in FIG. 6A with receipt of a ventilator alarm. Step 610 branches depending on whether the ventilator is operating in a mode that allows spontaneous breaths by the patient or if patient is passively breathing and relying solely on the ventilator for breathing. The process branches from step 610 to FIG. 6D if the patient cannot spontaneously breath and from step 612 to FIG. 6D if the alarm is a clinical alarm. In this example, the workflow for assigning sub-priorities to ventilators contain logic for passive breathers, however, for spontaneous breathers, the sub-priorities will be lower since the harm associated with not responding to an alarm in a timely fashion is lessened.

At Step 612, the software branches on whether the alarm is a clinical alarm or a technical alarm. If a technical alarm, step 614 determines if the alarm is not actionable, i.e., for information only, and logs this information and terminates these processes. In certain embodiments, the highest sub-priority alarm, e.g., H1, is reserved for technical alarms that put the ventilator in an ambient state, i.e., state of no ventilation, and conditions that seriously compromise the ventilation circuit, e.g., disconnection or obstruction. Steps 620 and 622 check for these conditions and assign an H1 sub-priority. Power and gas supply alarms branch to FIG. 6B in steps 624, 626. Sensor alarms branch to FIG. 6C in step 628. In Step 629, a system error or device fault alarm that affects ventilation will be assigned a higher sub-priority, e.g., H1 or H2 sub-priority alarm. If ventilation is not affected, e.g., the display screen is not available, the alarm will be assigned a lower sub-priority, e.g., M1 or M2 sub-priority.

Figure 6B:
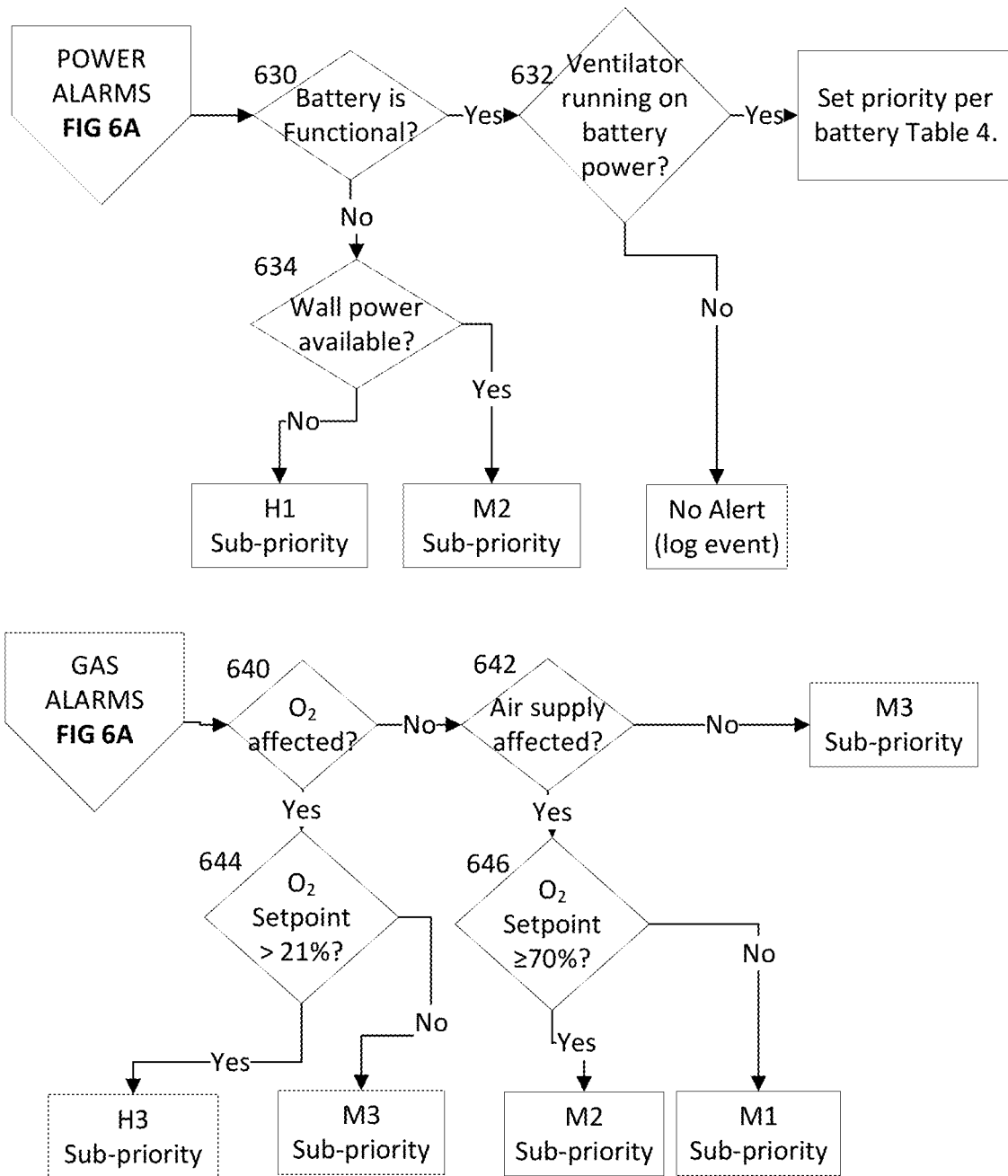

FIG. 6B depicts exemplary process for handling power and gas alarms. For power alarms, step 630 determines if the battery is functional. If the battery is operational, then the step 632 determines whether the ventilator is running on wall power or batteries. If the ventilator is running on wall power, and the battery is functional, then no alert is assigned since this may be just an alarm to say a battery with low power is recharging. If the ventilator is running on battery power, then a sub-priority will be defined based on the amount of time left on the battery. For example, an alarm indicating there is ten minutes of battery power will be assigned a M2 sub-priority.

If the battery is not functional, e.g., a charging issue, then step 634 determines whether the ventilator is running on wall power. If the battery is non-operational and the ventilator has lost its connection to wall source, then the ventilator has turned off and Step 634 assigns the highest sub-priority, e.g., H1. If the battery is not functional or has lost its ability to charge and the ventilator is connected to a mains power source is not, then step 634 assigns a lower sub-priority, e.g., M2 sub-priority. Depending on the staff role associated with a ventilator M2 priority, a lower-level staff member can install a new battery.

For gas alarms, step 640 determines whether the alarm is associated with an oxygen supply issue, e.g., a supply of $O_2$ has stopped. Room air consists of 21% oxygen. Patients may receive supplemental oxygen at levels up to 100% oxygen. Step 644 branches based on whether a patient is receiving room air or receiving supplemental oxygen. In certain embodiments, if the patient is receiving supplemental oxygen, a higher sub-priority is generated, e.g., H3, since the alarm indicates that the patient may be receiving less than the intended amount of oxygen. In other embodiments, the sub-priority is defined based on the amount of $O_2$ that is required. If the patient is receiving only room air or very minimal supplement oxygen, then a lower sub-priority is assigned, e.g., M3.

Ventilators can provide a breathing mixture from gases other than pure oxygen, e.g., manufactured air or heliox. If an air or heliox Gas Supply alarm is received, then the patient may be receiving pure oxygen from the ventilator.

Too much oxygen in the breathing mixture for an extended period of time may damage lung tissue. In certain embodiments, if step 642 determines that the alarm is related to the patient receiving the breathing mixture and the patient is breathing a 70% or greater oxygen levels, then step 646 assigns a lower sub-priority, e.g., M2. If the oxygen content of the breathing mixture is set to <70% oxygen, then step 646 assigns a higher sub-priority, e.g., M1, since the patient may not tolerate the excess oxygen. If the alarm is related to other aspects of the gas supply, for example a low gas supply tank pressure alarm, then step 642 assigns a lower sub-priority alarm, e.g., M3.

Figure 6C:
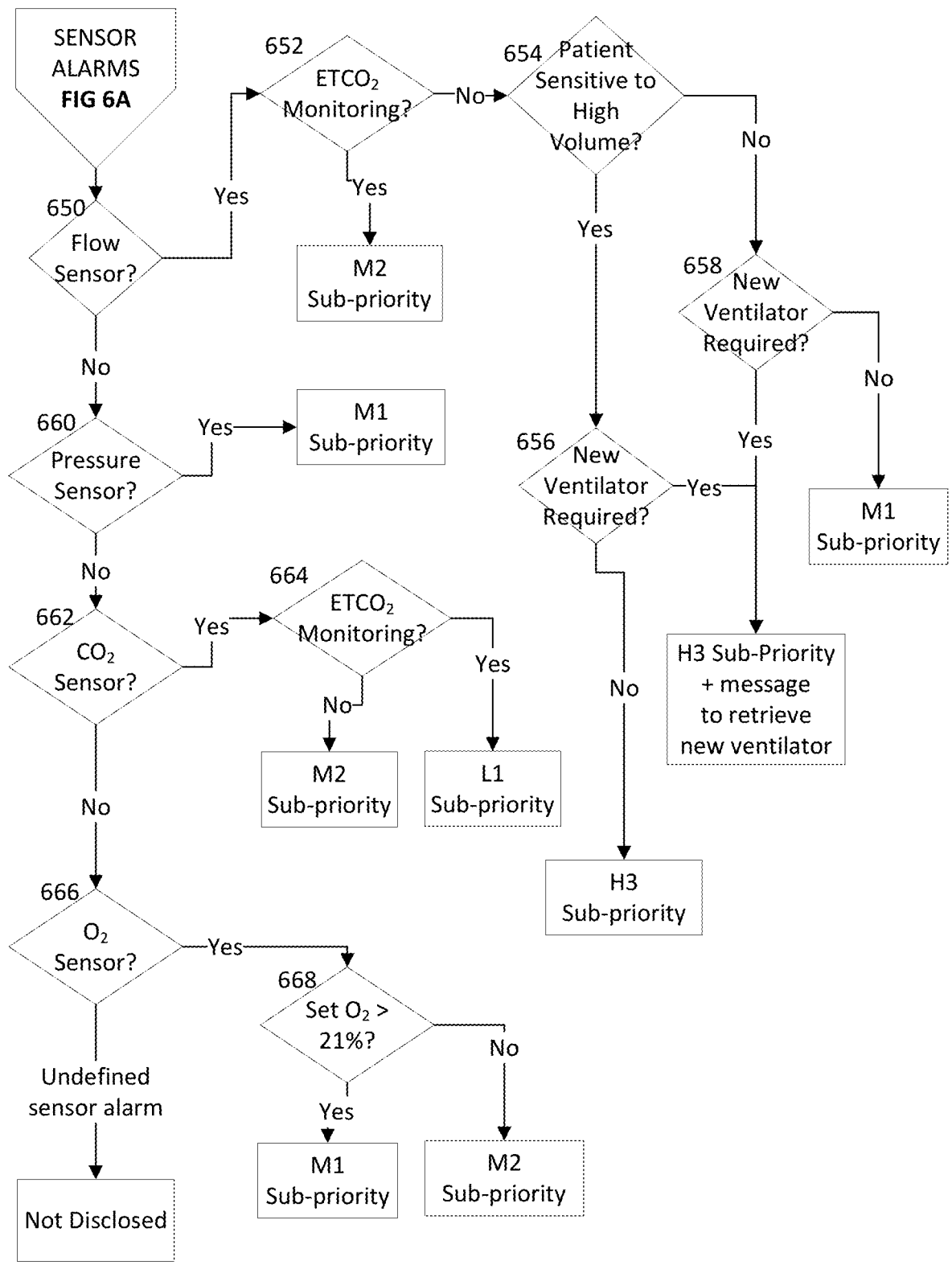

FIG. 6C provides the logic for assigning sub-priorities to sensor alarms, which can be related to non-functional sensors, sensors hooked up incorrectly, sensors requiring calibration, etc. Ventilators typically have flow, pressure, oxygen ($O_2$), and carbon dioxide ($CO_2$) sensors. The flow sensor is the most important sensor to maintain during the ventilation to determine if the patient is getting the correct flow rate. Alarm sub-priorities will be decreased if a primary sensor, e.g., flow sensor or $CO_2$ sensor, stops working but a redundant external monitoring activity is concurrently operating. For example, a lower sub-priority is warranted for both non-functional flow sensors and $CO_2$ sensors when the patient is also being monitored by an $ETCO_2$ monitor.

Steps 650, 660, 662, 666 branch depending on the type of sensor associated with the alarm. For flow sensor alarms, step 650 branches to step 652 where the application determines if there is a redundant monitoring source, e.g., $ETCO_2$ monitoring, and assigns a M2 sub-priority. If there is no redundant monitoring source then the software branches to step 654. If the patient is sensitive to excessive tidal volume, e.g., patient with an underlying condition of ARDS, COPD, etc., the process branches to step 656 that determines whether a new ventilator is required. If a new ventilator is not required, a H3 sub-priority is assigned. If a new ventilator is required, some manufacturer's flow sensors require a lengthy replacement and testing process, which requires manual ventilation in the interim, and an H3 sub-priority is assigned with an additional alert to a second staff member to retrieve a new ventilator.

If the patient is not sensitive to excessive tidal volume, then the software branches to step 658 to determine if a new ventilator is needed. If a new ventilator is needed an H3 sub-priority is assigned with an instruction to retrieve a new ventilator. Otherwise, a M1 sub-priority is assigned.

In the example of FIG. 6C, any pressure sensor alarm is assigned the same sub-priority, e.g., M1, in step 660.

In FIG. 6C, a $CO_2$ sensor alarm is assigned a sub-priority, e.g., M2, in step 664 if there is no $ETCO_2$ monitoring and a lower sub-priority, e.g., L1, if there is $ETCO_2$ monitoring.

After branching at step 666, an $O_2$ sensor alarm is assigned a sub-priority, e.g., M1, in step 668 if the patient is receiving supplemental oxygen and a lower sub-priority, e.g., M2, if the patient is not being treated with supplemental oxygen.

Figure 6D:
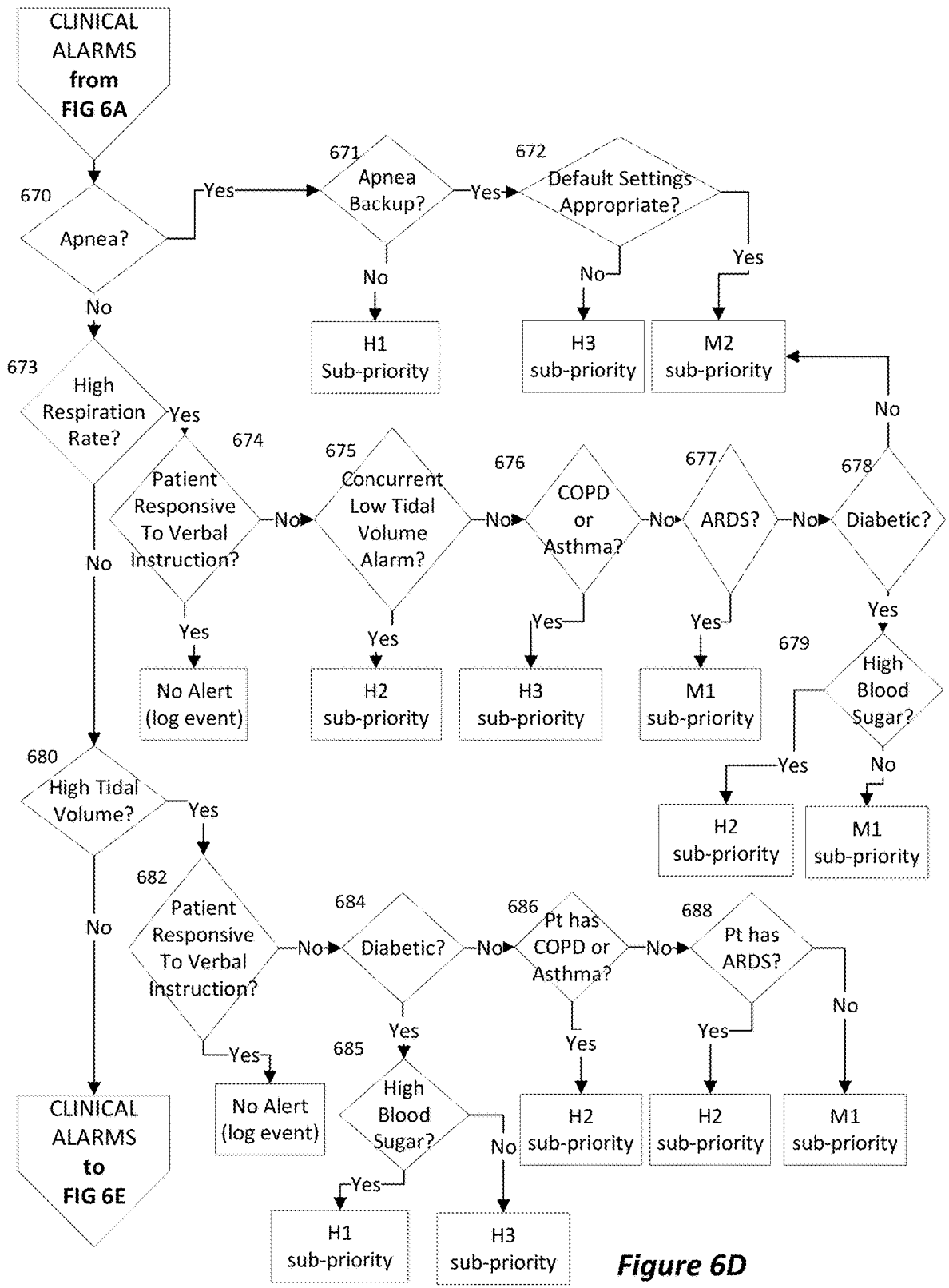
Figure 6E:
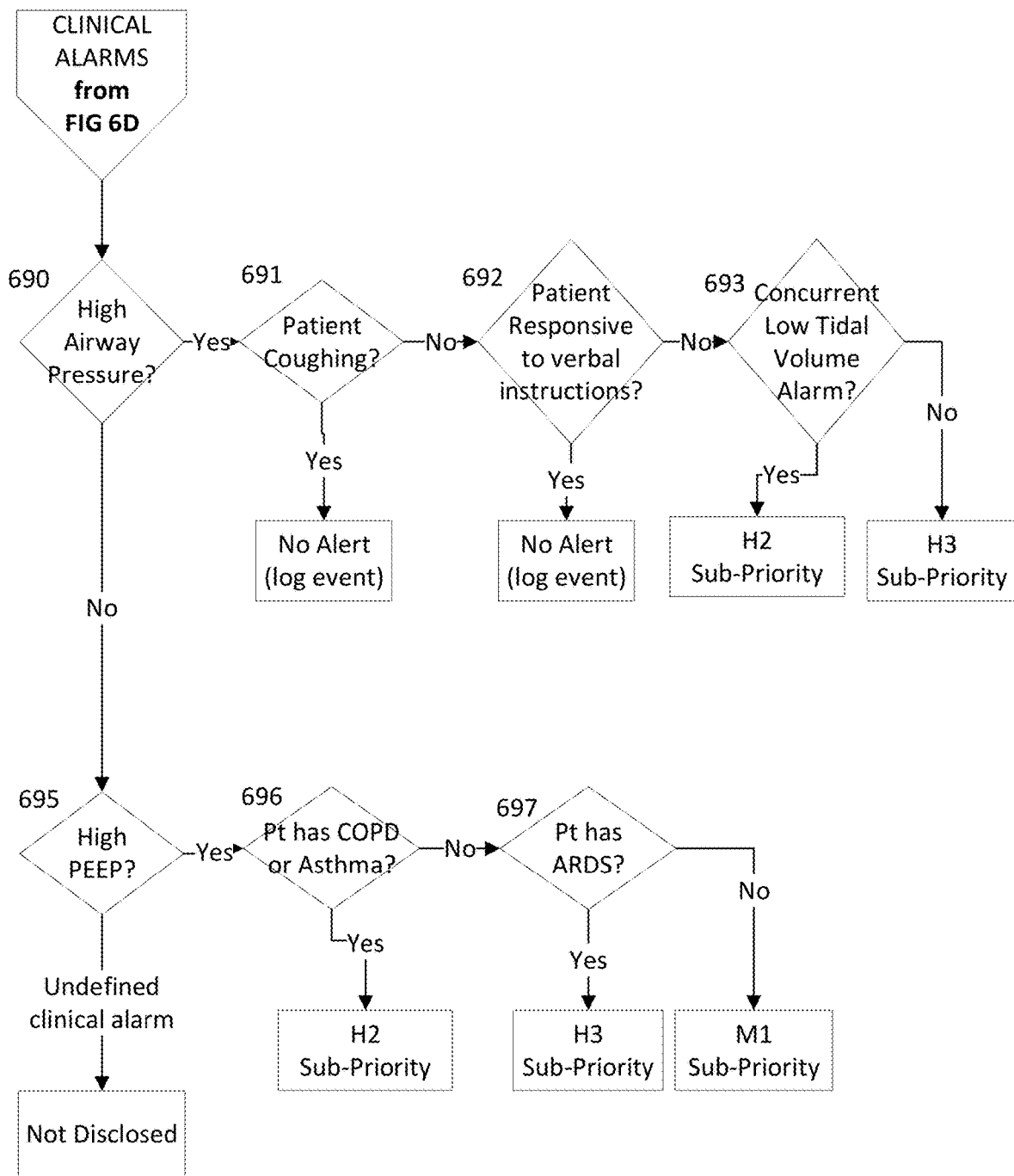

FIGS. 6D and 6E show the methodology of assigning a sub-priority for clinical alarms. These figures do not represent an exhaustive list of clinical alarms but cover numerous examples of how dynamic attributes define a sub-priority for a ventilator clinical alarm. Some of the steps in these figures illustrate how an alarm sub-priority may change from its baseline value based on the patient's medical or current condition e.g., COPD, a patient action e.g., coughing, or a redundant mechanism to mitigate harm e.g., $ETCO_2$ monitoring. Patients with certain types of underlying conditions require protective strategies while being treated with a ventilator. Conventional systems rely on the clinician to manually adjust the settings of the ventilator based on the underlying conditions. It is important that patients who have underlying conditions in need of a protective strategy have a higher sub-priority, so clinicians respond quicker to mitigate the potential increased harm. Alternatively, patients who may not need protective strategies may have lower sub-priorities which allows clinicians more time to respond and reduces alarm fatigue.

The disclosed method enables a hospital to define a set of rules that modify the sub-priorities assigned to certain alarm conditions that may interact with the underlying conditions. For example, patients who have COPD or asthma may experience chronic inflammation of small airways, which increases airway resistance and decreases elastic recoil. This leads to limited airflow and an impaired ability of the airways to remain open at the end of breath expiration. The collapse of airways at the end of expiration results in incomplete expiration, higher residual end-expiratory volume, hyperinflation, and auto-high positive end-expiratory pressure (auto-PEEP). Protective measures for ventilating COPD and asthma patients include preventing air trapping in the smaller airways by reducing the tidal volume, ensuring respirations are slow and deep, and ensuring the expiration time is significantly long enough to remove air.

In certain embodiments, higher sub-priorities are defined for diabetics. Diabetics who are prone to developing high blood sugar and potentially diabetes ketoacidosis (DKA) rely on respiratory mechanisms to compensate for metabolic acidosis and, therefore, are at a higher risk for certain alarm conditions which may indicate disease progression.

Step 670 covers an apnea alarm or when the ventilator is set to allow the patient to breathe by themselves, i.e., spontaneous breathing, however there is no respiration detected. Step 671 assigns the highest sub-priority, e.g., H1, if there is no back-up ventilation, otherwise branches to step 672 that assigns a lower sub-priority, e.g., M2, if the default settings of the back-up ventilation are appropriate for the patient and an intermediate sub-priority, e.g., H3, if the back-up setting are not appropriate.

Steps 673 and 680 branch for a high respiration rate and high tidal volume, respectively. For certain clinical alarms, the patient may be fighting the ventilator's breathing pattern due to agitation or pain. It may be possible to coach the patient to modify their behavior, e.g., their rate of breathing or their depth of inhalation, if the patient is not completely sedated. Coaching may include the instructions of Table 9. If the patient is responsive to verbal instructions, provided either in-person or remotely, e.g., via video terminal or speaker, then steps 674, 682 branch and the coaching successfully changes the patient's breathing pattern to address the alarm condition, then no alarm is generated. If the coaching is unsuccessful, then the process reverts to the alternate path from these steps and branches to steps 675, 684 respectively.

TABLE 9

| Alarm | Cause | Coaching |
| --- | --- | --- |
| high airway pressure | asynchrony | match ventilator setting for respiration rate |
| fast respiration rate | agitation, anxiety | slow respiration rate |
| high tidal volume | agitation, anxiety | take shallower breaths |

If the high respiratory rate alarm is associated with a concurrent low tidal alarm indicating a worsening ventilation status of patient, step 675 assigns a high sub-priority, e.g., H2. If there is no concurrent alarm and the patient has COPD or asthma, then step 676 in this example assigns the same priority, e.g., H3, since a fast rate may affect the patient's breath expiration and lead to air stacking in patient's having smaller airways. If the patient's underlying medical condition is acute respiratory distress syndrome (ARDS), then step 677 assigned a lower sub-priority, e.g., M1. If there is no concurrent alarm and the patient does not have COPD, asthma, or ARDS but is diagnosed as diabetic, step 679 checks the latest lab test and assigns a higher sub-priority, e.g., H2, if the patient has high blood sugar since the high respiration rate may indicate patient deterioration in this situation. If the diabetic does not have high blood sugar, then a lower sub-priority, e.g., M1, is assigned. In this example, the default for a respiratory alarm is an M2 sub-priority.

For a high tidal volume alarm, the patient is assessed in steps 684, 686, 688 for diabetes, COPD or asthma, and ARDS and appropriate sub-priorities are assigned. These sub-priorities are typically higher than sub-priorities for similar patient underlying conditions for a high respiration rate alarm because the high tidal volume usually occurs after a high respiration rate and/or indicates greater disease progression. A diagnosis of diabetes and a laboratory test showing high blood sugar causes step 685 to assign a high priority, e.g., H1, since the metabolic alkalosis is at a more advanced stage. Meanwhile normal blood sugar and the other conditions result in lower-level sub-priorities, H2 or H3. In this example, the default for a tidal volume alarm is an M1 sub-priority.

FIG. 6E depicts an exemplary process for two clinical pressure alarms. After branching in step 690 for a high airway pressure alarm, step 691 determines whether the patient is coughing, for example by checking for the sound of coughing prior to, during, or after the time of the alarm using a microphone near the patient, as it is common for this type of alarm to be triggered when the patient is coughing. In certain embodiments, microphone 114 of FIG. 1 is used to detect coughing. If the alarm unit microphone determines coughing is the reason for the alarm, then the event is logged, and no alarm is sent. If the patient is responsive to verbal instructions (See Table 8), to try to match the ventilation respiration settings and not fight the ventilation as seen in patient ventilator asynchrony then step 692 will provide coaching and suppress the if the instruction successfully resolves the high airway pressure alarm condition. If the coaching is unsuccessful, the process reverts to the alternate path and branch to step 693. If the high airway pressure alarm is associated with a concurrent low tidal alarm, step 693 assigns a high sub-priority, e.g., H2, otherwise the default sub-priority, e.g., H3, is assigned.

After branching in step 695 for a high positive end-expiratory pressure (PEEP) alarm, step 695 checks whether the patient has COPD or asthma and, if so, assigns a high sub-priority, e.g., H2, because high PEEP can cause injury with COPD or asthma patients. If the patient does not have COPD or asthma but is diagnosed as having ARDS, then a slightly lower sub-priority, e.g., H3, is assigned. In this example, the default for a high PEEP alarm is to assign an M1 sub-priority.

The disclosed system also provides an ability to adjust the threshold values for triggering a clinical alarm based on underlying conditions. For example, patients with ARDS may require a lower tidal volume alarm threshold and/or a lower PEEP alarm threshold. In addition, alarms for high tidal volume or PEEP for ARDS patients requires a quicker response time for clinicians to address the alarm condition before potential patient harm occurs. In both cases, the assigned sub-priority of certain alarms is increased for patients with the underlying condition compared to the same alarms for patients without these conditions.

Figure 7:
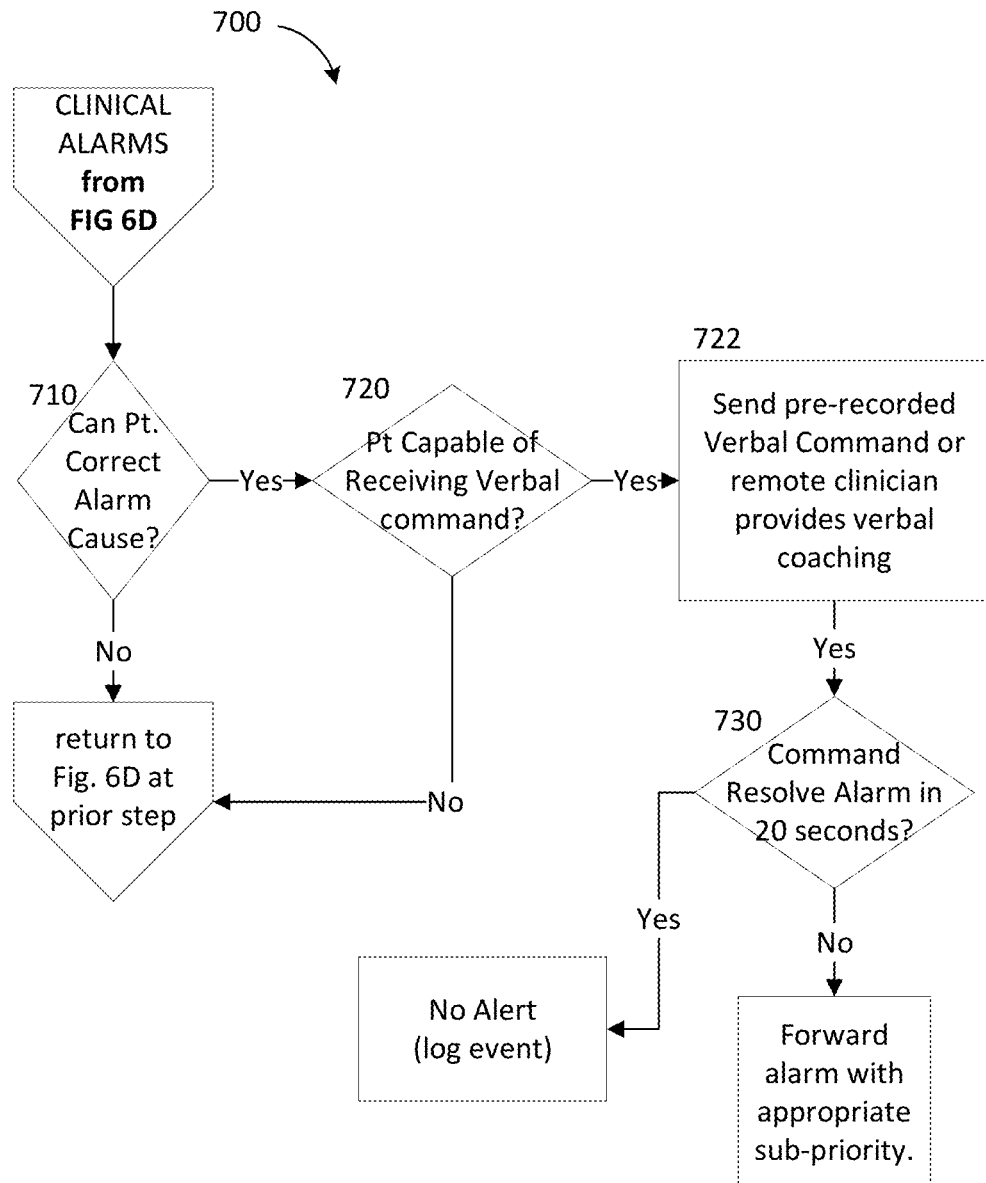
FIG. 7 is a flowchart of an exemplary embodiment of a method of guiding a patient to resolve a ventilator alarm, according to certain aspects of the present disclosure.

FIG. 7 is a flowchart 700 of an exemplary embodiment of a method of guiding a patient to resolve a ventilator alarm, according to certain aspects of the present disclosure. This process starts when an alarm condition has been received and Step 10 determines from the information in the alarms databased that one of the causes of the alarm may be resolved by a patient modifying their breathing pattern. If one of the causes of the alarm may be resolved by a patient modification, then Step 710 branches to step 720 otherwise it branches to the next decision point for the specific alarm. Step 720 determines whether the patient is capable of responding to verbal commands, e.g., is the patient conscious or sedated, and also returns to the next decision point for the specific alarm if the patient is unable to respond. If the patient is able to respond, the system provides coaching to the patient in step 722, either with a pre-recorded verbal command or via a staff member speaking through a remote interface via a video display or speaker. If the alarm condition is resolved within a pre-determined time period, then step 730 clears the alarm and logs the event. If the patient is unable to resolve the alarm condition, an appropriate sub-priority is assigned and an alert sent to the associated staff member.

Alarm Suppression

There are certain ventilator alarms where the potential cause of the alarm is related to a patient's behavior, e.g., agitation or anxiety. For example, a high respiratory rate or a high tidal volume, e.g., fast and/or shallow breathing, may generate an alarm reflects agitation of a patient being on a ventilator in a hospital room by themselves when they are awake, lightly sedated or on a daily spontaneous breathing trial. In addition, a patient may be fighting the respiration pattern provided by the ventilator, a behavior known as "patient-ventilator asynchrony," which may result in several alarms, e.g., high airway pressure alarm. For these alarms, it is possible to coach a patient who is capable of following instructions to change their breathing pattern, e.g., slow down respiration, to resolve the alarm. In certain embodiments, the disclosed system can resolve these alarms without involvement of a staff member.

For example, the Alarm Management System 120 receives a ventilator alarm and determines from a database in its memory that the alarm might be related to a patient's breathing pattern and that may be corrected with instruction, e.g., verbal command. The Alarm Management Application 120 can retrieve the ventilation mode and the set-point and actual respiratory rates from the ventilator and determine if the mode supports spontaneous breathing and if the patient is breathing spontaneous breaths. If both conditions are met, then in certain embodiments the alarm unit will retrieve the audio/video file from the database in its memory and provide the pre-recorded instructions on a video or audio device. In certain embodiments, a remote staff member may provide instructions via an audio or visual device. In certain embodiments, a pre-determined time period, e.g., twenty seconds, is allowed for the patient to be coached to resolve the alarm. If successful, then the alarm clears, and an information alert is sent to a remote clinician. If the time expires or the Alarm Unit determines that a potential cause of the alarm is not associated with patient behavior or the patient is not capable of responding to instructions, then the Alarm Management System 120 software will continue to process the alarm and assign an appropriate sub-priority alarm. In certain embodiments, the Alarm Management System 120 considers the time spent on this instruction when defining the sub-priority.

In certain embodiments, the Alarm Unit 110 uses its microphone to determine if the patient is coughing, which may be the reason for a high airway pressure alarm. The Alarm Unit's memory database will know that a potential cause of high airway pressure alarms is a patient coughing. In certain embodiments, the alarm unit hardware includes a built-in microphone (114 of FIG. 1) that can detect that a patient is coughing during a high airway alarm. If confirmatory, then a high airway pressure alarm will not be forwarded to a remote clinician if it does not continue after the coughing ceases. If the patient is not coughing, then then the software alarm logic for high airway pressure alarms will continue to proceed through its logic as shown in FIG. 6E.

Patient Monitor Alarms

A patient monitor is used to monitor a patient's vital signs and detect arrhythmias of different criticality, e.g., life-threatening, critical, and non-critical. Monitors are ubiquitous in both high acuity hospital environments, e.g., ICU, and lower acuity environments, e.g., medical/surgical floors. They play a significant role in generating the number of alarms in these environments and a large percentage of these alarms are not actionable, e.g., false positive alarms. The high frequency of non-actionable monitor alarms may have many causes, e.g., a weak signal to noise ratio, a motion artefact, electromagnetic interference, etc. To combat alarm fatigue, it is vital that dynamic attributes are used to provide context to alarms so clinicians know which alarms may be actionable and the sense of urgency in responding to them.

When clinicians respond repeatedly to monitor alarms that do not require an actionable response, they are inclined to take longer to respond to subsequent alarms, or resort to unsafe practices, e.g., turning off the volume of a monitor or utilizing the monitor's ability to suppress future alarms. Numerous safety signals from public databases indicate that turning off the alarm volume or using the suppression feature of a monitor is unsafe and may lead to serious injury or death. To facilitate preventing alarm fatigue and to ensure critical alarms are responded to in a timely fashion, the embodiments in this application clarify how dynamic attributes are used to provide the necessary alarm specificity to achieve these goals. Dynamic attributes provide context to clinicians to facilitate determining when a monitor alarm is associated with a true critical event, when a more urgent response is required to address an alarm associated with lack of monitoring or reliability of monitoring, and when a reduced sub-priority requiring a less urgent response is required, reducing the alarm fatigue factor for clinicians.

Figure 8A:
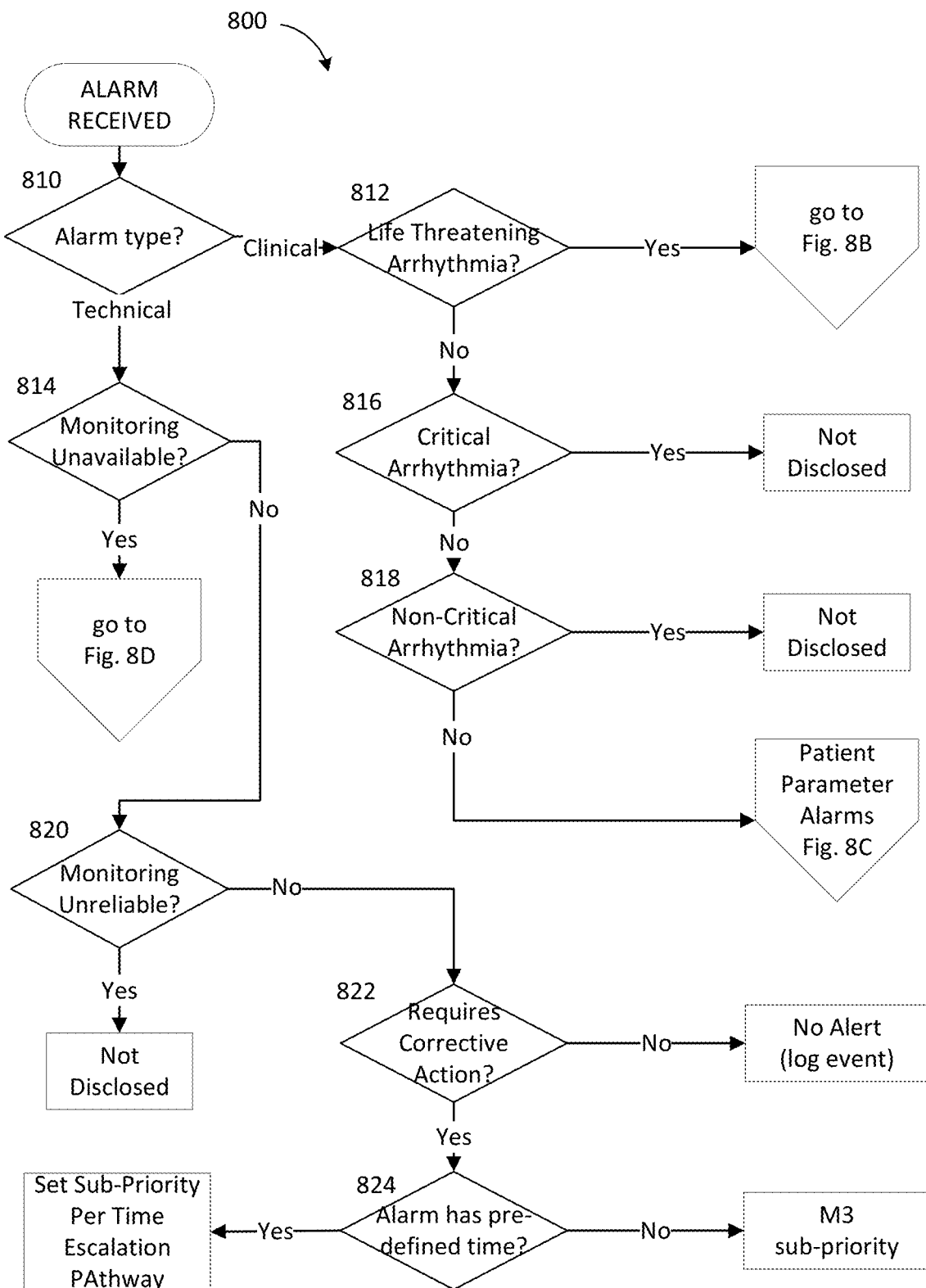
FIGS. 8A-8D depict a flowchart of an exemplary embodiment of a method of handling an alarm received from a monitoring device alarm, according to certain aspects of the present disclosure.

FIGS. 8A-8D depict a flowchart of an exemplary embodiment of a method of handling an alarm received from a monitoring device alarm, according to certain aspects of the present disclosure. FIG. 8A depicts an exemplary embodiment in how the Alarm Management System 120 depicted in FIG. 1 may classify each category of patient monitor alarms, each with their own separate logic and rules using dynamic attributes to define initial sub-priorities for the alarms within the category. As some monitors have hundreds of different alarms, this flowchart includes only a few exemplary workflows to show how a sub-priority may be defined for each alarm based in part on dynamic attributes associated with the patient, including equipment being used to treat or monitor the patient.

The process 800 starts in FIG. 8A with receipt of an alarm. Step 810 branches depending on whether the alarm is associated with a clinical alarm or a technical alarm. If the alarm is technical, then step 814 determines if the patient monitoring is available or unavailable. For example, monitoring is unavailable when the monitoring loses power, a lead becomes disconnected, the monitor experiences a system error and requires to be taken out of service, etc. This category of alarms covers both the case where all monitoring is lost, e.g., a patient monitor 134 loses power, or when only one of the parameter is not available, e.g., a lead has become disconnected.

Figure 8B:
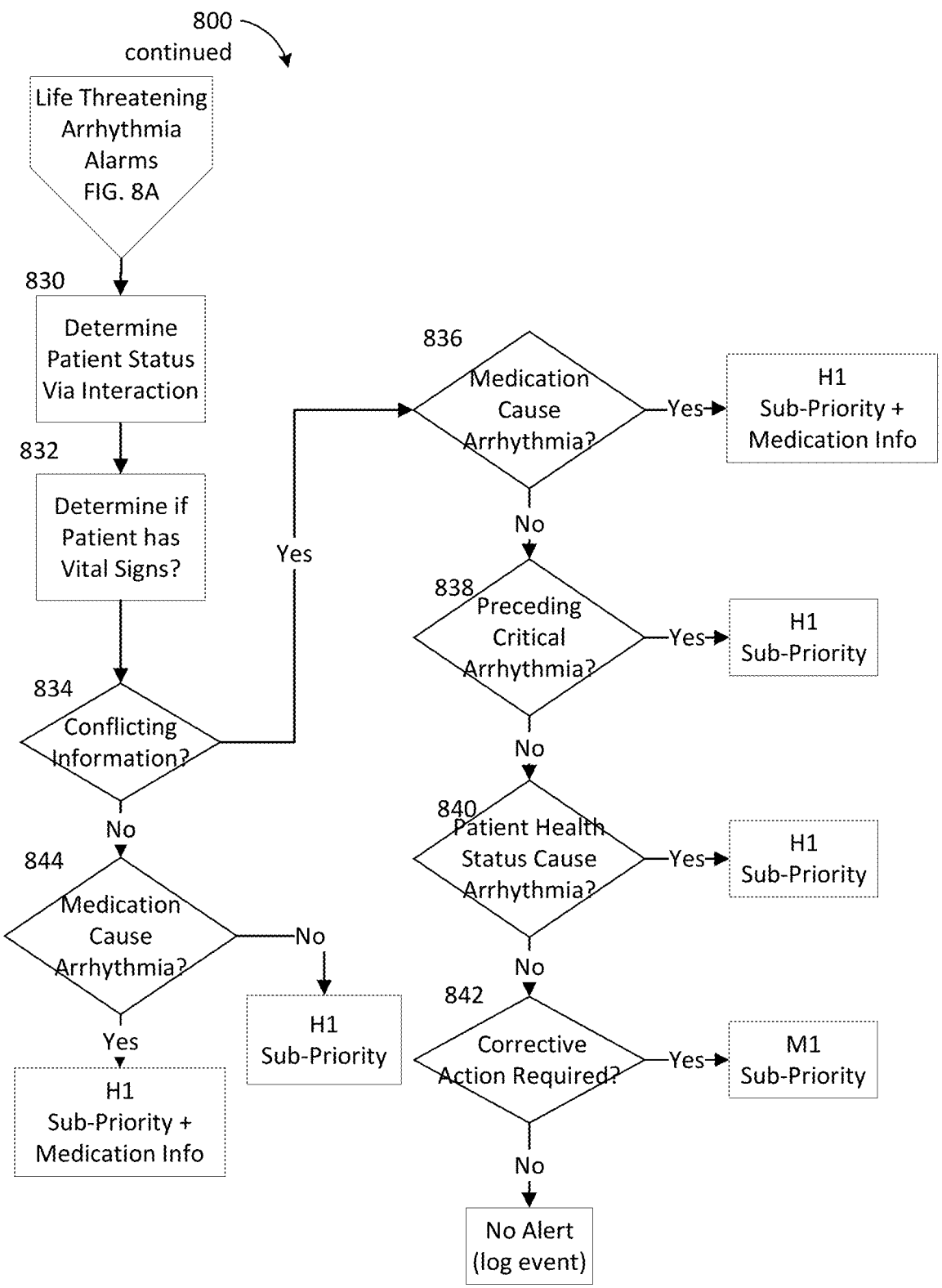
Figure 8C:
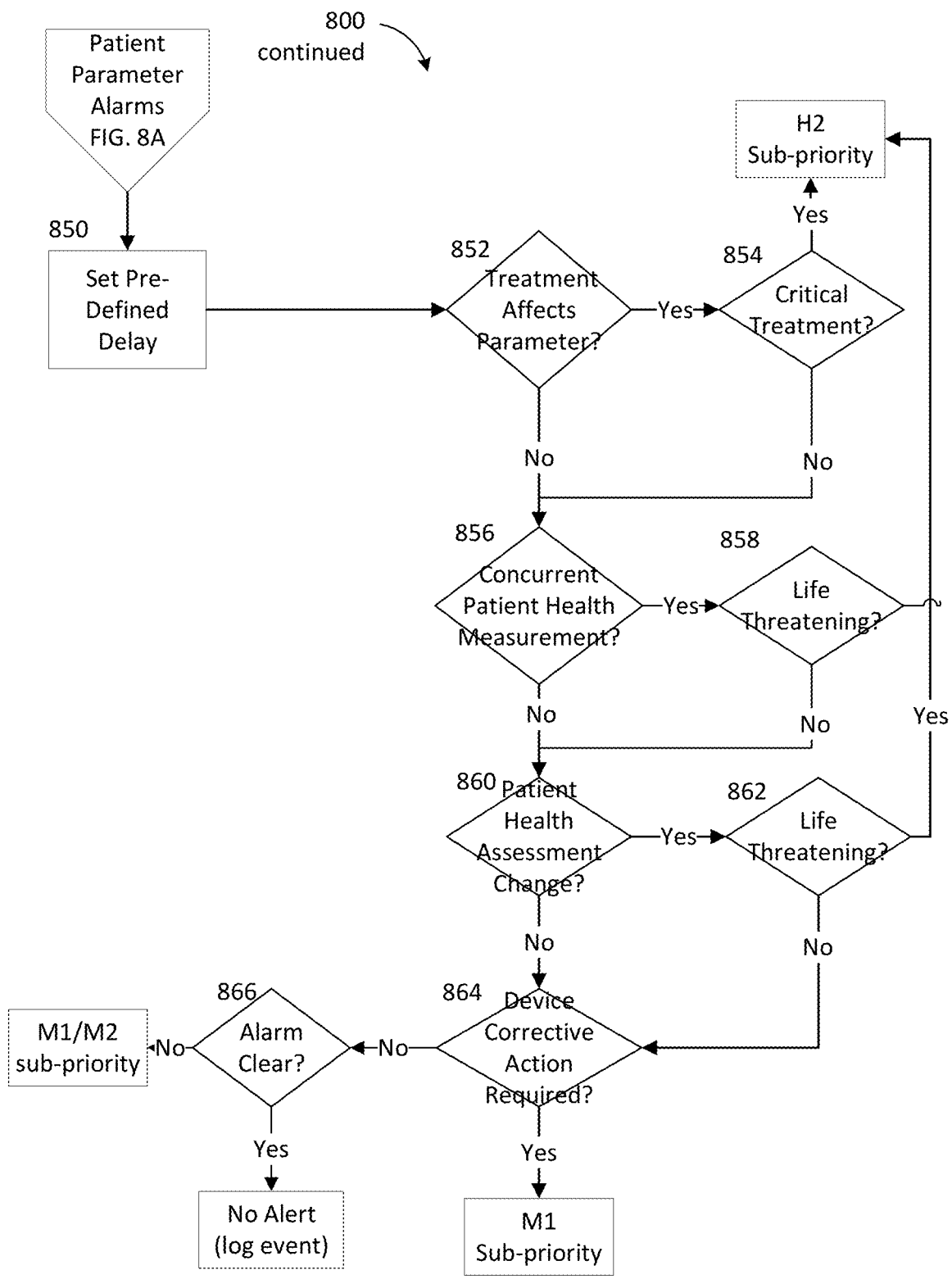
Figure 8D:
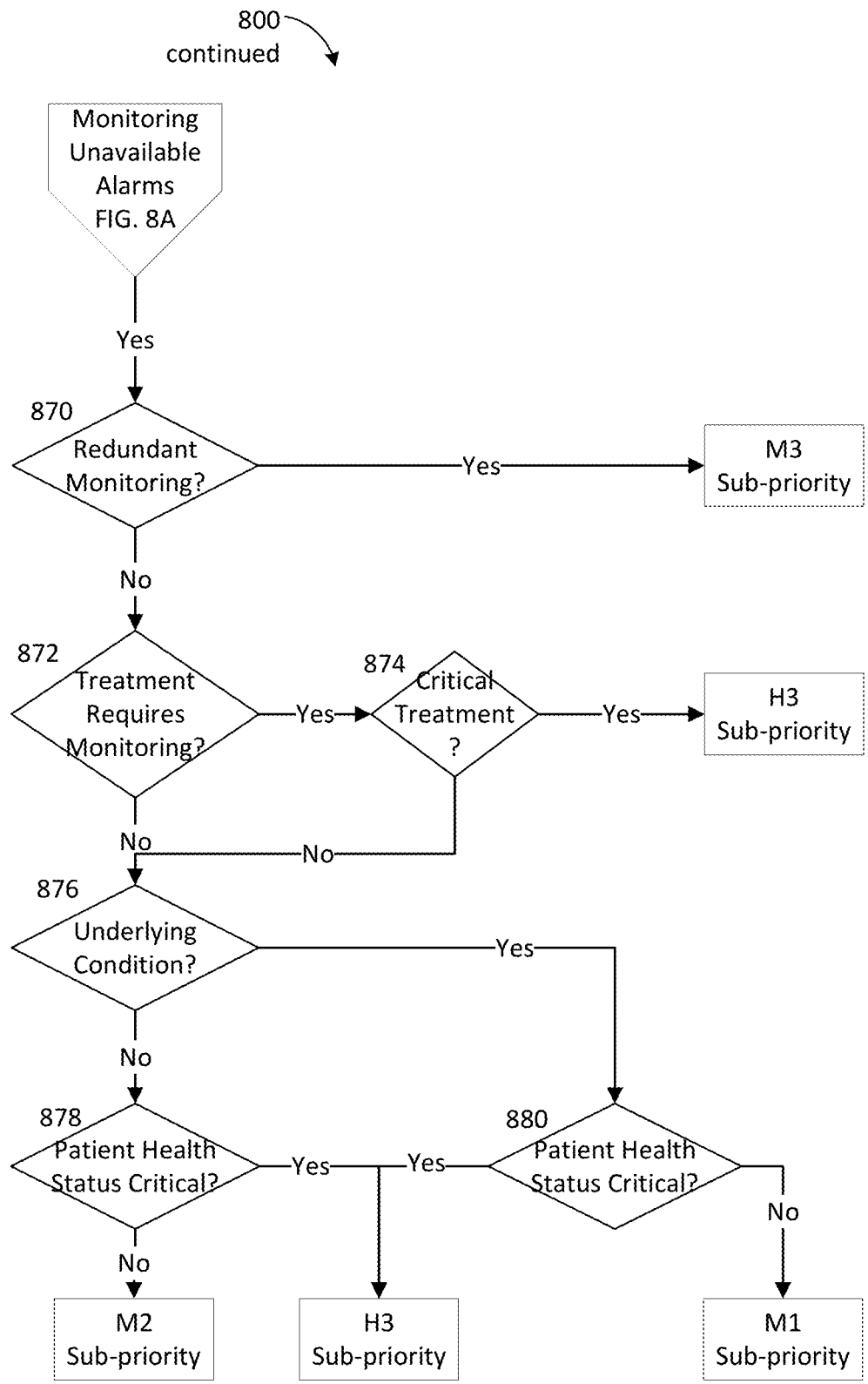

If monitoring is unavailable, then the logic branches to FIG. 8D. If monitoring is available but is unreliable, e.g., due to motion artifact or a potential cause that may weaken a signal, then logic can be developed (not included in this disclosure) similar to, although not necessarily identical to, the logic for handling an absence of monitoring.

If a technical alarm is received while monitoring is available and reliable, then steps 814, 820 direct the process to step 822 that determines whether the alarm requires corrective action. If an action may be required, the process branches to step 824 that determines whether this alarm has an associated time, e.g., the alarm is indicating that a recommended service period has expired and assigns a lower priority if this is a routine timed event. If no corrective action is required, then no alert is generated. If the alarm is clinical in nature, then Steps 812, 816, 818 determine if the alarm is a life-threatening arrhythmia e.g., asystole, ventricular fibrillation, a critical arrhythmia e.g., ventricular tachycardia, a non-critical arrhythmia e.g., premature ventricular contraction, or a patient parameter alarm e.g., heart rate, blood pressure, $SpO_2$, etc. Each of these categories would have their own logic utilizing dynamic attributes to define initial sub-priorities or when to suppress an alarm signal and not send it in an alarm forwarding scheme. Exemplary logic for a life-threatening arrhythmia alarm is described in FIG. 8B and for a patient parameter alarm in FIG. 8C.

FIG. 8B depicts an exemplary process for handling a life-threatening arrhythmia alarm from a patient monitor. Although a true asystole or ventricular fibrillation alarm is always a high priority, the disclosed system can determine if an alarm may be a false positive and therefore not require a high priority sub-priority.

Steps 830, 832 gather information to help determine if the asystole or ventricular fibrillation alarm is a true event. In certain embodiments, step 834 determines if the patient's status is consistent with a life-threatening arrhythmia by determining if an interactive cue from a speaker receives a response in return. In other embodiments, a remote clinician may try to confirm the alarm condition does not exist via Alarm Unit 100, e.g., with the video surveillance camera 118 of FIG. 1, located in the patient's room. In certain embodiments, the system will review the dynamic attributes to determine if there is reliable source of vital sign information that contradicts the asystole or ventricular fibrillation alarm. For example, numerous peer-reviewed articles have confirmed that the presence of certain vital signs, e.g., arterial blood pressure, conflicts with an indication of a life-threatening arrhythmia. If the obtained information does not conflict with the received alarm, then step 834 branches to step 844 that checks whether the patient is on a medication that may cause the arrhythmia and, if confirmatory, assigns an H1 priority and includes this drug information in the alert. Otherwise, an H1 sub-priority is assigned.

If there is conflicting information in step 834 as to whether the patient is truly experiencing a life-threatening arrhythmia, the process branches to step 836 that checks whether the patient is on a medication that may cause the arrhythmia and, if confirmatory, assigns an H1 priority and includes this drug information in the alert.

If the patient is not receiving a medication that could cause an arrhythmia, the process branches to step 838 that determines if the patient has had a preceding critical arrhythmia alarm. A patient with a ventricular bradycardia may experience increasingly serious arrhythmias over time. If a critical arrhythmia alarm has preceded the current alarm, then step 838 assigned an H1 sub-priority. If the patient has no history of these alarms, the process branches to step 840.

Step 840 determines whether one of the patient's health measurements indicates that the patient could develop a life-threatening arrythmia. For example, a patient may have symptoms, or a blood test associated with carbon monoxide poisoning which could lead to a life-threatening cardiac arrhythmia, e.g., ventricular fibrillation. If there is a significant health status information, step 840 assigned an H1 sub-priority.

If there is no underlying conditions, history, or dynamic attribute that suggests the patient is prone to a life-threatening arrhythmia, the process branches to step 842 that assigns a lower priority, e.g., an M1, if the alarm requires a corrective action, otherwise the alarm is logged but not assigned a sub-priority and no alert is issued. A corrective action may be required in this situation if a dynamic attribute has determined the time has expired on the recommended frequency to change the leads, recommending the leads. In certain embodiments, the Alarm Management Application 120 will log the number of nonactionable or false alarms before this current alarm. A high number of false alarms will send a low priority alert, e.g., M1 or M2, to prompt a technician to determine if electromagnetic interference may be causing the false positive alarms or if the monitor should be replaced.

FIG. 8C depicts exemplary process for handling a patient parameter clinical alarm associated with a patient monitor. These alarms may include heart rate, blood pressure, respiratory rate, $SpO_2$, etc. The urgency of responding to parameter alarms depends on the dynamic attributes associated with the patient. In some cases, a higher sub-priority, e.g., H2 or H3, is recommended when a patient parameter is associated with a potential life-threatening situation. In other cases, either a lower sub-priority, e.g., M1 or M2, for an actionable alarm or no alert may be appropriate.

Step 850 applies a pre-defined delay since a patient parameter alarm, e.g., $SpO_2$, is often transitory in nature and the alarm condition resolves within the delay period. Step 854 determines if the patient is on a treatment that may affect the patient parameter alarm. A patient treatment may be the administration of a fluid or medication from an infusion pump to treat low blood pressure, an implantable device, e.g., a pacemaker, to treat an out-of-range heart rate, etc. In certain embodiments, the Alarm Management Application 120 will consider if the fluid or medication is indicated to treat the parameter or may have side effects that affect the parameter. If the patient is on such a treatment, the process branches to step 854 that assigns a high sub-priority, e.g., H2, if the treatment is critical and otherwise branches to step 856.

Step 856 checks whether any patient health measurement can affect this alarm and, if so, the process branches to step 858 that assesses whether the combination of alarm and dynamic attribute is life-threatening. For example, if the initial alarm is associated with a high heart rate but the patient health measurement showed that there was a period of bradycardia before this alarm, then a potentially serious condition Tachy-Brady Syndrome may manifest, which may require the need for an internal pacemaker if symptoms are significant enough. Another example is if the patient alarm is for high blood pressure and one of the patient health measurements, e.g., lab value, associated with the patient is high blood sugar indicating diabetic ketoacidosis then a higher sub-priority is warranted since disease progression is indicated. If there is an indication that the situation is life-threatening, step 858 assigns an H2 sub-priority otherwise routes the process to step 860.

Step 860 determines if the current patient health measurements change the score of a patient health assessment. Patient health assessments like the MEWS are used in lower acuity settings, e.g., a medical ward. In certain embodiments, if the score is high enough, then then the process branches to step 862 and if the new algorithm value indicates a life-threatening risk, step 862 assigns an H2 sub-priority that will cause a rapid response team to assess whether the patient should be moved to a higher acuity setting, e.g., ICU. If the patient health assessment has changed but does not rise to a life-threatening situation, then the process branches to step 864. If the algorithm score has not changed, the process also proceeds from step 860 to step 864.

Step 864 determines whether a corrective action is required on the device to address the alarm. For example, an alarm indicates that the recommend time to change the leads has expired, thus necessitating a clinician or technician changing the leads. In an example, a device parameter has exceeded a limit and based off the dynamic attributes in steps 854, 856 and 860 not being affirmative, the hospital staff has pre-approved an increase or decrease in the limits so the alarm condition does not re-occur. If a corrective action is required, then a M1 sub-priority alarm is generated. If not, the process branches to step 866 to determine whether the alarm has cleared within the initial delay, e.g., self-cleared. If the alarm clears, then no alert is sent to a remote clinician. If the alarm is not resolved, then in certain embodiments a lower priority alarm is assigned, e.g., M1 or M2. In certain embodiments, if steps 854, 858, or 862 is not affirmative, e.g., a patient treatment affects the parameter but the treatment is not critical, an M1 sub-priority is assigned. In certain embodiments, the default setting is an M2 sub-priority FIG. 8D depicts the handling of a technical alarm when some aspect of monitoring is not available, e.g., leads are disconnected, a sensor has failed, etc. In conventional systems, a loss of patient monitoring is uniformly assigned a medium priority alarm. As with patient parameters, the system disclosed herein assesses related dynamic attributes and adjusts the sub-priority up or down based on this additional information, thereby alleviating alarm fatigue.

Step 870 determines if there is redundant monitoring in place. In certain embodiments, if the $SpO_2$ probe is disconnected, which is one of the more frequent monitoring alarms in a hospital, but end tidal $CO_2$ is being measured via capnography, then a low sub-priority, e.g., an M3, is assigned.

If there is not a viable redundant monitoring process in place, the process branches to step 872 that determines whether the patient is undergoing a treatment that requires monitoring associated with the alarm. For example, treating high blood pressure with a medication requires blood pressure monitoring and loss of the blood pressure monitoring assigns an H3 sub-priority. For the same example of a patient being treated for high blood pressure, loss of the $SpO_2$ monitoring would be considered a "no" and the process would branch to step 876.

Step 876 determines if the patient has an underlying condition pertinent to the monitoring being performed. If yes, then the process branches to step 880 that determines if the patient health measurement or other indicator is critical. For example, if the patient is experiencing serious symptoms, has a high patient health assessment score, or has a critical patient health measurement such as a positive lab test for a cardiac marker, then step 880 assigns a H3 sub-priority. If the patient does not have a critical indicator, a lower sub-priority, e.g., an M1, is assigned.

If the patient does not have an underlying medical condition, the process branches from step 876 to step 878 that will assign an H3 sub-priority if the patient health measurement is critical but assign an even lower sub-priority, e.g., an M2, if their status is not critical.

Dynamic Attributes of Staff

In order to further provide the best possible care of a patients in a healthcare environment, for example a hospital, it is appropriate to consider the characteristics of the staff members who provide that care when handling alarms. The sheer number of alarms is not the only factor that may cause stress and burn-out of staff. In addition to considering dynamic attributes of a patient in the assignment of a sub-priority to an alarm, as disclosed elsewhere herein, factors that may contribute to stress of a staff member or the risk of an adverse event occurring should be considered.

The consideration of dynamic attributes associated with the staff, their assigned patients, and the facility in the selection of a recipient for the alert associated with an alarm is disclosed herein. In this regard, dynamic attributes can be broadly classified into groups based on the following attributes of a staff member: capability to respond to an alarm, availability to respond to an alarm, current workload status, burnout status (i.e., both current and long-term), performance (over a defined period), the management or level of support of a staff member, and the facility in which a staff member works. Dynamic attributes associated with a staff member include, but are not limited to, the examples listed in Table 10.

TABLE 10

| | | ATTRIBUTE | EXAMPLE |
|---|---|---|---|
| 1 | | a capability attribute of a staff member | |
| | a | age | 30 y/o, 60 y/o |
| | b | education | licensed practical nurse, registered nurse, physician |
| | c | experience | five years' of experience in an intensive care unit |
| | d | training | training on a specific brand of infusion pumps, ventilators, etc. |
| | e | frequency of training | staff member who just took the refresher training |
| | f | physical capability | impaired movement, not able to lift > X pounds |
| | g | a psychometric status of a staff member | aptitude test, skill test, personality test |
| 2 | | an availability attribute of a staff member | |
| | a | a break status of the staff member | on break, working |
| | b | a distance from the staff member to the medical device | distance too far to respond to alarm |
| | c | do not disturb status | working a code |
| | d | staff member closest to patient alarm | closest by feet, second closest by feet |
| 3 | | a workload attribute of a staff member | |
| | a | a number of patients assigned to the staff member; | 5:1 ratio |
| | b | a number of patients having a patient health assessment score above a threshold | number of patients with high acuity, stability, complexity, deterioration scores |
| | c | an aggregate patient health assessment score of assigned patients above a threshold | total scores for patients assigned to staff member |
| | d | a number of active alarms above a sub-priority threshold and assigned to the staff member | three active high priority alarms |
| | e | a number of scheduled tasks in current time period | five active nurse calls, 4 infusions ordered |
| | f | a number of potential device tasks in current time period | 14 active infusions assigned to current patients, 5 active infusions with critical medications, 10 critical devices that can alarm, 25 total devices that can alarm |
| | g | a patient who requires special care assigned to the staff member | patient who is at high risk for falling or exiting bed (e.g., combative or dementia patient), ventilated patient at high risk of extubating, etc. |
| 4 | | a burnout attribute of a staff member | |
| | a | a reported level of burnout | monthly job satisfaction score, in-shift emotional exhaustion score survey stating clinician needs a vacation or new job |
| | b | a grief event | divorce, death of a loved one |
| | c | a measurement of the staff member | blood pressure, number of steps, electrical activity of the brain indicating amount of sleep or activity, a lab value, a measure for medication compliance |

TABLE 10-continued

| | ATTRIBUTE | EXAMPLE |
|---|---|---|
| | d a self-reported value or activity | the number of hours slept before shift, medication compliance |
| | e a work schedule | staff on overtime hours, number of shifts worked without a day off, number of night shifts per week, number of shifts before a vacation |
| | f a number of hours worked per time period | number of hours worked on current shift, number of hours worked in last X days, number of hours worked since last vacation |
| | g a percentage of time where workload status = high | 90% of a staff member's shift, 80% of staff's shifts in last two weeks |
| | h a number of device tasks performed per a given time period | responded to 85 alarms in last 12 hours, |
| 5 | a performance attribute of a staff member | |
| | a a never event (per time period) | two never events in last 30 days |
| | b a preventable adverse event associated with the staff member per time period | three preventable adverse events in last 30 days |
| | c an event (per time period) | five adverse events in last 30 days |
| | d a patient complaints (per time period) | three patient complaints in last 30 days |
| | e an alarm response time > goal (per time period) | five high priority alarm responses > goal in last 30 days |
| 6 | a management attribute of the staff member | |
| | a a number of backups | 2 backups/staff member |
| | b assigned as a back-up to another staff member | yes/no |
| | c an attribute of the backups | a capability, a workload status, etc. |
| | d an overall ratio of patients to backups | 12 to 1 |
| | e staffing level of current shift | 60% staffed, 100% staffed |
| | f time period of shift | shift change |
| | g type of shift | days, nights, weekend |
| | h hours in a shift | 8 hours, 12 hours |
| 7 | an attribute of a facility | |
| | a a type of facility | intensive care unit, medical/surgical floor |
| | b a capacity of the facility | 1200 square feet |
| | c a maximum patient-to-staff ratio of the facility | 3:1 for an ICU |
| | d a special control in practice for the facility | need to wear personal protective equipment |
| | e a technology available in the facility | cameras used for dementia patients to notify for potential fall risk |

As used within this disclosure, the phrase "adverse event" identifies an undesirable experience associated with the use of a medical product in a patient that could result in harm (e.g., death, injury, prolonged hospitalization, etc.), even when the care is not the cause of the occurrence.

As used within this disclosure, the phrase "preventable event" identifies an adverse event that happens, or is made possible to happen, because of either an error of commission or an error of omission made by a care provider. The error is rarely due to negligence. The error may be an inaccurate or incomplete diagnosis of a disease or an improper execution of a treatment procedure. Errors have also been attributed to issues in communication, complexity of technology used in treatment, and the use of increasingly powerful drugs.

As used within this disclosure, the phrase "never event" identifies an event that should never happen to a patient. Examples include a wrong-site surgery, a transfusion with the wrong blood type, development of a pressure ulcer, a fall, and a hospital-acquired infection.

As used within this disclosure, the phrase "grief event" identifies an event having a lasting emotional impact and can affect the staff member's ability to do their job. This may be a personal event, e.g., a divorce or loss of a family member, or a community event, e.g., loss of a coworker or closing or a portion of the hospital. The magnitude and duration of the impact, as well as the effect upon normal activities, may vary greatly. Involvement with an adverse event, particularly a preventable or never event that involves significant injury or death, can be traumatic and may cause a grief event for the staff member.

As used within this disclosure, the phrase "break status" identifies whether the staff member is on a break, i.e., temporarily not actively providing care. Given the long shifts often worked by staff members and the nature of the care being provided, it is important for staff members to periodically have a break. This may be indicated by the presence in a particular location, e.g., in a lunchroom (having a meal). This may also be indicated by a staff member actively indicating that they are taking a break, e.g., by changing their status on a physical tracking board or in a software program. In certain embodiments, it is desirable to avoid interrupting a break of the otherwise first-choice recipient, due to the adverse impact on that staff member, when another staff member can handle an alarm.

As used within this disclosure, the term "back-up" identifies a staff member who has been determined to have the ability to provide at least a portion of the care normally provided by another staff member. There is an expectation that the back-up will be called on only infrequently, as the back-up will have their own responsibilities. Certain back-ups, e.g., a peer or a supervisor, may be identified as a back-up for all responsibilities of a staff member. Certain back-ups may be identified as a back-up only for specific types of alarms, e.g., a technician being a back-up to a nurse only for a low battery alarm.

Do not Disturb Status

At times, a staff member may be provided with an alert that is associated with an alarm or condition that requires an immediate response and cannot be paused to take care of a second alarm. In certain embodiments, the system and method disclosed herein assigns a Do Not Disturb (DND)

status to that staff member. The DND status persists, i.e., is "active," until it is reported that the alarm has been satisfactorily resolved. In this context, certain conditions, e.g., fire, a disaster, or severe weather, are considered interchangeable with an alarm as far as initiating an alert and are considered active until the condition is no longer present.

The system assigns a DND status based on an evaluation of one or more dynamic attributes of alarms for which an associated alert was sent to the staff member. In certain embodiments, the dynamic attributes are included in a group that comprises the number of active alarms that have a sub-priority greater than a predetermined level, the number of active alarms that require a response having a complexity equal to or greater than a predetermined level, and the number of emergency codes. In certain embodiments, the system will not send an alert for other alarms to a staff member that has an active DND status. For example, in certain embodiments, a staff member having received a first alert associated with an alarm having a sub-priority of H1-H3, or any high priority event or condition, will not be provided with an additional alert until their DND status is no longer active. In a second example, in certain embodiments, a staff member can receive two alerts associated with an alarm having a low sub-priority, e.g., less than M2, without being assigned a DND status.

Emergency codes and associated colors are defined by a health care facility to coordinate a response by staff members to situations that require immediate action. A code is declared when the event occurs. While the definition of which code color is associated with an event is not universal, exemplary guidance defines the following colors:

| | |
|---|---|
| red | fire (seeing flames, seeing or smelling smoke) |
| blue | adult emergency, such as cardiac arrest or respiratory failure |
| yellow | bomb threat; disaster |
| gray | combative person; severe weather; security response required |
| silver | a weapon or hostage |
| pink | infant or child abduction |
| orange | hazardous material accident |

An emergency code may be declared and publicly announced, for example over a public address (PA) system or broadcast electronically to multiple staff members, e.g., everyone in a building, via their personal devices, e.g., mobile phones. These actions are considered as equivalent to an alarm being issued by a medical device, an assignment of the highest priority, and provision of an associated alert to a staff member. In certain embodiments, the dynamic attributes include a location at which an emergency code has been declared and a location of the staff member and the DND status is assigned to the staff member if the staff member is within a predetermined distance of the emergency code location.

In certain embodiments, the system is configured to determine a task criticality for the alarm based in part on a dynamic attribute of the staff member. In certain embodiments, the system is configured such that once a staff member is sent an alert related to such an alarm having a determined criticality greater than a threshold, the staff member is assigned a DND status, i.e., no further alerts will be sent to that staff member until they complete the corrective action. In certain embodiments, a staff member to whom a DND status is assigned with have one or more of any prior alarms that were assigned to them re-assigned to other staff members such that they can focus on the DND-related alarm without impact to other patients. Examples of when a staff member is assigned a DND status include (a) working an emergency code, e.g., a "code blue," (b) dealing with a difficult patient, e.g., a dementia patent at risk for falling, (c) performing a complex critical task, e.g., setting up multiple infusions on multiple pumps, and (d) performing a task that requires the staff member to consult supplemental training material, e.g., a staff member has limited capability but there is no one else to respond to the alarm.

Figure 16:
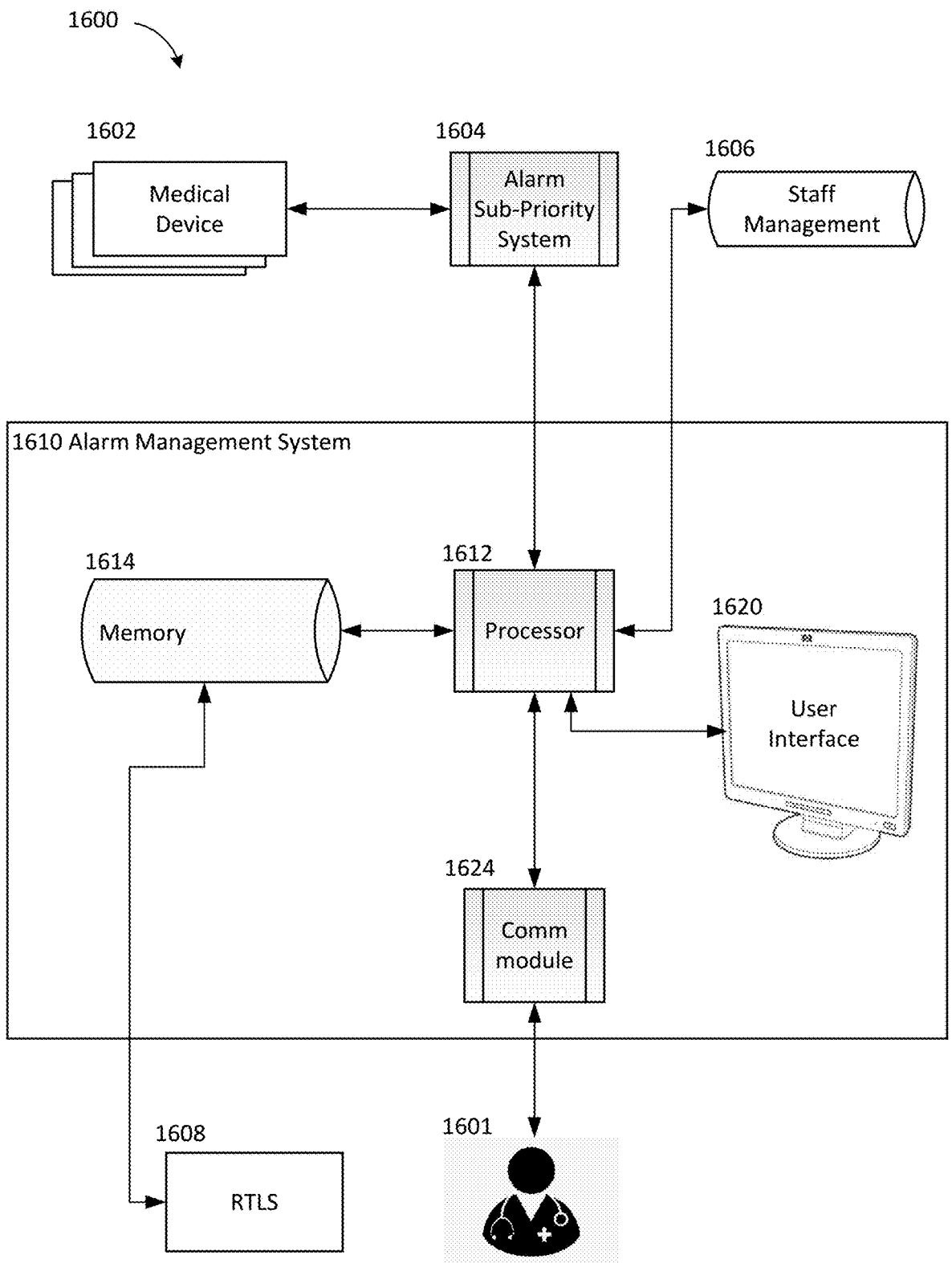
FIG. 16 is a block diagram of an exemplary alarm management system, according to certain aspects of the present disclosure.

In certain embodiments, a staff member selects a DND status on their personal device and the message is sent to the alarm management system, e.g., the processor 1612 of FIG. 16, so that alerts are not sent to this clinician until they are no longer assigned a DND status. In certain embodiments, the DND status prevents only low sub-priority alerts being sent to the staff member. In some embodiments, alerts are still sent as notifications to the staff member who is on a DND status, but the notification indicates that the alert was reassigned and sent to a different staff member. In some embodiments, the DND status is active for a predetermined period of time and after this time period expires, alerts can be sent to this clinician. In other embodiments, the staff member needs to de-select the DND status before the system can send alerts to the staff member.

Special Care

There are certain time periods during patient care in a hospital where there is an increased chance for a potentially adverse event to occur and, if resources permitting, patients require special care. Special care requires a staff member to increase the frequency of patient or vital sign monitoring, respond to alarms more quickly, order labs more frequently, or perform a device task, e.g., program a weaning protocol for ventilated patients. Clinical scenarios that may require special care include: a) dementia patients or other patients who are at an increased risk of falling, which may be exacerbated by medication; b) ventilated patients who are in the weaning stages of ventilation and have an increased risk of self-extubation or reintubation which can lead to complications, e.g., trauma, ventilator-associated pneumonia; c) patients at increased risk of sepsis wherein a patient monitoring alarm may dictate a need to change therapy or call a rapid response team.

An alarm associated with a patient under special care may be assigned an elevated sub-priority and/or require the involvement of an individual with specific skills. For example, based on the dynamic attributes disclosed previously herein in Table 1, a patient's condition may deteriorate more rapidly resulting in the alarm being assigned a higher sub-priority than a similar patient not under special care. The higher the sub-priority alarm, the more important a staff member responds in a timely fashion. It is also important that the right staff member (i.e., experience, training, etc.) responds to the alarm when special care is required and when this staff member responds measures are taken to ensure this staff member is covered for their patient tasks that do not require special care.

In certain embodiments, the system identifies a level of risk for occurrence of an adverse event for a specific patient and ranks staff members based on their dynamic attributes to provide the best odds to reduce the risk of an adverse event occurring. In certain embodiments, the system identifies the levels of risk for each of a plurality of staff members to whom the alarm could be assigned and determines the recipient of the alert associated with the alarm based in part on a comparison of these levels of risk. For example, physical capability, a psychometric aptitude to handing certain patients (e.g., delirious, dementia, etc.) are required to handling combative patients who are at an increased risk of falls and various bed exit alarms are alarming. Clinicians trained in weaning protocols and reprogramming ventilators are essential for the special care situation of monitoring weaning periods for ventilated patients.

In certain embodiments, the system reduces the burnout status of a staff member providing special care, which ensures optimal care is provided and reduces the probability of an adverse event occurring. For example, patients that require special care is part of the availability dynamic attributes of a staff member, and when the alarm management system recognizes a period when a patient requires special care, the system will increase the weighting of the workload status of the staff member providing the special care when selecting a recipient for an alert. Increasing the weighting of the designated staff member's workload status dynamic attribute score will ensure less alarms not related to the special care situation go to this staff member.

As used within this disclosure, the phrase "special control" refers to a protocol that is different from the normal operation of the facility. This can be considered as a type of special care, in that the special control reduces risk to the patient, other patients, or the staff caring for the patient. An example of a special control includes a unit dedicated to patients diagnosed with a highly contagious disease, who would be a risk to other patients and staff in a general care unit, and requiring staff to use PPE such as gowns, gloves, booties, and face shields to enter that unit. Another example is a unit dedicated to dementia patients that provides controlled access and egress to prevent patients from leaving the unit, thereby reducing the risk of harm to the patient. It may be undesirable to expect a staff member working in a special control unit to frequently respond to alarms in non-special control areas.

Ranking of Staff Members

The present disclosure describes a method and system of ranking staff members based on dynamic attributes and, based in part on this ranking, determining which staff member to send an alert associated with a medical device alarm so that a corrective action can be performed. Sending alerts based on ranking staff members based on dynamic attributes will help prevent alarm fatigue, clinician burnout, and an exodus of staff members from their jobs. Sending alerts based on a ranking of staff members based on dynamic attributes will also help prevent adverse events by ensuring the right clinician is responding in an expeditious manner and preventing lower performing staff members from committing adverse events by minimizing their workload status until they develop the capability or improve their burnout status.

The present disclosure describes seven group of dynamic attributes to determine the ranking of staff members. In this exemplary embodiment, each of the seven groups described in Table 10 are used to determine the ranking. In certain embodiments, only one group of dynamic attributes is used. In certain embodiments, two or more groups are utilized. In certain embodiments, the dynamic attributes associated with patients, as disclosed previously herein, are used to determine which staff member (e.g., a staff member having specific training to address a specific dynamic attribute of the patient) is selected to receive the alert associated with an alarm.

Table 11 shows an exemplary embodiment of assigning scores to each of the possible outcomes for a particular group of dynamic attributes. Table 11 also references the figures that show how the outcomes for some of the attribute groups from Table 10 are established using dynamic attributes. In certain embodiments, level of support is one example of how to use the staff management dynamic attribute group described in Table 10.

TABLE 11

| ATTRIBUTE | POSSIBLE OUTCOMES | FIGURE |
|---|---|---|
| Availability | Yes, Conditional, No (10, 3, DROP) | 10 |
| Capability | Yes, Limited, No (10, 5, DROP) | 11 |
| Workload | High, Medium, Low (3, 8, 10) | 12 |
| Burnout | High, Medium, Low (3, 7, 10) | 13 |
| Level of support | High, Medium, Low (5, 3, 1)) | 14 |
| Performance | High, Medium, Low (10, 8, 2) | 15 |

In certain embodiments, three scores are assigned to each attribute group. For example, for the availability attribute group of dynamic attributes, a staff member is either available, conditionally available, or not available. In certain embodiments, a greater or lesser number of outcomes and scores are used for one or more attribute groups. For example, a fourth availability outcome and score could be added to Table 11 to designate the most points to the most available person (e.g., the staff member who is available and the closest to the patient). Another availability outcome and score could be defined for a staff member in a special control environment, who may be available for alarms within this special control environment but not available, or have very limited availability, to respond to alarms in an adjacent non-special control environment.

Table 11 provides an exemplary embodiment of how the various outcomes are scored. In other embodiments, other scores or scoring systems are used. The discussion below arbitrarily selects scores for each outcome to provide an example.

The availability attributes determine if a staff member is "available" to address a medical device alarm. If a staff member is available, then 10 points are assigned to their availability score. If they are "not available," then the staff member is dropped from the scoring and ranking system until they become available again. For example, the staff member could be on break or be in a DND status making them not available. In certain embodiments, "conditionally available" falls in between available and not available on a weighted scale and more points are allocated compared to not available and less points are added compared to available. In this embodiment, 7 points is assigned to the availability score.

In certain embodiments, conditionally available means that the staff member is in a status where the system is not sending alerts to them, e.g., on break, unless the team, unit, or floor is in a dire situation and requires the assistance of this staff member. For example, if the patient to staff ratio is high for the unit and the workload status for the staff members on duty is high and the level of support is low then the alarm management system notifies the staff member on break to return to service and sends alerts shortly thereafter. In certain embodiments, if the same situation occurs and the staff member on break has a high burnout status, then the staff member is not notified to return to service and alerts would not be sent until their designated break period ends. This ensures, when possible, that staff members with a high burnout status, get periodic breaks to maintain their health and productivity.

The capability attributes determine if a staff member has the proper training, education, experience, etc. to know how to perform a corrective action to effectively address a medical device alarm. If they are "capable," 10 points is assigned to their capability score. If they are "not capable,"

then the staff member is dropped from the scoring and ranking for this particular alarm since they are not capable of responding to the alarm and may cause additional harm by responding to the alarm inadequately. In certain embodiments, "limited capability" falls in between capable and not capable on a weighted scale. In this embodiment, 7 points is assigned to the capability score.

In certain embodiments, limited capability means a staff member needs to look at supplemental information, e.g., a short video, an excerpt from a label, or interactive direction from a more-experience staff member, and then they would be capable to respond to the alarm. In certain embodiments, once a staff member who has limited capability to respond to an alarm successfully completes the supplemental training, their status is updated to capable for subsequent similar alarms. In certain embodiments, if the staff member is ranked highest amongst staff members based on dynamic attributes, that staff member will be sent the alert regardless of whether that staff member has completed the supplemental training. In some embodiments, only alarms with certain sub-priority (e.g., <M1) may be sent to staff members with a limited capability status.

The workload status attributes determine if the staff member's current workload status allows them to respond to an alert from a medical device or allows them to respond in a timely fashion. A staff member with a high workload status may take longer to respond to a medical device alarm if they have other alarms with higher alarm priorities or have critical device or patient tasks to complete. Ideally an alert would be assigned to a staff member who has a lower workload status compared to another staff member if possible. Therefore, a staff member with a lower workload status would be assigned more points to their workload status score. In the current embodiment, 3 points is assigned to a staff member with "high workload status", 8 points to a "medium workload status", and 10 points are assigned for a "low workload status".

The burnout status attributes determine if a staff member is experiencing long-term (e.g., 3-6 months) or in-shift or current (e.g., overtime) fatigue or burnout. A staff member who is experiencing alarm fatigue may not respond to alarms in a timely manner or may not respond to alarms at all. Therefore a staff member with a lower burnout status would be assigned more points to their burnout status score. In the current embodiment, 3 points are assigned to a staff member with "high burnout status", 7 points to a "medium burnout status", and 10 points are assigned to a "low burnout status".

Measures should be taken to ensure a staff member is not experiencing fatigue. Individual staff members may experience burnout or fatigue at different thresholds. The current embodiment assigns points (e.g., 3, 7, 10) universally to all staff members. In other embodiments, as dynamic attribute data is collected and analyzed to determine thresholds for high, medium and low burnout status for a particular staff member, custom scoring will ensure that staff members with a higher proclivity towards experiencing burnout will have higher burnout scores for each level versus a staff member less inclined to experience burnout. For example, a staff member who temporarily has a stressful private life (e.g., going through a divorce) may have dynamic attributes that suggest they have less of a threshold to experience burnout on the job. In other embodiments, these adjustments to the burnout scores for these specific individuals is implemented on a temporary basis so not to be inequitable to other staff members who have a higher threshold for burnout and cause them to burnout.

As depicted in Table 10, certain embodiments will track the burnout status dynamic attributes of a staff member to ensure the number of alarms they respond to, the amount of time they work while having a high workload status, the amount of hours they work during a shift or between vacations is managed so staff members do not experience alarm fatigue or burnout, which if not managed, more cause them to leave their job.

Attributes associated with level of support determine if a staff member who may need support (e.g., high workload and/or burnout status) has support from nearby staff members. Staff members who provide support may be assigned backup staff members or unassigned staff members. In some embodiments, the alarm management system uses assigned backups (e.g., a nurse has one or more assigned backup nurses to take alerts from her when needed). In other embodiments every staff member in the same unit, same floor, or same hospital could be considered a back-up to a nurse, although not would all be capable of responding to all the alerts the nurse may be capable of responding to. Level of support determines if the assigned or unassigned backups are available, capable and have workload and burnout status that allows them to provide support.

If a staff member has a low backup score, then it means that staff member may have to be assigned an incoming alert regardless of if they need support (e.g., have a high workload status and/or a high burnout status). In this situation, the staff member would need to prioritize which alert is most important to respond to next (e.g., which alert has the highest sub-priority).

A staff member with a lower level of support would be assigned more less points to their level of support score since sending them alerts may affect their ability to respond to alerts from their patients or current workload. In the current embodiment, 5 points is assigned to a staff member with high level of support, 3 points to a medium level of support, and 1 point are assigned for a low level of support.

The dynamic attributes associated with level of support are helpful for staff management when deciding if additional personnel are needed to staff a particular shift. If staff members under their supervision have high workload and/or high burnout statuses and the level of support is low, then the staff manager calls or the alarm management system disclosed previously herein notifies additional resources to come in and assist the current staff. These additional resources may be internal resources (e.g., staff members on break, staff members working in other units, etc.) or external resources (e.g., a staff member comes in early for their next shift, a stand-by staff member comes in, etc.). An additional resource may also include using a "floater" or a staff member whose primary job is to respond to alarms to reduce the burden of alarm fatigue on staff members who are assigned patients.

The performance attributes determine if a staff member is performing well responding to alarms in a timely fashion and providing care for their patients to limit adverse events and complaints. Staff members with low performance would be assigned less points to their performance score. In the current embodiment, 10 points is assigned to a staff member with high performance, 8 points to a medium performance, and 2 points are assigned for a low performance.

The performance score, calculated over a given period, determines if the other dynamic attribute groups are optimized to limit the number of never events, adverse events, complaints, etc. A staff member with a low performance score may need additional training, training reinforced more often, or may be experiencing a burnout status at a lower threshold then previously scored. Performance of an individual staff member may also be caused by team dynamics. For example, the hospital may be understaffed and therefore the availability of highly capable members to respond to alerts may be affected resulting in lower performance scores.

In certain embodiments corrective actions can be performed using dynamic attributes to increase the performance of the staff member and/or reduce the potential harm to patients until the performance of this staff member improves. For example, for a staff member with a low performance score, the system assigns alerts associated with medical alarms with lower alarm priorities or sub-priorities to the low-performing staff member until their performance improves.

In certain embodiments, a staff member with a low performance score has certain workload dynamic attributes adjusted to limit adverse events. For example, the workload status dynamic attribute, number of patients with a high health assessment scores of the assigned patients, is adjusted so more patients with a lower acuity score are assigned to staff members with a low performance attribute. Limiting the number of patients with a high acuity score assigned to a low-performing staff member may be beneficial until they improve their performance score by other dynamic attributes, e.g., more frequent training on medical devices to increase knowledge retention.

Table 12 shows an exemplary embodiment of ranking staff members by using six groups of attributes discussed above to determine who should receive an alert associated with a medical device alarm. In this embodiment, a weighed system is used where the total score for each staff member is the sum of each attribute score, calculated by multiplying the weight of attribute by the value of that attribute (conventional weighted-choice matrix) as defined in Table 11. Certain attribute outcomes, e.g., a not available or not capable status, cause a staff member to be scored as not available regardless of other attributes and they are not available to receive an alert.

Table 12 shows an exemplary embodiment for ranking five staff members for responding to an H1 or high priority alarm. The weights show for a H1 alarm, the capability score has the highest weight, followed by availability and workload status, and then the scores associated with performance, burnout status and level of support. The staffs capability, availability and workload status are the most important for responding to a H1 sub-priority alarm since injury can occur if alarm condition is not responded to correctly and/or in a timely fashion.

TABLE 12

| ATTRIBUTE | WEIGHT | STAFF MEMBER | | | | |
| --- | --- | --- | --- | --- | --- | --- |
| | | A | B | C | D | E |
| Availability | 10 | DROP | 10 | 10 | 10 | 10 |
| Capability | 20 | 10 | 5 | 10 | DROP | 10 |
| Workload | 10 | 8 | 10 | 8 | 10 | 3 |
| Burnout | 6 | 10 | 7 | 3 | 7 | 7 |
| Level of support | 0 | 3 | 5 | 3 | 3 | 3 |
| Performance | 7 | 8 | 8 | 8 | 10 | 10 |
| | SCORE | na | 398 | 454 | na | 442 |

Table 12 shows Staff Member A is not available, Staff Member D is not capable, and therefore, both are dropped from the ranking. Staff Member C has the highest score and therefore would get the alert associated with this H1 or high priority alarm.

In Table 12, Staff Member B had the lowest score since they had a limited capability (e.g., five points) and in this embodiment H1 alarms put a premium score on capability. Staff Member D had the second highest score because they had a high workload status (e.g., 3 points) and sending them to respond to H1 alarm is difficult with their current high workload. Staff Member C had a high burnout status (3 points) however they had only a medium workload status. Since the higher weight was placed on workload status versus burnout status this alert was sent to the staff member with the higher burnout status. If staff member C also had a high workload status, then they would have a lower score then Staff Member E and would not get the alert. In certain embodiments, the algorithm uses a different weight for an H1 sub-priority compared to other sub-priorities.

Table 13 shows the ranking of staff members for a M2 sub-priority alarm or medium priority alarm. The staff members in Table 13 have the same attribute scores as the staff members in Table 12, however the weights are scored differently for a M2 sub-priority alarm. Since a M2 sub-priority alarm or medium priority alarm can result in a lot less potential harm than an H1 sub-priority alarm and the staff member has a lot more time to respond to the alarm, less weighting is placed on availability and capability.

TABLE 13

| ATTRIBUTE | WEIGHT | STAFF MEMBER | | | | |
| --- | --- | --- | --- | --- | --- | --- |
| | | A | B | C | D | E |
| Availability | 5 | DROP | 10 | 10 | 10 | 10 |
| Capability | 5 | 10 | 5 | 10 | DROP | 10 |
| Workload | 8 | 8 | 10 | 8 | 10 | 3 |
| Burnout | 4 | 10 | 7 | 3 | 7 | 7 |
| Level of support | 3 | 3 | 5 | 3 | 3 | 3 |
| Performance | 3 | 8 | 8 | 8 | 10 | 10 |
| | SCORE | na | 222 | 209 | na | 191 |

In this embodiment, Table 13 shows Staff Member B has the highest score and will receive the alert to respond to the alarm. Although Staff Member B has a limited capability (e.g., 5 points), they have a low workload status and hence have the time to respond to the lower risk alarm. Limited capability for a such a low priority alarm allows the staff member to get supplementary information (e.g., short instruction) on their mobile phone to learn how to respond to the alarm. Sending the alert to Staff Member B takes work away from Staff Member C, who has a high burnout status, and Staff Member E, who has a high workload status. Therefore, alarm fatigue and clinician burnout are reduced for the staff.

As demonstrated in Tables 12 and 13, certain embodiments will customize the weighting system for the priority or sub-priority of the alarm. In other embodiments, the weighting system is tailored for the specific type of alarm (e.g., occlusion alarm for a specific type of medicine). In other embodiments, the weighted system implements a time dependent approach when staff management want to utilize working breaks or less stressful periods for staff members with a high burnout status. For example, if the goal is to give Staff Member C with a high burnout status, fifteen minutes of a working break, then the weights for burnout status would change accordingly. In other embodiments, other scoring systems are used other than a weighting system for the dynamic attribute groups.

Figure 9:
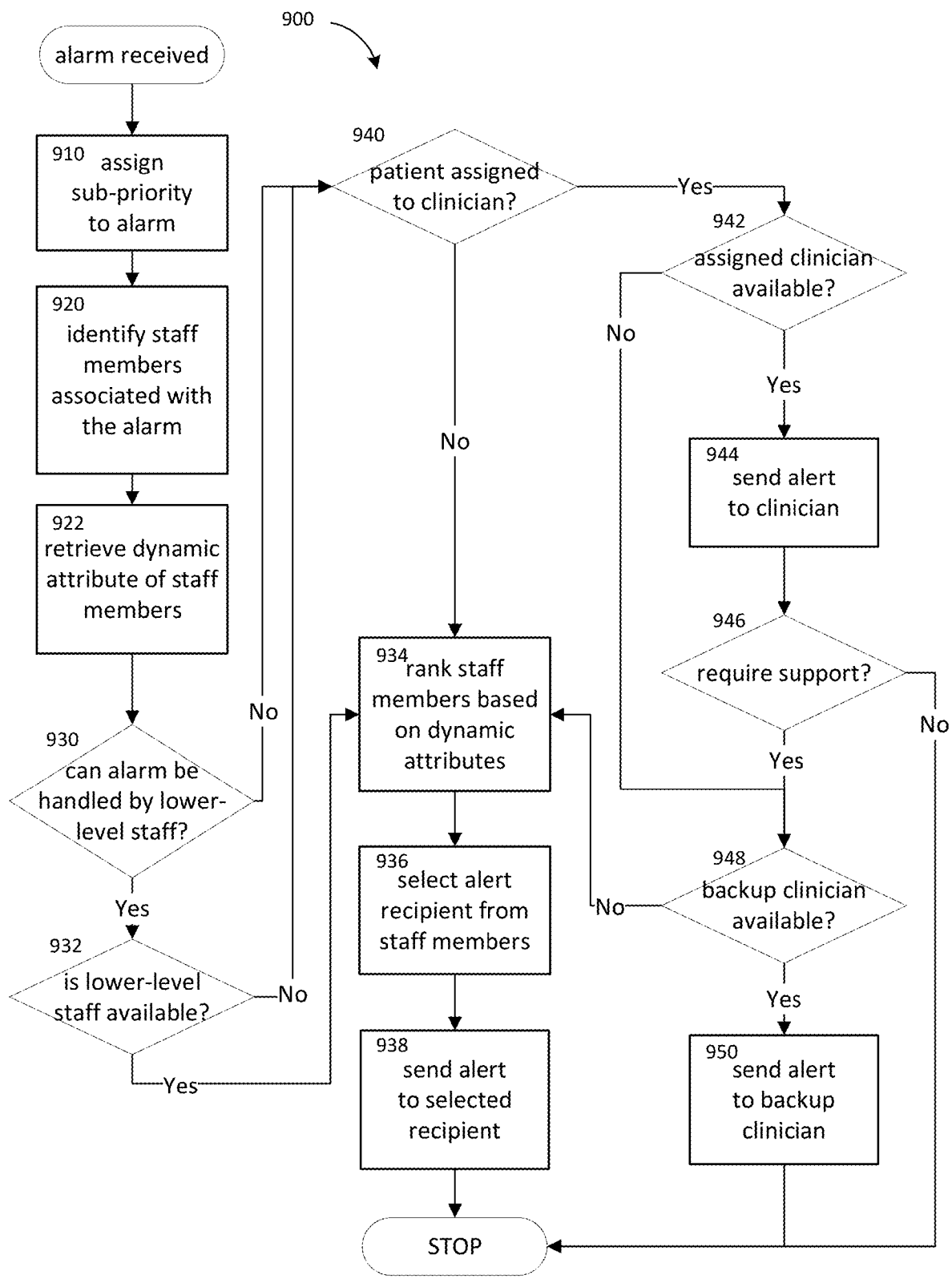
FIG. 9 is a flowchart of an exemplary embodiment of a workflow to select an alert recipient based in part on a dynamic attribute of a staff member, according to certain aspects of the present disclosure.

FIG. 9 is a flowchart of an exemplary embodiment of a workflow 900 to select an alert recipient, according to certain aspects of the present disclosure. The workflow 900 starts when an alarm is received, e.g., from a medical device, and proceeds to step 910 wherein a sub-priority is assigned, for example as described with respect to FIGS. 3A-3B. In certain embodiments, step 910 is omitted and a sub-priority is not assigned, wherein a conventional priority, e.g., as determined by the medical device manufacturer and/or provided by the medical device, is used in lieu of a sub-priority wherever processes disclosed herein refer to a sub-priority. The workflow 900 proceeds to step 920 that identifies staff members associated with the alarm, e.g., staff members assigned to care for the patient, staff members having specific training with the medical device issuing the alarm, and staff members who are presently working and/or proximate to the location of the medical device, etc.

The workflow 900 retrieves at least one dynamic attribute associated with one or more of these staff members in step 922. The dynamic attribute is selected from a group of attributes (e.g., availability, capability, workload status, burnout status, etc.). Step 930 determines if the alarm can be handled by a lower-level staff member and, if so, step 932 determines if such staff member is available. If lower-level staff members are available, then step 934 ranks them in part based on their dynamic attributes. Step 936 selects a recipient from the staff members. Step 938 sends an alert associated with the alarm to the selected recipient. In certain embodiments, the ranking algorithm includes weighting of the dynamic attributes.

If either the alarm cannot be handled by a lower-level (e.g., having a lower role as defined in Table 2) staff member, or an appropriate lower-level staff member is not available, then step 940 determines if the patient associated with the alarm is assigned to a clinician. If no, then the process continues to steps 934, 936 and 938 as described above. If yes, step 942 determines if the assigned clinician is available and, if yes, step 944 sends an alert to the assigned clinician. If the assigned clinician is not available, then step 948 determines if an assigned backup clinician is available. If yes, then step 950 sends the alert to the assigned backup clinician.

Step 946 determines if the assigned clinician needs support, e.g., their workload status and/or burnout status is high. If the clinician does not need support, then the process ends. If the clinician needs support, then step 948 determines if an assigned backup clinician is available. If yes, then step 950 sends the alert to the assigned backup clinician.

In certain embodiments, one or more of steps 938, 944 and 950 further comprise an assessment of alarms previously assigned to the selected staff member that are not yet resolved, i.e., active alarms. In certain embodiments, the new alert comprises a ranking of all active alarms that are assigned to the staff member to aid the staff member by allocating their time and managing the alarms in a priority order.

In certain embodiments, one or more of steps 938, 944 and 950 further comprise a re-assignment of one or more previously assigned alarms from the selected staff member to one or more other staff members. This enables the selected staff member to handle the new alarm, which may have a higher sub-priority or may require special skills of the selected staff member. In certain embodiments, the one or more of the previously assigned alarms may be handled by a lower-level staff member, thus freeing up the selected senior staff member to handle the new alarm. In certain embodiments, the new alert comprises a notification that at least one of the prior alarms has been re-assigned to another staff member.

In certain embodiments, one or more of steps 938, 944 and 950 further comprise tracking whether the assigned staff member responds to the provided alert, either by an acknowledgement or by resolution of the associated alarm. In certain embodiments, one or more of steps 938, 944 and 950 further comprise a repeated transmission of the alert to the same staff member after a pre-defined time period. In other embodiments, if the designated staff member does not acknowledge the alert or does not respond to it, then one or more steps of 938, 944, and 950 selects an alternate staff member based on ranking the dynamic attributes of the remaining staff members and reassigns or sends this alert to this alternate staff member. In other embodiments, if the designated staff member acknowledges the alert but has not responded to the alert after a predefined period, then the sub-priority of the alarm associated with the alert escalates as previously described herein.

If step 948 determines the assigned backup clinician is not available, then the process continues to steps 934, 936 and 938 and sends an alert to a different staff member selected based in part on an evaluation of their dynamic attributes. In certain embodiments, if the assigned clinician is sent an alert, they need support, and the alert is reassigned to another staff member then the original alert is modified with the new staff member that the alert was reassigned to handle the alarm. In certain embodiments, there are no assigned backup staff members and steps 948 and 950 are not present. In this situation, if the assigned clinician is not available in step 942 or the assigned clinician needs support in step 946, then the process continues to steps 934, 936 and 938 and sends an alert to a different staff member selected based in part on their dynamic attributes.

Determining Outcomes and Scores of Dynamic Attribute Groups

Figure 10:
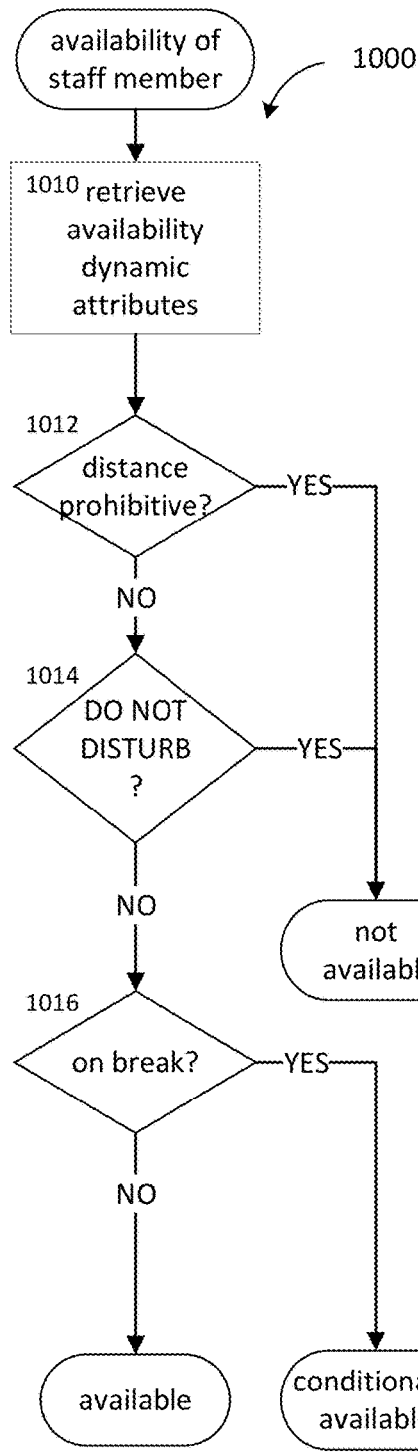
FIG. 10 is a flowchart of an exemplary embodiment of a workflow to determine an availability of a staff member, according to certain aspects of the present disclosure.

FIG. 10 is a flowchart of an exemplary workflow 1000 to determine the availability of a staff member, according to certain aspects of the present disclosure. The workflow 1000 starts at step 1010 that retrieves one or more of the staff member's availability dynamic attributes, e.g., location or DND status. Step 1012 determines if the staff member's distance from the medical device that sent the alarm, the time that it will take for the staff member to reach the medical device and compare this time to a threshold. If the distance is above the threshold, e.g., the staff member is on the other side of the unit, then their availability is determined to be "not available."

If the distance is not prohibitive, step 1014 determines the DND status of the staff member and assigns the member's availability as not available if the DND status is yes. If the DND status is "no," then step 1016 determines if the staff member is on break. If they are on break, then their availability status is "conditionally available." If they are not on break, then their availability status is "available."

Figure 11:
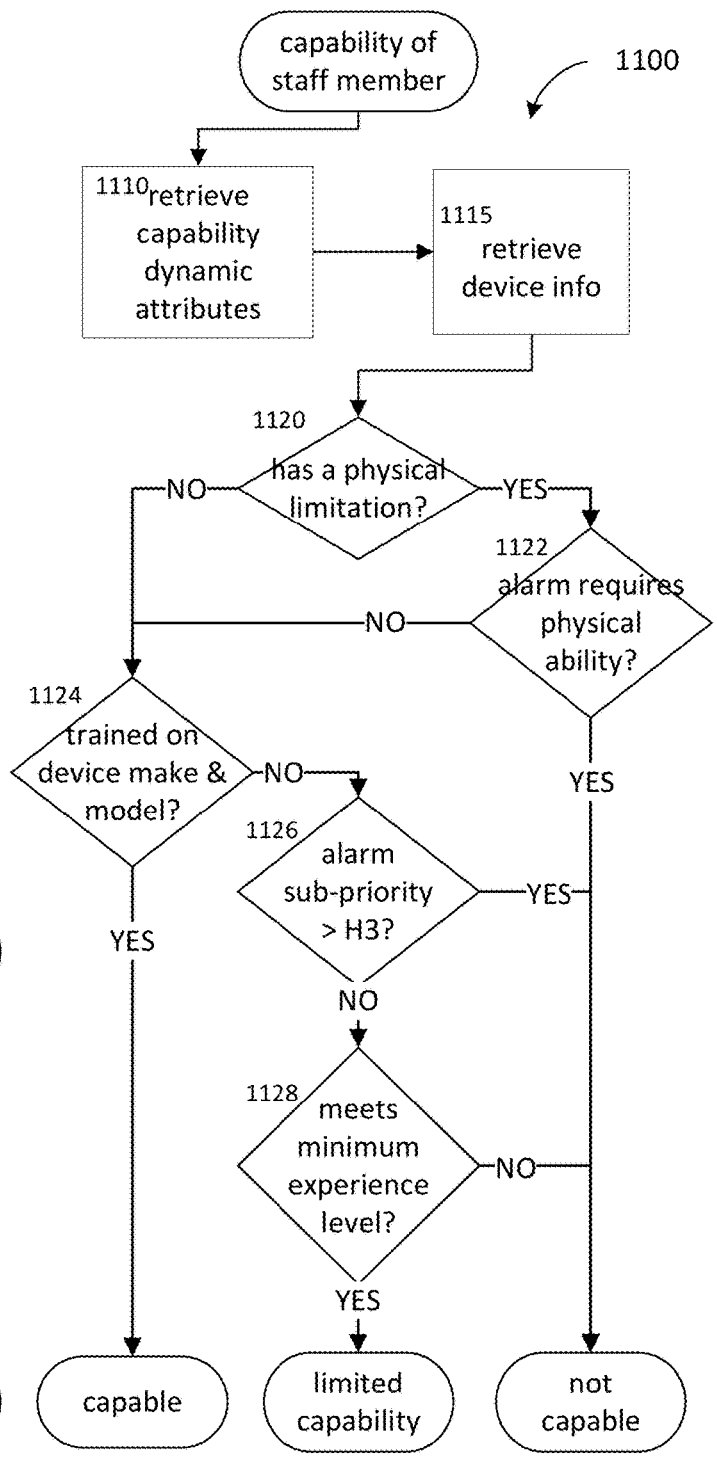
FIG. 11 is a flowchart of an exemplary embodiment of a workflow to determine a capability of a staff member, according to certain aspects of the present disclosure.

FIG. 11 is a flowchart of an exemplary embodiment of a workflow 1100 to determine the capability of a staff member, according to certain aspects of the present disclosure. The process starts at step 1110 that retrieves a capability dynamic attribute of one or more staff members (e.g., education, experience, training, physical capabilities, etc.). The process continues at step 1115 and retrieves information associated with the device that issued the alarm (e.g., make, model, etc.).

Step 1120 determines if a staff member has a physical limitation and step 1122 determines if the alarm requires a specific level of physical ability. For example, an alarm associated with a patient falling from a hospital bed requires the staff member to have the physical strength and ability to assist or lift the patient from the floor. If a staff member has a physical limitation and does not have the required ability to handle the alarm condition, then the staff member is determined to be "not capable" of responding to this alarm.

If either the staff member does not have a physical limitation or the alarm does not require physical ability to resolve, then the process continues to step 1124 and determines if the staff member is trained on the make and model of the medical device that has issued the alarm. If they are trained, then they are determined to be "capable" of responding to the alarm. If they are not trained on the device or if they are not trained on the particular device alarm, then step 1126 determines if the alarm sub-priority is a high priority (e.g., >H3), and if so, then the staff member is determined to be not capable of responding to the alarm. For example, a sub-priority>H3 requires a fast response time and therefore, a staff member will not have time to look at supplemental information.

If step 1126 determines the alarm sub-priority is low enough, then step 1128 determines if the staff member meets a minimum amount of experience to handle an alarm. For example, the minimum amount of experience may be either two years working experience or experience working with a similar medical device. If step 1128 determines they do meet the minimum experience, then they are determined to have "limited capability," otherwise they are determined to be not capable.

Figure 12:
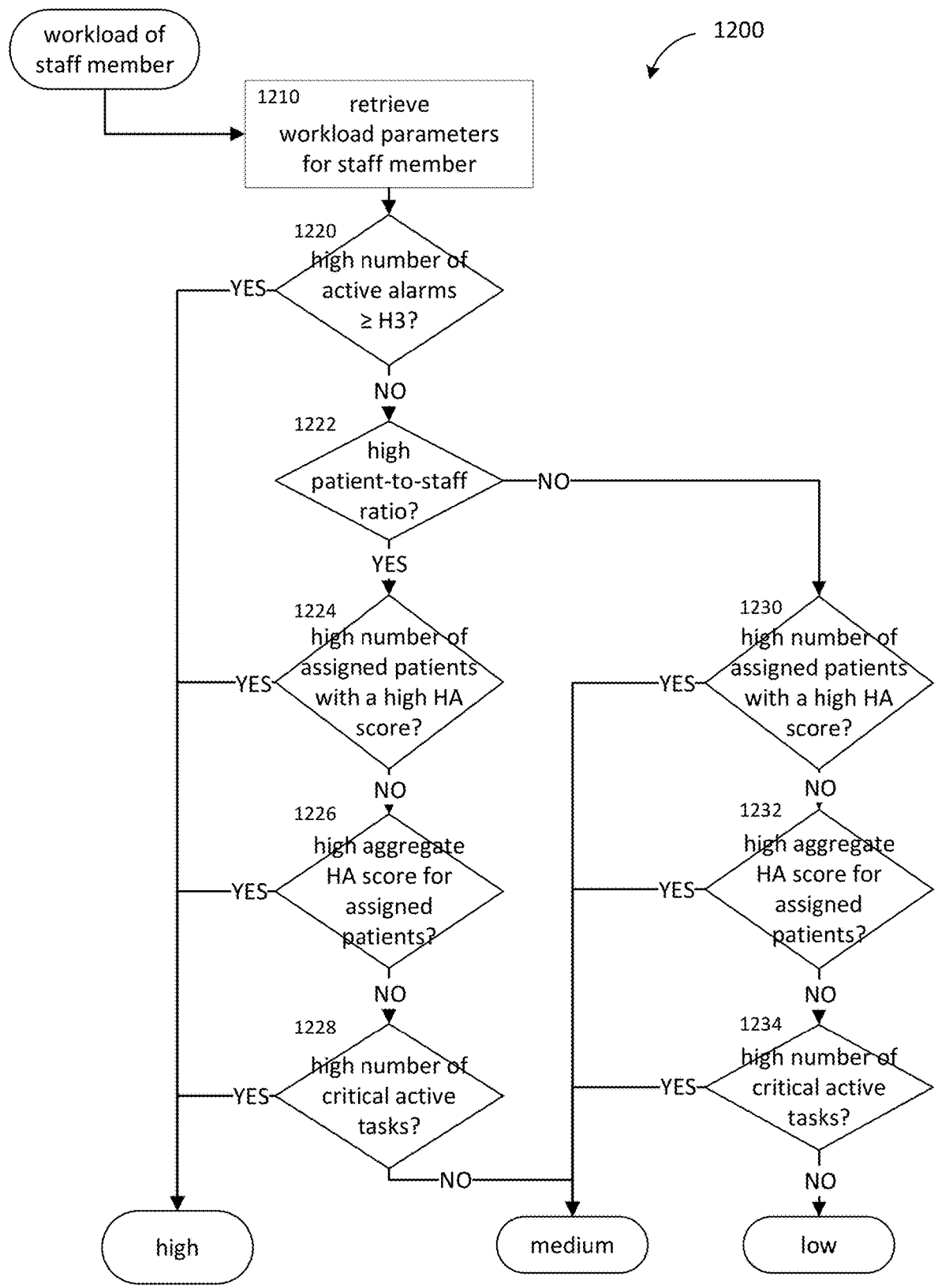
FIG. 12 is a flowchart of an exemplary embodiment of a workflow to determine a workload of a staff member, according to certain aspects of the present disclosure.

FIG. 12 is a flowchart of an exemplary embodiment of a workflow 1200 to determine the workload status of a staff member, according to certain aspects of the present disclosure. The workflow 1200 starts at step 1210 that retrieves the workload status dynamic attributes associated with the staff member (e.g., number of active alarms in queue, current patient-to-staff ratio, total aggregate of patient health assessment scores associated with the patients assigned to the staff member, etc.).

Step 1220 determines whether the staff member has a high number of active alarms having sub-priorities that are >=H3. If yes, then the staff member's workload status is determined to be high. In certain embodiments, alarm priorities are used in place of alarm sub-priorities. If no, step 1222 determines whether the staff member is assigned a patient-to-staff ratio that exceeds a pre-determined value. In certain embodiments, this value is set by the hospital. In certain embodiments, this value is set according to the unit in which the staff member is working. For example, a 2:1 patient to staff ratio may be considered high for an intensive care unit but would be considered low for a medical floor. In certain embodiments, this value is set by another agency, for example a government oversight organization.

If step 1222 is answered affirmatively, then step 1224 determines whether the clinician has a number of assigned patients having a patient health assessment score that is above a pre-determined value. If yes, then the staff member's workload status is determined to be high. If no, the process proceeds to step 1226 and determines whether the clinician has a high total patient health assessment aggregate score for their assigned patients. If yes, then their workload status is determined to be high.

If step 1226 determines the staff member does not have a high aggregate patient health assessment score for their patients, then process proceeds to step 1228 and determines whether the clinician has a high number of active tasks (e.g., device and/or patient tasks). If yes, then their workload status is determined to be high and, if no, then their workload status is determined to be medium.

If step 1222 determines a clinician does not have a high patient to staff ratio, then if any of steps 1230, 1232, and 1234, are answered affirmatively, the staff member is assigned a medium workload status designation. If each of these steps are answered negatively, then a staff member is assigned a low workload status designation.

Figure 13A:
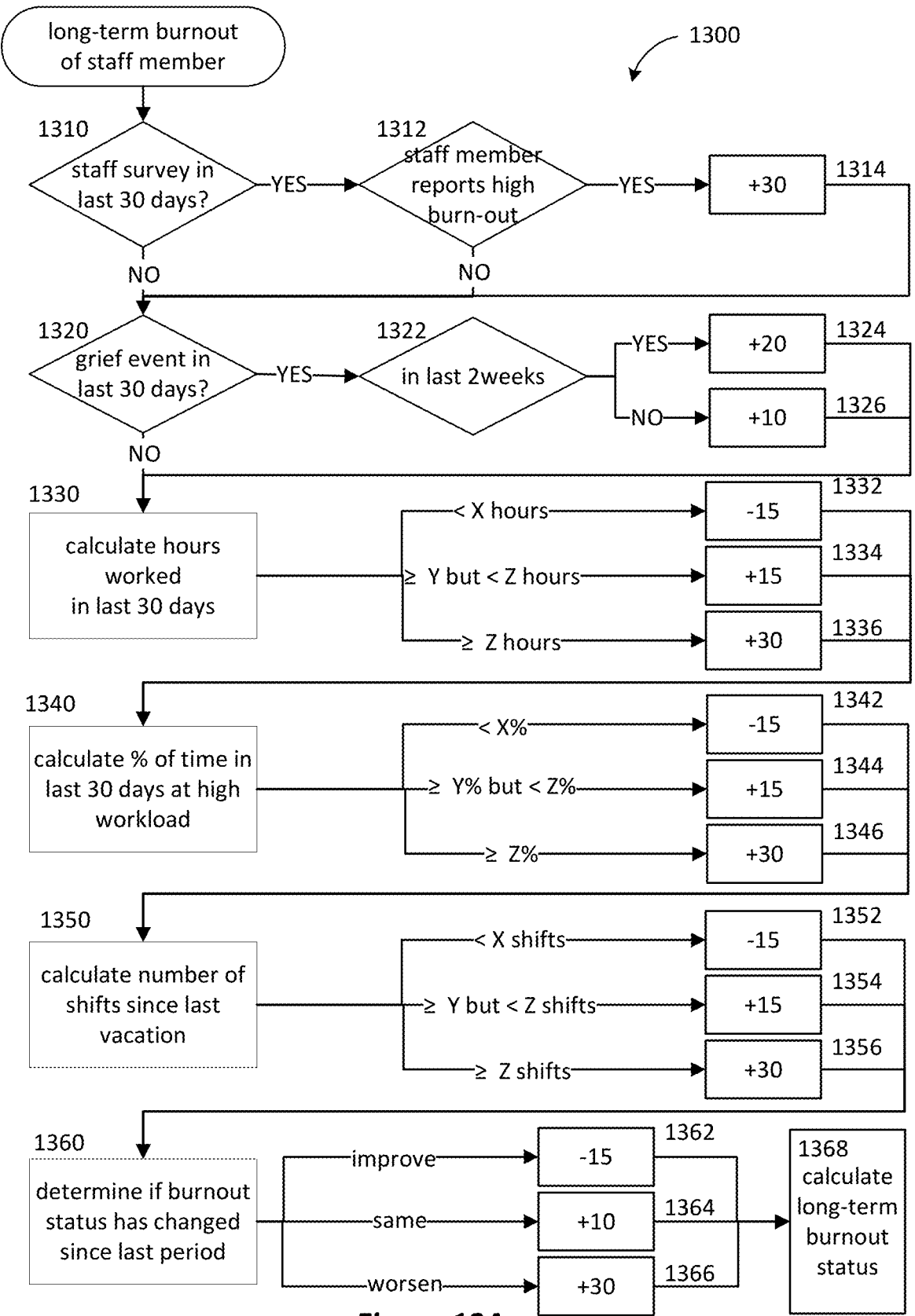
FIGS. 13A-13B are flowcharts depicting exemplary embodiments of a workflow to determine a burnout status of a staff member, according to certain aspects of the present disclosure.

FIG. 13A is a flowchart depicting an exemplary embodiment of a workflow 1300 to determine a long-term burnout status of a staff member, according to certain aspects of the present disclosure. A staff member's long-term burnout status is calculated over a defined period (e.g., 30 days, 90 days, 1 year, etc.). The point values are additive as the workflow is executed and the cumulative score is calculated in steps 1368.

Figure 13B:
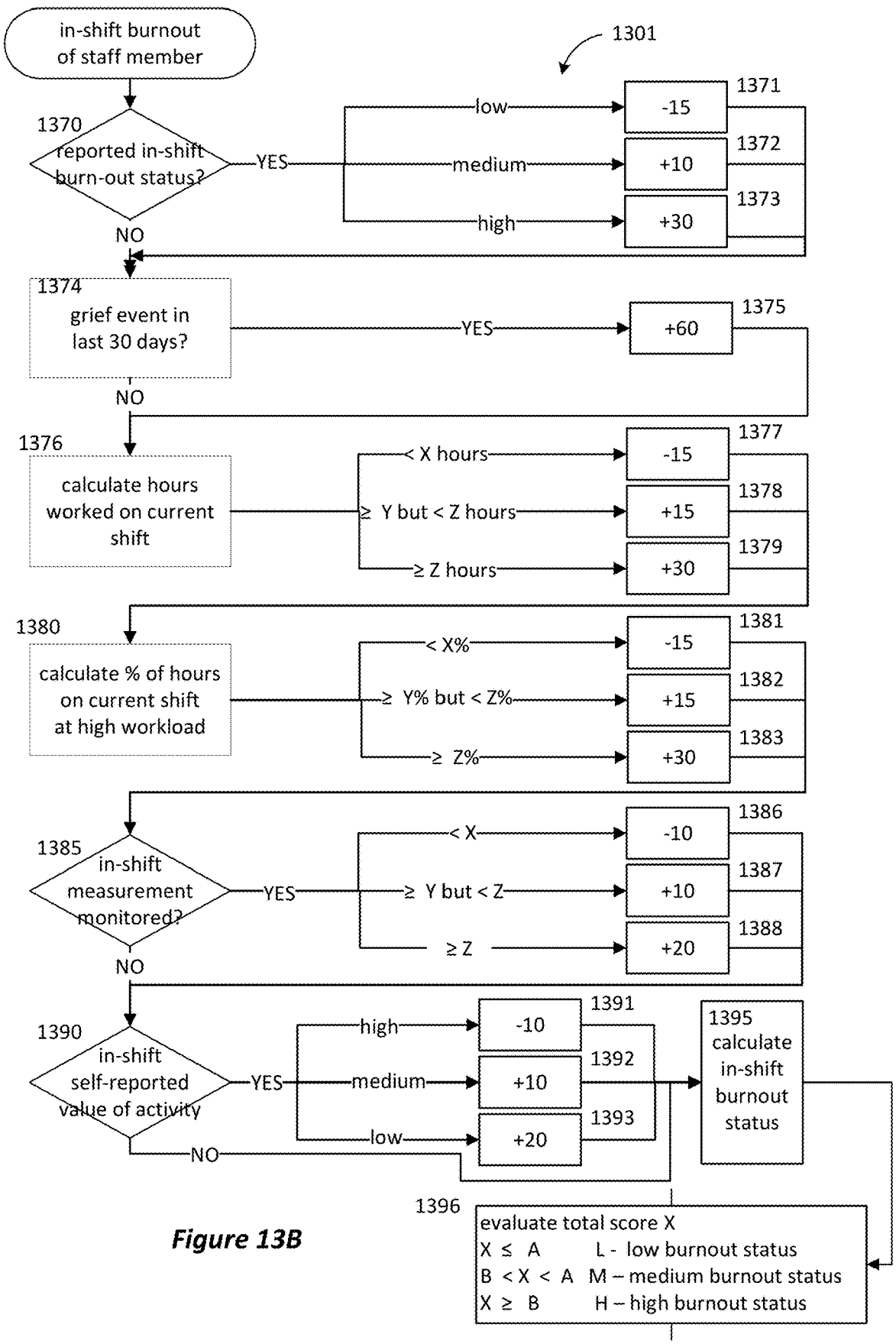

FIG. 13B is a flowchart depicting an exemplary embodiment of a workflow 1301 to determine the in-shift burnout status of a staff member. The cumulative value calculated in step 1368 in FIG. 13A is carried over to FIG. 13B and used to determine the in-shift burnout status of a staff member. The current burnout status, e.g., when a medical device alarms, of a staff member is the summation of the long-term burnout status and the in-shift burnout status using the dynamic attributes associated with both. In other embodiments only the long-term burnout status is used or only the in-shift burnout status is used.

The points associated with each of the steps in FIGS. 13A and 13B are illustrative and other scores, both positive and negative, can be used for any dynamic attribute associated with the burnout status of a staff member. In some embodiments, points associated with dynamic attributes are added on a sliding scale, e.g., additional points per event or duration. In certain embodiments, each occurrence of the dynamic attributes monitored over the period are added together to calculate the cumulative score. In certain embodiments, a threshold is defined for each dynamic attribute for a burnout status and points are assigned depending on whether the threshold was exceeded or not.

The process starts at step 1310 that determines whether a staff survey was completed by the staff member in the last 30 days. If a survey was completed, then step 1312 determines if the staff member reported a high burnout status. If yes, then step 1314 adds 30 points to the cumulative score and proceeds to step 1320. If the staff member did not complete a survey in step 1310 or did not report a high burnout status in step 1312, or step 1314 assigned points, then the workflow 1300 branches to step 1320.

Step 1320 determines whether a grief event was reported by the staff member in the last 30 days. Step 1322 determines if this event occurred in the prior two weeks. If "yes," then step 1324 adds 20 points. If "no," then step 1326 adds 10 points. If no grief event was reported in step 1320 or steps 1324 or 1236 assigned points, then the workflow branches to step 1330.

Step 1330 calculates the number of hours worked by the staff member in the last 30 days. If the staff member worked less than X hours, then step 1332 subtracts 15 points from the cumulative score. If the staff member worked greater than or equal to Y but less than Z hours, then step 1334 adds 15 points. If the staff member worked greater or equal to Z hours, then step 1336 adds 30 points to the cumulative score.

Step 1340 determines the percentage of time in the last 30 days that a staff member worked time that was classified as a high workload status. Step 1342 subtracts 15 points if the percentage of time is less than X %, step 1344 adds 15 points if the percentage is greater than or equal to Y % but less than Z %, and step 1346 adds 30 points if the percentage is greater or equal to Z %.

Step 1350 determines the number of shifts the staff member worked since their last vacation. Step 1352 subtracts 15 points if the number of shifts is less than X, step 1354 adds 15 points if the number of shifts is greater than or equal to Y but less than Z, and step 1356 adds 30 points if the number of shifts is greater or equal to Z shifts. In certain embodiments, additional points are added for every additional shift past Y shifts, e.g., additional 0.5 points per shift.

Step 1360 determines if the staff member's long-term burnout status has improved when compared to the last period where the burnout status was calculated for the staff member. If the burnout status has improved, step 1362 subtracts 15 points. If the burnout status has stayed the same, step 1364 adds 10 points. If the burnout status has worsened, step 1366 adds 30 points.

Step 1368 accumulates the points from each of the previous steps to determine the long-term burnout status for the staff member.

The process continues to FIG. 13B where workflow 1301 determine an in-shift burnout status of a staff member, according to certain aspects of the present disclosure. Step 1369 adds the long-term burnout status from step 1368 of FIG. 13A.

Step 1370 determines if the staff member reported an in-shift burnout status. If a survey was reported in-shift, step 1371 subtracts 15 points for a low burnout status, step 1372 adds 10 points for a medium burnout status, and step 1373 adds 30 points for a high burnout status. If no in-shift survey was completed on the current shift or steps 1371, 1372, or 1373 assigned points then the process branches to step 1374.

Step 1374 determines whether a grief event occurred on the current shift. If yes, step 1375 adds 60 points and continues to step 1376, and if no, then no points are added and the process branches directly to step 1376.

Step 1376 calculates the number of hours worked by the staff member in the current shift up to the point the calculation needs to be performed (e.g., a new alarm is received). If the staff member worked less than X hours, then step 1377 subtracts 15 points from the cumulative score. If the staff member worked greater than or equal to Y but less than Z hours than step 1378 adds 15 points. If the staff member worked greater or equal to Z hours, then step 1379 adds 30 points to the cumulative score.

Step 1380 determines the percentage of time worked by the staff member in the current shift up to the point where the calculation needs to be performed (e.g., a new alarm is received) that was classified as a high workload status. Step 1381 subtracts 15 points if the percentage of time is less than X %, step 1382 adds 15 points if the percentage is greater than or equal to Y % but less than Z %, and step 1383 adds 30 points if the percentage is greater or equal to Z %.

Step 1385 determines if an in-shift measurement is monitored for the staff member. An in-shift staff member measurement can be a health measurement, e.g., blood pressure, an activity measurement, e.g., number of steps taken during the shift, or a quality-of-life measurement, e.g., number of hours slept since the previous shift. If one or more of these measurements are being recorded, then step 1386 subtracts 10 points if the measurement is less than X. If the measurement is greater than or equal to Y but less than Z, then step 1387 adds 10 points. If the measurement is greater than or equal to Z, then step 1388 adds 20 points to the cumulative score. If no in-shift measurement is being monitored or points were assigned by steps 1386, 1387, or 1389, then workflow 1301 branches to step 1390.

Step 1390 determines if the staff member is self-reporting a health value (e.g., blood pressure), an activity value (e.g., medication compliance) or a quality-of-life value (e.g., number of hours slept from the previous shift). If one or more of these values are being self-reported, then step 1386 subtracts 10 points if the value is less than X. If the value is greater than or equal to Y but less than Z, then step 1392 adds 10 points. If the value is greater than or equal to Z, then step 1393 adds 20 points to the cumulative score. In certain embodiments, if the staff member did not take their medication (e.g., an anti-depressant) then K number of points are added. If no activity is self-reported or points were assigned by steps 1391, 1392, or 1393 then workflow 1301 branches to step 1395.

Step 1395 tallies all the points and calculates a cumulative score, X. Step 1396 assigns one of three burnout status outcomes based on the value. If X is less than or equal to a first threshold A, then the burnout status is "low." If X is between A and a higher second threshold B, then the burnout status is "medium." If X is greater than or equal to B, then the burnout status is "high."

In certain embodiments, the value used to determine current burnout status is determined by adding the long-term burnout score from workflow 1300 of FIG. 13A to the cumulative value calculated in workflow 1301. In certain embodiments, either just the long-term burnout status calculated in FIG. 13A or the in-shift burnout status calculated in FIG. 13B is used as the current burnout status for the alarm management system.

Figure 14:
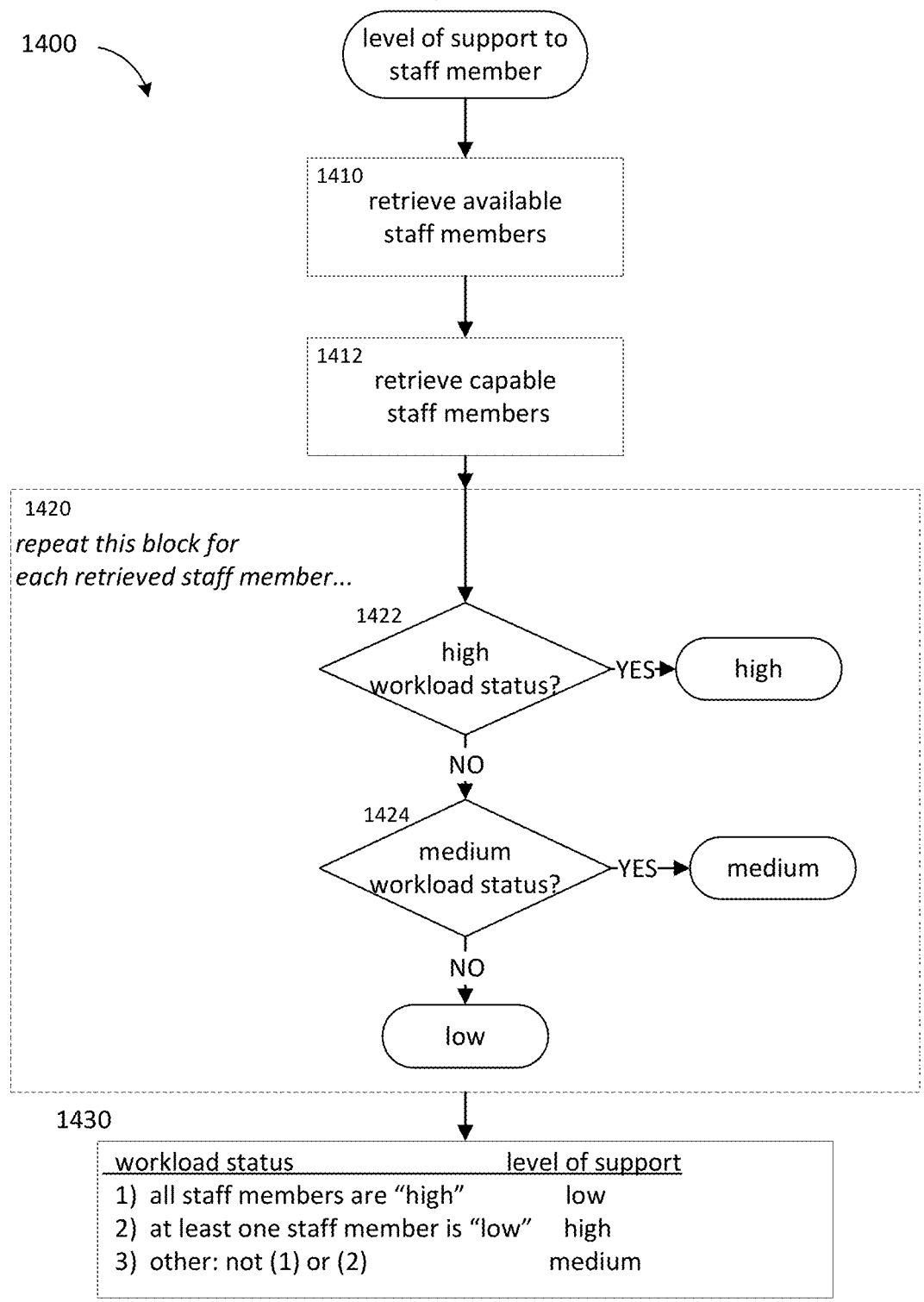
FIG. 14 is a flowchart of an exemplary embodiment of a workflow to determine a level of support for a staff member, according to certain aspects of the present disclosure.

FIG. 14 is a flowchart of an exemplary embodiment of a workflow 1400 to determine a level of support for a staff member, according to certain aspects of the present disclosure. The process starts at step 1410 that retrieves the available staff members who may provide support to the staff member requiring support. Step 1412 retrieves the staff members capable of responding to the alarm.

For each staff member who is determined to be available and capable, step 1420 retrieves their workload status. Step 1422 assigns a score of high for a high workload status. If not a high workload status, then step 1424 assigns a medium for a medium workload status and a low for a low workload status. In certain embodiments, burnout status is also used to calculate the level of support for a staff member.

Step 1430 determines the level of support for a staff member by the following criteria:
1) if all available and capable backup staff members have a high workload status then the level of support is "low"
2) If at least one of these staff members has a low workload status, then the level of support is "high"
3) If neither criterion 1 nor 2 is true, then the level of support is "medium"

Figure 15:
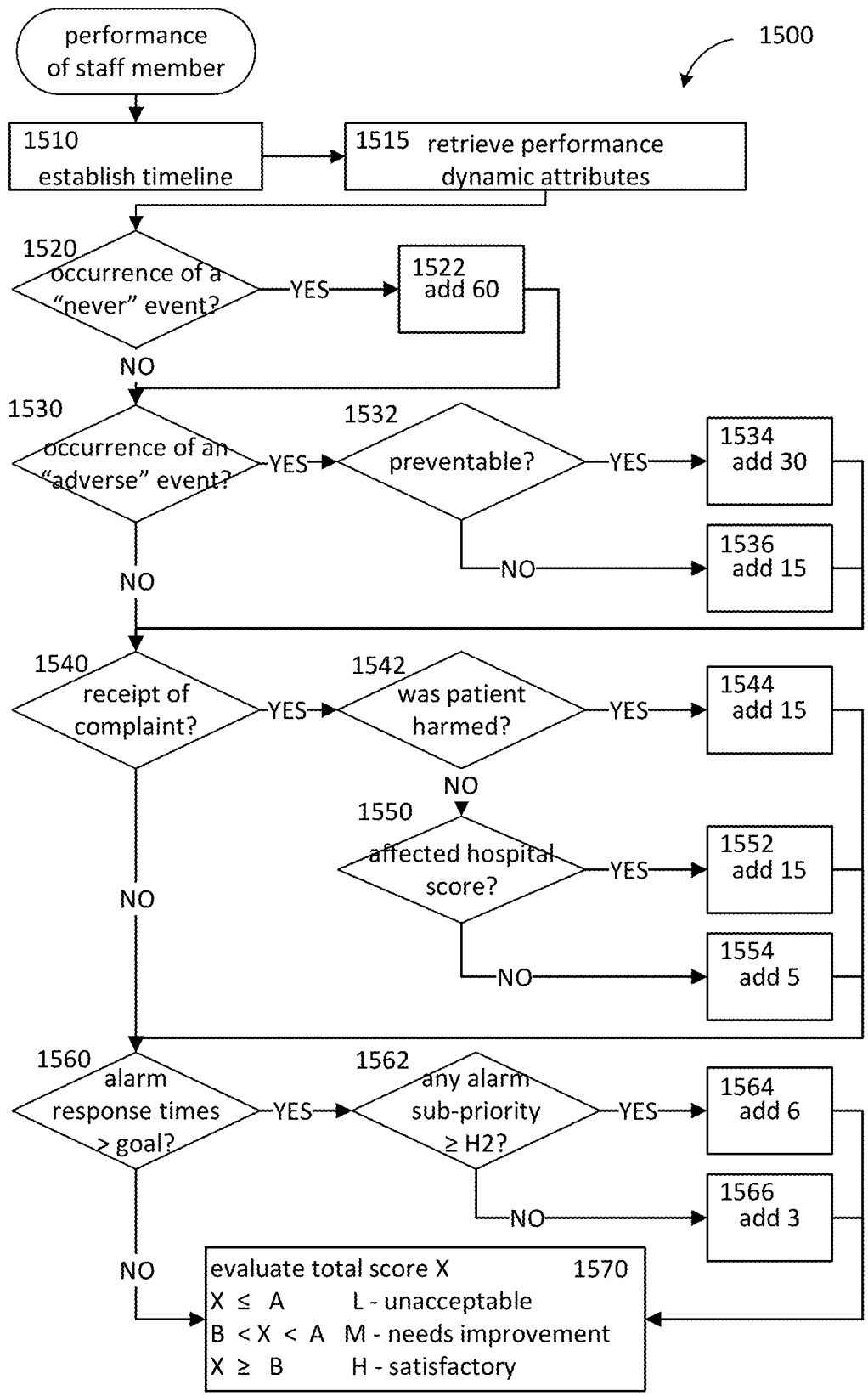
FIG. 15 is a flowchart of an exemplary embodiment of a workflow to determine a performance of a staff member, according to certain aspects of the present disclosure.

FIG. 15 is a flowchart of an exemplary embodiment of a workflow 1500 to determine a performance of a staff member, according to certain aspects of the present disclosure. The process starts at Step 1510 where the hospital defines the period of time the performance is evaluated for a staff member (e.g., current month, last 90 days, etc.). In certain embodiments, workflow 1500 calculates a score by assigning points to each event that contributes to the performance of the staff member. In certain embodiments, determining the performance of a staff member is done by determining how many instances for each event has occurred, assigning an acceptability to these number of occurrences for each event, and assigning a score based on whether the staff member meet the acceptability criterion or not.

Once a period is selected, step 1515 retrieves performance related dynamic attributes for a staff member from the hospital's quality and risk management program or the database of the alarm management system described herein. Examples of performance dynamic attributes include never events, adverse events, complaints that involved patient harm, and complaints that did not involve patient harm but affected a hospital ranking score, e.g., the Centers for Medicare and Medicaid Services (CMS) survey or the Hospital Consumer Assessment of Healthcare Providers and Systems (HCAHPS) survey.

In certain embodiments, each event is considered in only one category of events. For example, a patient's family member may complain about an action performed by a staff member that resulted in harm. If this event caused injury or death, then this event would be classified as an adverse event and not a complaint. If this same event was classified as a never event, then the event would be classified as a never event and not an adverse event or a complaint.

In certain embodiments, the alarm management system can pull information regarding the number of alarms to which a staff member responded and determine whether the alarm response time exceeded a predetermined goal for the type of alarm sub-priority, e.g., there may be a goal for time to respond to alarms having a sub-priority ≥H2.

Classifying an event often requires an in-depth investigation by the hospital quality and risk personnel. The investigation may determine that an individual staff member was responsible, that a group of staff members were collectively responsible, or that it cannot be determined who was responsible. Workflow 1500 considers only events that have been classified and attributed to a specific staff member. In certain embodiments, the workflow tallies events for which a care team that includes the staff member was responsible.

The workflow 1500 continues to step 1520 and determines how many never events have occurred in the period established in step 1510. For each occurrence of a never event, step 1522 assigns a predefined number of points (e.g., 60 points). If never events have not occurred, or points are assigned in step 1522, then the workflow 1500 branches to step 1530.

Step 1530 determines how many adverse events have occurred during the defined period and then proceeds to step 1532 to determine if each adverse event was deemed to be preventable or not. Step 1534 assigns 30 points for each preventable adverse event and step 1536 assigns 15 points for each non-preventable adverse event. If adverse events have not occurred or points have been assigned in steps 1534 and 1536 then the workflow 1500 branches to step 1540.

Step 1540 determines how many complaints have occurred within the period. Complaints can be reported by the patient, a person associated with the patient, another staff member or by an anonymous source. For each complaint, step 1542 determines if patient harm was associated, and step 1550 determines if the complaint affected a score associated with the hospital. This score can be an internal scoring system, or a scoring system implemented by an outside source, e.g., a HCAHPS survey. Steps 1544 and 1552 assign 15 points to complaints where patient harm was associated or the complaint affected a hospital score, respectively. Step 1554 assigns 5 points if the complaints did not result in either of these outcomes. If no complaints were received or points were assigned in steps 1544, 1552, and or 1554, then the workflow 1500 branches to step 1560.

Step 1560 determines how many alarm responses by a staff member exceeded the alarm response goal defined for a specific priority or sub-priority. Step 1562 further determines if the original sub-priority, i.e., before escalation, was greater than a pre-determined sub-priority, e.g., H1 or H2. Step 1564 assigns more points (e.g., 6 points) for responses that exceed a goal for alarms assigned a higher sub-priority and step 1566 assigns fewer points (e.g., 3 points) for responses that exceed a goal for alarms assigned a lower sub-priority.

Step 1570 tallies all the points and calculates a value. In workflow 1500, three performance levels are assigned based on the value. If the value is less than or equal to a first threshold A, then the performance classification is "low" or "unacceptable." If the value is between A and a higher second threshold B, then the performance classification is "medium" or "needs improvement." If the value is greater than or equal to B, then the performance classification is "high" or "satisfactory."

FIG. 16 is a block diagram 1600 of an exemplary alarm management system 1610, according to certain aspects of the present disclosure. The system 1610 comprises a processor 1612 that is communicatively coupled to a memory 1614, a user interface 1620, and a communication module 1624, an alarm sub-priority system 1604, and a staff management database 1606.

In certain embodiments, the processor 1612 is a device configured to retrieve instructions from a communicatively coupled memory, e.g., memory 1614, and execute the instructions. In certain embodiments, the processor 1612 is implemented as a physical device within a personal computer, a server, laptop, tablet, or other conventional computer. In certain embodiments, the processor 1612 is implemented as a Virtual Machine (VM) running on a physical server. In certain embodiments, the processor 1612 is implemented on a remote service, e.g., running in "the cloud."

In certain embodiments, the memory 1614 is communicatively coupled to a Real Time Location System (RTLS) that is configured to provide information comprising one or more of a current location of a staff member and a current location of the medical device 1602. In certain embodiments, the information is received by the processor 1612 and stored in the memory 1614. In certain embodiments, the information is transferred directly into the memory 1614.

In certain embodiments, the user interface 1620 is implemented as a browser-based graphic user interface (GUI) provided on a desktop computer, for example at a nurses' station or a supervisor's desk. In certain embodiments, the user interface 1620 is implemented on a mobile device, e.g., a smart phone or tablet. In certain embodiments, the user interface 1620 provides an overview of the status of one or more staff members. In certain embodiments, the overview comprises a dynamic attribute of the one or more staff members. In certain embodiments, the overview comprises a status of an active alarm. In certain embodiments, the status of the active alarm comprises one or more of the medical device that issued the alarm, the location of the medical device, the patient associated with the medical device, information about the patient, an assigned sub-priority, changes in the sub-priority since receipt of the alarm, a recipient of an alert associated with the alarm, a time at which the alert was transmitted.

In certain embodiments, a portion of the alarm management system 1610, e.g., the processor 1612, is disposed in a computer proximate to the patient, e.g., at a nurses' station. In certain embodiments, a portion of the alarm management system 1610, e.g., the processor 1612, is disposed in a server located in a hospital or a medical care facility. In certain embodiments, a portion of the alarm management system 1610, e.g., the memory 1614, is implemented as a cloud-based service.

In certain embodiments, the RTLS 1608 provides a current location of staff members in the facility, for example staff member 1601. In certain embodiments, the RTLS 1608 provides a location of the medical device 1602 that issued the alarm. In certain embodiments, the RTLS 1608 is a conventional location determination system that utilizes one or more of access point tracking for communication with a device carried by the staff member, triangulation of the device based on signal strength at a plurality of access point. In certain embodiments, the RTLS 1608 comprises a Global Positioning System (GPS) module carried by the staff member that determines and provides a geophysical location of the staff member.

The communication module 1624 is configured to connect to conventional external communication systems (not shown), e.g., wired or wireless computer networks, that further are configured to connect to personal communication devices carried by staff members 1601, e.g., a pager, a mobile phone, a smart phone running an application, or a device configured to receive an alert. When provided with an identification of a staff member and an identification of an alert, the communication module 1624 is configured to transmit the identified alert to the identified staff member.

Aspects

Aspect M1. A method for managing an alarm issued by a medical device, comprising the steps of receiving the alarm from the medical device; ranking a staff member based in part on a dynamic attribute that is associated with the staff member; selecting a recipient based in part on the ranking; and providing an alert to the recipient.

Aspect M2. The method of Aspect M1, wherein the dynamic attribute is selected from a group of attributes consisting of: capability; availability; workload; burnout; performance; and management.

Aspect M3. The method of Aspect M2, wherein the capability attribute is based in part on one or more of the group consisting of: education; experience; and training.

Aspect M4. The method of Aspect M2, wherein the availability attribute is based in part on one or more of the group consisting of: break status; distance from the staff member to the medical device; do not disturb (DND) status.

Aspect M5. The method of Aspect M2, wherein the workload attribute is based in part on one or more of the group consisting of: a number of patients assigned to the staff member; a number of patients having a patient health assessment score above a threshold; a number of active alarms above a sub-priority threshold and assigned to the staff member; and a patient who requires special care assigned to the staff member.

Aspect M6. The method of Aspect M2, wherein the burnout attribute is based in part on one or more of the group consisting of: a reported level of burnout; a measurement; a grief event; and a work schedule.

Aspect M7. The method of Aspect M2, wherein the performance attribute is based in part on one or more of the group consisting of: a never event; a preventable adverse event; a patient complaint; and an alarm response time >goal.

Aspect M8. The method of Aspect M2, wherein the management attribute is based in part on one or more of the group consisting of: a number of backups to the staff member; whether the staff member is assigned as a backup to another staff member; and staffing level of current shift.

Aspect S1. A system for managing an alarm issued by a medical device, comprising: a processor configured to receive the alarm and provide an alert; and a memory communicatively coupled to the processor, the memory comprising: a dynamic attribute of a staff member; an algorithm for retrieving the dynamic attribute and ranking the staff member based in part on the dynamic attribute and selecting a recipient based in part on the ranking; and instructions that, when loaded into the processor and executed, cause the processor to execute the algorithm upon receipt of the alarm and provide the alert to the recipient.

Aspect S2. The system of claim Aspect S1, wherein the dynamic attribute is selected from a group of attributes consisting of: capability; availability; workload; burnout; performance; and management.

Aspect S3. The system of claim Aspect S2, wherein the capability attribute is based in part on one or more of the group consisting of: education; experience; and training.

Aspect S4. The system of claim Aspect S2, wherein the availability attribute is based in part on one or more of the group consisting of: break status; distance from the staff member to the medical device; and do not disturb (DND) status.

Aspect S5. The system of claim Aspect S2, wherein the workload attribute is based in part on one or more of the group consisting of: a number of patients assigned to the staff member; a number of patients having a patient health assessment score above a threshold; a number of active alarms above a sub-priority threshold and assigned to the staff member; and a patient who requires special care assigned to the staff member.

Aspect S6. The system of claim Aspect S2, wherein the burnout attribute is based in part on one or more of the group consisting of: a reported level of burnout; a measurement; a grief event; and a work schedule.

Aspect S7. The system of claim Aspect S2, wherein the performance attribute is based in part on one or more of the group consisting of: a never event; a preventable adverse event; a patient complaint; and an alarm response time >goal.

Aspect S8. The system of claim Aspect S2, wherein the management attribute is based in part on one or more of the group consisting of: a number of backups to the staff member; whether the staff member is assigned as a backup to another staff member; and staffing level of current shift.

Aspect DND1. A method of assigning a Do Not Disturb (DND) status to a staff member, the method comprising the steps of: retrieving a dynamic attribute, for which an associated alert was provided to the staff member, from a group comprising: a first number of active alarms having respective sub-priorities greater than a predetermined first level; a second number of active alarms that require a response having a complexity equal to or greater than a predetermined second level; and a third number of active emergency codes; and assigning the DND status based on the retrieved dynamic attribute.

Aspect DND2. The method of aspect DND1, wherein the DND status is assigned when the first number is one or greater and the first level is M1.

Aspect DND3. The method of aspect DND1, wherein the DND status is assigned when the second number is one or greater and the second level is "high."

Aspect DND4. The method of aspect DND3, wherein the DND status is assigned when the second number is two or greater and the second level is "medium."

Aspect DND5. The method of aspect DND1, wherein the DND status is assigned when the third number is one or greater and the emergency code is one of a group comprising a fire and a life-threatening event.

Aspect DND6. The method of aspect DND5, wherein a fire is a "code red" and is declared based on one or more of seeing flames, seeing smoke, and smelling smoke; and a life-threatening event is a "code blue" and is declared based on one or more of a cardiac arrest and a respiratory failure.

Aspect DND7. The method of aspect DND5, wherein the group of emergency codes further comprises one or more of a bomb threat, a severe weather condition, a disaster condition, a weapon, a hazardous material event, and an infant or child abduction.

Aspect DND8. The method of aspect DND1, wherein: the group of dynamic attributes further comprises a location at which an emergency code has been declared and a location of the staff member; and the DND status is assigned when an emergency code has been declared and the staff member is within a predetermined distance of the location at which the emergency code has been declared.

Aspect AL1. A method of managing an alarm issued by a medical device, the method comprising the steps of: receiving the alarm from the medical device; ranking a staff member based in part on a dynamic attribute that is associated with the staff member; selecting a recipient based in part on the ranking; and providing an alert to the recipient, wherein the alert comprises a ranking of all active alarms previously assigned to the staff member.

Aspect AL2. The method of ALL wherein the ranking is based in part on current sub-priorities assigned to the previously assigned alarms.

Aspect AL3. The method of AL1, wherein the ranking is based in part on a dynamic attribute of the previously assigned alarms.

Aspect AL4. A method of managing an alarm issued by a medical device, the method comprising the steps of: receiving the alarm from the medical device; ranking a staff member based in part on a dynamic attribute that is associated with the staff member; selecting a recipient based in part on the ranking; retrieving all active alarms that have been previously assigned to the staff member; re-assigning at least one of the previously assigned alarms to another staff member; and providing an alert to the recipient, wherein the alert comprises a notification that the at least one of the previously assigned alarms has been re-assigned to another staff member.

Headings and subheadings, if any, are used for convenience only and do not limit the invention.

Reference to an element in the singular is not intended to mean "one and only one" unless specifically so stated, but rather "one or more." Use of the articles "a" and "an" is to be interpreted as equivalent to the phrase "at least one." Unless specifically stated otherwise, the terms "a set" and "some" refer to one or more.

Terms such as "top," "bottom," "upper," "lower," "left," "right," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Although the relationships among various components are described herein and/or are illustrated as being orthogonal or perpendicular, those components can be arranged in other configurations in some embodiments. For example, the angles formed between the referenced components can be greater or less than 90 degrees in some embodiments.

Although various components are illustrated as being flat and/or straight, those components can have other configurations, such as curved or tapered for example, in some embodiments.

Pronouns in the masculine, e.g., "his," include the feminine and neuter gender, e.g., "her" and "its" and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "operation for."

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such as an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A method for managing a task, comprising the steps:
   identifying the task;
   ranking a staff member based in part on a staff member dynamic attribute that is associated with the staff member;
   selecting a recipient based in part on the ranking;
   assigning the task to the recipient; and
   reassigning one or more tasks previously assigned to the recipient to another staff member.

2. The method of claim 1, wherein the dynamic attribute is selected from a group of attributes consisting of:
capability;
availability;
workload;
burnout;
performance; and
management.

3. The method of claim 2, wherein the capability attribute is based in part on one or more of the group consisting of:
education;
experience; and
training.

4. The method of claim 2, wherein:
the task comprises one or more of a patient task and a device task;
the availability attribute is based in part on one or more of the group consisting of:
break status; and
do not disturb (DND) status.

5. The method of claim 2, wherein the workload attribute is based in part on one or more of the group consisting of:
a number of patients currently assigned to the staff member;
a number of currently assigned patients having a patient health assessment score above a threshold;
a number of active alarms above a sub-priority threshold and currently assigned to the staff member; and
a currently assigned patient who requires special care assigned to the staff member.

6. The method of claim 2, wherein the burnout attribute is based in part on one or more of the group consisting of:
a reported level of burnout;
a measurement;
a grief event; and
a work schedule.

7. The method of claim 2, wherein the performance attribute is based in part on one or more of the group consisting of:
a never event;
a preventable adverse event; and
an alarm response time >goal.

8. The method of claim 2, wherein the management attribute is based in part on one or more of the group consisting of:
a number of backups to the staff member;
whether the staff member is assigned as a backup to another staff member; and
staffing level of current shift.

9. A system for managing a task, comprising:
a processor configured to accept an identification of the task; and
a memory communicatively coupled to the processor, the memory comprising:
a dynamic attribute of a staff member;
an algorithm for retrieving the dynamic attribute, ranking the staff member based in part on the dynamic attribute, selecting a recipient based in part on the ranking, assigning the task to the recipient; and reassigning one or more tasks previously assigned to the recipient to another staff member; and
instructions that, when loaded into the processor and executed, cause the processor to execute the algorithm upon identification of the task.

10. The method of claim 1, wherein:
the task comprises resolution of an alarm received from a medical device; and
assigning the task comprises providing an alert to the recipient.

11. The method of claim 10, wherein:
ranking the staff member comprises a determination of whether the staff member has a capability to perform a corrective action to address the medical device alarm.

12. The method of claim 1, further comprising:
determining a criticality of the task based in part on a dynamic attribute of the recipient; and
assigning, when the determined criticality is greater than a threshold, a Do Not Disturb (DND) status to the recipient.

13. The method of claim 1, wherein ranking the staff member excludes a staff member who is currently assigned a Do Not Disturb (DND) status.

14. The method of claim 1, wherein ranking the staff member, if the task is associated with a patient under special care, comprises assessment of a special skill associated with the special care.

15. The method of claim 1, wherein ranking the staff member comprises using a patient dynamic attribute to select one of more dynamic attributes of the staff member to consider in the ranking.

16. A non-volatile memory comprising instructions that, when loaded into a processor and executed, cause the processor to perform steps of:
identifying a task;
ranking a staff member based in part on a dynamic attribute that is associated with the staff member;
selecting a recipient based in part on the ranking;
assigning the task to the recipient; and
reassigning one or more tasks previously assigned to the recipient to another staff member.

* * * * *